(12) United States Patent
Li et al.

(10) Patent No.: US 12,275,986 B2
(45) Date of Patent: Apr. 15, 2025

(54) BIOMARKERS ASSOCIATED WITH CHECKPOINT IMMUNE THERAPY AND METHODS OF USING SAME

(71) Applicant: Duke University, Durham, NC (US)

(72) Inventors: Chuan-Yuan Li, Durham, NC (US); Dong Pan, Durham, NC (US)

(73) Assignee: Duke University, Durham, NC (US)

( * ) Notice: Subject to any disclaimer, the term of this patent is extended or adjusted under 35 U.S.C. 154(b) by 490 days.

(21) Appl. No.: 17/142,844

(22) Filed: Jan. 6, 2021

(65) Prior Publication Data

US 2021/0207198 A1 Jul. 8, 2021

Related U.S. Application Data

(60) Provisional application No. 62/957,370, filed on Jan. 6, 2020.

(51) Int. Cl.
*C12Q 1/6827* (2018.01)
*A61P 35/00* (2006.01)
*C07K 16/28* (2006.01)

(52) U.S. Cl.
CPC ............ *C12Q 1/6827* (2013.01); *A61P 35/00* (2018.01); *C07K 16/2818* (2013.01); *C07K 16/2827* (2013.01); *C12Q 2535/101* (2013.01)

(58) Field of Classification Search
CPC ... C12Q 1/6827; A61P 35/00; C07K 16/2818; C07K 16/2827
See application file for complete search history.

(56) References Cited

U.S. PATENT DOCUMENTS

| 10,286,197 B2 | 5/2019 | Pouliot et al. |
|---|---|---|
| 2004/0180095 A1 | 9/2004 | Menei et al. |
| 2008/0241223 A1 | 10/2008 | Nivaggioli et al. |

FOREIGN PATENT DOCUMENTS

| CN | 110229894 A | * | 9/2019 | ............ C12Q 1/6886 |
|---|---|---|---|---|
| WO | WO-2018146148 A1 | * | 8/2018 | ............ C12Q 1/6886 |
| WO | WO-2018178040 A1 | * | 10/2018 | ......... A61K 31/4745 |
| WO | WO-2018223040 A1 | * | 12/2018 | .............. A61P 35/00 |

OTHER PUBLICATIONS

Guibert et al. "Targeted sequencing of plasma cell-free DNA to predict response to PD1 inhibitors in advanced non-small cell lung cancer", Lung Cancer. Nov. 2019;137:1-6. (Year: 2019).*
Havel et al. "The evolving landscape of biomarkers for checkpoint inhibitor immunotherapy", Nat Rev Cancer. Mar. 2019;19(3):133-150 (Year: 2019).*
Cheng et al., "Memorial Sloan Kettering-Integrated Mutation Profiling of Actionable Cancer Targets (MSK-IMPACT) A Hybridization Capture-Based Next-Generation Sequencing Clinical Assay for Solid Tumor Molecular Oncology", J Mol Diagn.; 17(3), May 2015, pp. 251-264.
Govindarajan et al., "Microarray and its applications", J Pharm Bioallied Sci; 4(Suppl 2):, Aug. 2012, pp. S310-S312.
Hellmann et al., "Genomic Features of Response to Combination Immunotherapy in Patients with Advanced Non-Small-Cell Lung Cancer", Cancer Cell., 33(5), May 14, 2018, pp. 843-852.
Hoadley et al., "Cell-of-Origin Patterns Dominate the Molecular Classification of 10,000 Tumors from 33 Types of Cancer", Cell, 173(2), Apr. 5, 2018, pp. 291-304.
Kim et al., "Microarray Applications in Cancer Research", Cancer Res Treat.; 36(4), Aug. 2004, pp. 207-213.
Lohmann et al., "Gene expression analysis in biomarker research and early drug development using function tested reverse transcription quantitative real-time PCR assays", Methods, 59, 2013, pp. 10-19.
Newman et al., "Robust enumeration of cell subsets from tissue expression profiles", Nature Methods, vol. 12, 2015, pp. 453-457.
Rizvi et al., "Molecular Determinants of Response to Anti-Programmed Cell Death (PD)-1 and Anti-Programmed Death-Ligand 1 (PD-L1) Blockade in Patients With Non-Small-Cell Lung Cancer Profiled With Targeted Next-Generation Sequencing", J Clin Oncol., 36(7), Mar. 1, 2018, pp. 633-641.
Rizvi et al., "Mutational landscape determines sensitivity to PD-1 blockade in non-small cell lung cancer", Science, 348(6230), Apr. 3, 2015, pp. 124-128.
Samstein et al., "Tumor mutational load predicts survival after immunotherapy across multiple cancer types", Nature Genetics, vol. 51, 2019, pp. 202-206.
Virtanen et al., "Clinical Uses of Microarrays in Cancer Research", Methods Mol Med.; 141, 2008, pp. 87-113.
Williams et al., "Validation of the Oncomine™ focus panel for next-generation sequencing of clinical tumour samples", Virchows Archiv, vol. 473, 2018, pp. 489-503.
Woodhouse et al., "Clinical and analytical validation of FoundationOne Liquid CDx, a novel 324-Gene cfDNA-based comprehensive genomic profiling assay for cancers of solid tumor origin", PLOS One 15(9): e0237802, Sep. 25, 2020, 18 pages.
Xu et al., "TIP: A Web Server for Resolving Tumor Immunophenotype Profiling", Cancer Research, vol. 78, Issue 23, Dec. 1, 2018, pp. 6575-6580.
Zehir et al., "Mutational landscape of metastatic cancer revealed from prospective clinical sequencing of 10,000 patients", Nat Med., 23(6), Jun. 2017, pp. 703-713.

* cited by examiner

*Primary Examiner* — Amy E Juedes
*Assistant Examiner* — Peter Johansen
(74) *Attorney, Agent, or Firm* — Kilpatrick Townsend & Stockton LLP

(57) ABSTRACT

Provided herein are methods for treating cancer in a subject comprising administering an ICB therapy to a subject having cancer, wherein the subject's cancer comprises one or more mutations in two or more genes associated with responsiveness to immune checkpoint blockade (ICB).

13 Claims, 33 Drawing Sheets

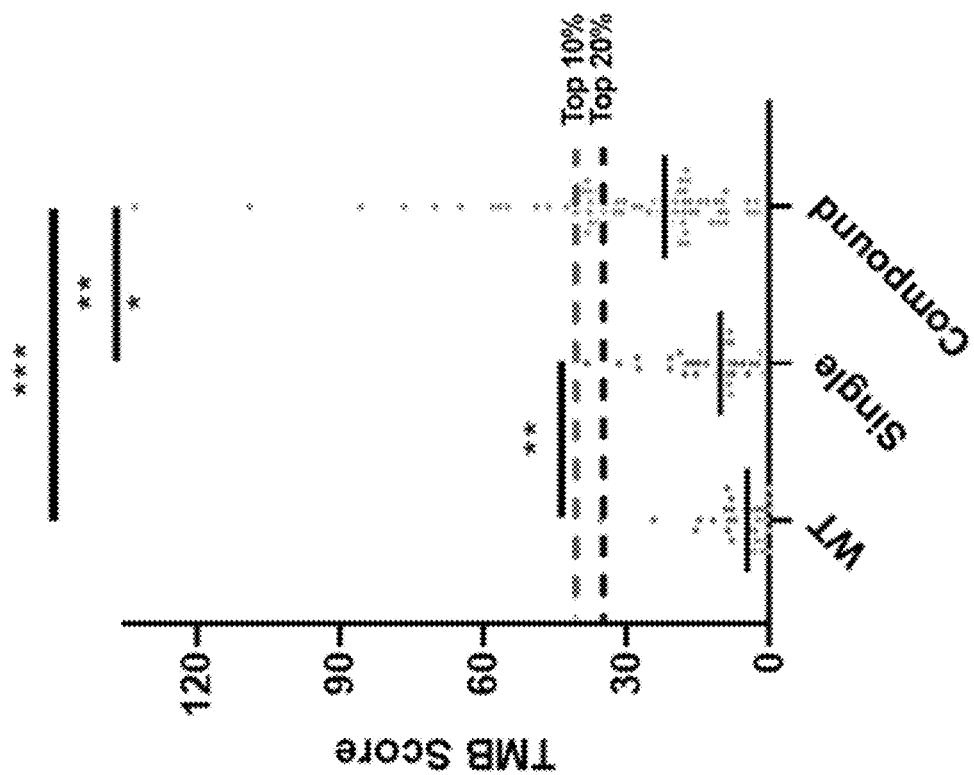
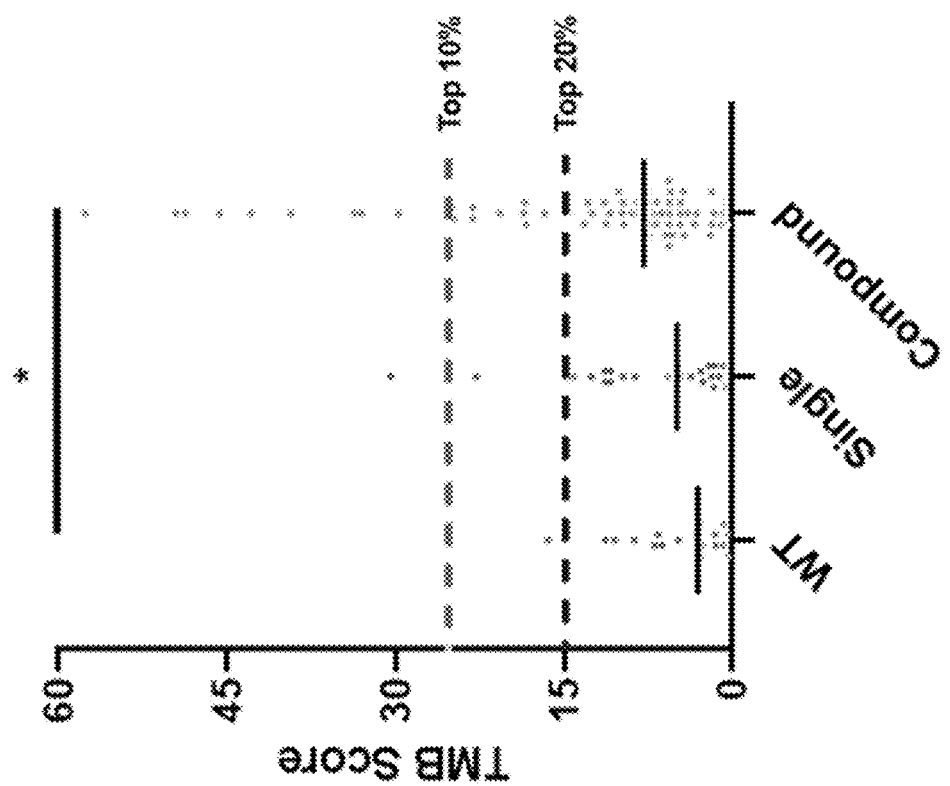
FIG. 9B
FIG. 9A

BIOMARKERS ASSOCIATED WITH CHECKPOINT IMMUNE THERAPY AND METHODS OF USING SAME

PRIOR RELATED APPLICATION

This application claims the benefit of and priority to U.S. Provisional Application No. 62/957,370 filed on Jan. 6, 2019, which is hereby incorporated by reference in its entirety.

STATEMENT REGARDING FEDERALLY FUNDED RESEARCH

This invention was made with government support under Grant Nos. CA208852 and CA216876 awarded by the National Institutes of Health/National Cancer Institute. The government has certain rights in the invention.

FIELD

This disclosure describes compositions and methods for treating cancer.

BACKGROUND

Immune checkpoint blockade (ICB) treatment for cancer has shown great promise due to the existence of durable responders among advanced stage patients. However, only a minority of patients respond to ICB treatment among eligible candidates. Given the costs associated with ICB treatments and severe side effects, there is an unmet need for novel treatments, based on more precise identification of patients who can benefit from such treatments.

SUMMARY

Provided herein are methods for treating cancer in a subject. The methods comprise (a) identifying one or more mutations in two or more genes associated with responsiveness to immune checkpoint blockade (ICB) therapy, in a biological sample from a subject having cancer, wherein the presence of one or more mutations in the two or more genes associated with responsiveness to ICB indicates the subject is responsiveness to ICB therapy; and (b) administering an ICB therapy to the subject having cancer that is responsive to ICB therapy.

Also provided is a method for treating cancer in a subject comprising administering an ICB therapy to a subject having cancer, wherein the subject's cancer comprises one or more mutations in two or more genes associated with responsiveness to ICB.

In some embodiments, the cancer is selected from the group consisting of non-small cell lung cancer (NSCLC), bladder cancer, skin cancer, renal cell carcinoma, colorectal cancer, esophagastric cancer, head and neck cancer, glioma, and breast cancer.

In some embodiments, the cancer is NSCLC and the method comprises: (a) identifying one or more mutations in two or more genes selected from the group consisting of ABL1, ASXL1, ATM, BCOR, BRCA2, BRIP1, CARD11, CD79B, CDC73, CIC, EPHA3, EPHA5, EPHA, EPHB1, ERBB4, ERCC4, FGFR4, FLT3, FOXL2, HGF, INHBA, JAK3, MAX, MDC1, MED12, MET, MGA, MRE11, MSH2 NF2, NFKBIA, NOTCH1, NOTCH2, NTRK3, NUF, PARP1, PAX5, PGR, PIK3C2G, PIK3C3, PIK3CG, PIM1, POLE PPM1D, PPP2R1A, PTPRD, RET, STAT3, TENT, TET1, TSC2, and ZFHX3 in a biological sample from the subject having NSCLC, wherein the presence of one or more mutations in the two or more genes indicates the subject is responsive to ICB therapy; and (b) administering ICB therapy to the subject having NSCLC that is responsive to ICB therapy.

In some embodiments, the cancer is NSCLC and the method comprises the method comprises: (a) identifying one or more mutations in the ABL1, ASXL1, ATM, BCOR, BRCA2, BRIP1, CARD11, CD79B, CDC73, CIC, EPHA3, EPHA5, EPHA, EPHB1, ERBB4, ERCC4, FGFR4, FLT3, FOXL2, HGF, INHBA, JAK3, MAX, MDC1, MED12, MET, MGA, MRE11, MSH2 NF2, NFKBIA, NOTCH1, NOTCH2, NTRK3, NUF, PARP1, PAX5, PGR, PIK3C2G, PIK3C3, PIK3CG, PIM1, POLE, PPM1D, PPP2R1A, PTPRD, RET, STAT3, TENT, TET1, TSC2, and ZFHX3 genes in a biological sample from the subject, wherein the presence of one or more mutations in two or more genes indicates the subject is responsive to ICB therapy; and (b) administering ICB therapy to the subject that is responsive to ICB therapy.

In some embodiments, the cancer is NSCLC and the method comprises: (a) identifying one or more mutations in two or more genes selected from the group consisting of ABL1, ALK, ASXL1, ASXL2, ATM, AXIN2, BCOR, BRCA2, BRIP1, CARD11, CARM1, CD79B, CDC73, CIC, DDR2, DNAJB1, EPHA3, EPHA5, EPHA7, EPHB1, ERBB4, ERCC4, FGFR4, FLT3, FOXL2, HGF, IL7R, INHA, INHBA, IRS2, JAK3, KMT2A, KMT2C, LATS1, MAX, MDC1, MED12, MET, MGA, MRE11, MSH2, NF2, NFKBIA, NKX2-1, NOTCH1, NOTCH2, NTRK3, NUF2, PARP1, PAX5, PGR, PIK3C2G, PIK3C3, PIK3CG, PIM1, POLE, PPM1D, PPP2R1A, PTPRD, RET, SF3B1, STAT3, STAT5B, TENT5C, TERT, TET1, TSC2, and ZFHX3 in a biological sample from the subject having NSCLC, wherein the presence of one or more mutations in the two or more genes indicates the subject is responsive to ICB therapy; and (b) administering ICB therapy to the subject having NSCLC that is responsive to ICB therapy.

In some embodiments, the cancer is NSCLC and the method comprises: (a) identifying one or more mutations in ABL1, ALK, ATM, BRCA1, BTK, CARM1, CREBBP, CTCF, CYLD, DNMT1, DNMT3A, DROSHA, EPHAS, EPHA7, EPHB1, ERBB3, FAT1, FBXW7, FGFR2, FGFR4, FLT3, KDR, LYN, MAX, MSI1, NCOA3, NCOR1, NF2, NOTCH3, NTRK3, NUF2, PALB2, PPM1D, PREX2, PTPRD, RNF43, ROS1, SHOC2, SMO, STAT5B, TET1, and ZFHX3 genes in a biological sample from the subject having NSCLC, wherein the presence of one or more mutations in two or more genes indicates the subject is responsive to ICB therapy; and (b) administering ICB therapy to the subject having NSCLC that is responsive to ICB therapy.

In some embodiments, the cancer is NSCLC and the method comprises (a) identifying one or more mutations in two or more genes selected from the group consisting of ABL1, ALK, ATM, BRCA1, BTK, CARM1, CREBBP, CTCF, CYLD, DNMT1, DNMT3A, DROSHA, EPHAS, EPHA7, EPHB1, ERBB3, FAT1, FBXW7, FGFR2, FGFR4, FLT3, KDR, LYN, MAX, MSI1, NCOA3, NCOR1, NF2, NOTCH3, NTRK3, NUF2, PALB2, PPM1D, PREX2, PTPRD, RNF43, ROS1, SHOC2, SMO, STAT5B, TET1, and ZFHX3 in a biological sample from the subject having NSCLC, wherein the presence of one or more mutations in the two or more genes indicates the subject is responsive to ICB therapy; and (b) administering ICB therapy to the subject having NSCLC that is responsive to ICB therapy.

In some embodiments, the cancer is NSCLC and the method comprises: (a) identifying one or more mutations in the ABL1, ALK, ASXL1, ASXL2, ATM, AXIN2, BCOR, BRCA2, BRIP1, CARD11, CARM1, CD79B, CDC73, CIC, DDR2, DNAJB1, EPHA3, EPHA5, EPHA7, EPHB1, ERBB4, ERCC4, FGFR4, FLT3, FOXL2, HGF, IL7R, INHA, INHBA, IRS2, JAK3, KMT2A, KMT2C, LATS1, MAX, MDC1, MED12, MET, MGA, MRE11, MSH2, NF2, NFKBIA, NKX2-1, NOTCH1, NOTCH2, NTRK3, NUF2, PARP1, PAX5, PGR, PIK3C2G, PIK3C3, PIK3CG, PIM1, POLE, PPM1D, PPP2R1A, PTPRD, RET, SF3B1, STAT3, STAT5B, TENT5C, TERT, TET1, TSC2, and ZFHX3 genes in a biological sample from the subject, wherein the presence of one or more mutations in two or more genes indicates the subject is responsive to ICB therapy; and (b) administering ICB therapy to the subject having NSCLC that is responsive to ICB therapy.

In some embodiments, the cancer is NSCLC and the method comprises: (a) identifying one or more mutations in two or more genes selected from the group consisting of ABL1, ACVR1, BBC3, BCL2L1, BCL6, CARM1, CCNE1, CD274, CD74, CD79B, CDC73, CDKN1A, CHEK1, CRLF2, CSF1R, CTLA4, CYSLTR2, DCUN1D1, DHFRP3, DNAH2, DNAJB1, E2F3, EED, EGFL7, ENSA, EPHA7, ERCC3, ERCC4, ERRFI1, ETV1, FBRSL1, FGFR4, FLCN, FLT3, FOXL2, GNAQ, HIST1H3E, HIST1H3H, HIST3H3, IKZF1, INHA, JUN, KNSTRN, MAPKAP1, MAX, MDM4, MRE11, MSH2, MSH3, MYCL, NF2, NFKBIA, NKX3-1, NRG1, NTRK3, NUF2, ONECUT1, PARP1, PAX5, PDPK1, PIK3C3, PIK3CD, PIM1, PPM1D, PPP2R1A, PRDM1, RAC2, RAD50, RAD51B, RAD51C, REL, RRAGC, RYBP, SDHAF2, SDHAP3, SLC34A2, STAT3, STAT5B, TAP2, TENT5C, TET1, and ZFHX3 in a biological sample from the subject having NSCLC, wherein the presence of one or more mutations in the two or more genes indicates the subject is responsive to ICB therapy; and (b) administering ICB therapy to the subject having NSCLC that is responsive to ICB therapy.

In some embodiments, the cancer is NSCLC and the method comprises: (a) identifying one or more mutations in the ABL1, ACVR1, BBC3, BCL2L1, BCL6, CARM1, CCNE1, CD274, CD74, CD79B, CDC73, CDKN1A, CHEK1, CRLF2, CSF1R, CTLA4, CYSLTR2, DCUN1D1, DHFRP3, DNAH2, DNAJB1, E2F3, EED, EGFL7, ENSA, EPHA7, ERCC3, ERCC4, ERRFI1, ETV1, FBRSL1, FGFR4, FLCN, FLT3, FOXL2, GNAQ, HIST1H3E, HIST1H3H, HIST3H3, IKZF1, INHA, JUN, KNSTRN, MAPKAP1, MAX, MDM4, MRE11, MSH2, MSH3, MYCL, NF2, NFKBIA, NKX3-1, NRG1, NTRK3, NUF2, ONECUT1, PARP1, PAX5, PDPK1, PIK3C3, PIK3CD, PIM1, PPM1D, PPP2R1A, PRDM1, RAC2, RAD50, RAD51B, RAD51C, REL, RRAGC, RYBP, SDHAF2, SDHAP3, SLC34A2, STAT3, STAT5B, TAP2, TENT5C, TET1, and ZFHX3 genes in a biological sample from the subject, wherein the presence of one or more mutations in two or more genes indicates the subject is responsive to ICB therapy; and (b) administering ICB therapy to the subject having NSCLC that is responsive to ICB therapy.

In some embodiments, the ICB therapy is selected from the group consisting of a PD-1 inhibitor, a PD-L1 inhibitor or a CTLA4 inhibitor, and combinations thereof. In some embodiments, the ICB therapy comprises an antibody selected from the group consisting of an anti-PD1 antibody, anti-PD-L1 antibody, an anti-CTLA4 antibody, and any combinations thereof. In some embodiments, the antibody is selected from the group consisting of atezolizumab, avelumab, camrelizumab, cemiplimab, durvalumab, ipilimumab, nivolumab, pembrolizumab, sintilimab, Tislelizumab, Toripalimab, tremelimumab, and any combinations thereof.

In some embodiments, the one or more mutations are identified by next generation sequencing, whole exome sequencing, polymerase change reaction, Sanger sequencing, or targeted sequencing techniques. In some embodiments, the targeted sequencing technique is selected from the group consisting of MSK-IMPACT™, FoundationOne® CDx, Oncomine™, and any combinations thereof. In some embodiments, the one or more mutations are identified via DNA or RNA microarray analysis.

In some embodiments, the biological sample is a tumor biopsy from the subject. In some embodiments, the biological sample comprises circulating tumor cells. In some embodiments, the biological sample comprises circulating free DNA from the subject's blood.

DESCRIPTION OF THE FIGURES

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

(FIG. 1A) Kaplan-Meier survival analysis of 994 ICB-treated lung, melanoma, bladder and colorectal cancer patients with wildtype (WT), single, and compound (two or more) mutations signatures. Hazard ratio (HR) (compound vs. WT): 0.42 (95% confidence interval (CI)-0.34-0.51). (FIG. 1B) Kaplan-Meier survival analysis of 350 ICB-treated lung cancer patients with WT, single, and compound mutations signatures. HR (compound vs. WT): 0.50 (95% CI-0.36-0.69). (FIG. 1C) Kaplan-Meier survival analysis of 320 ICB-treated melanoma patients with WT, single, and compound mutations signatures. HR (compound vs. WT): 0.41 (95% CI-0.27-0.61). (FIG. 1D) Kaplan-Meier survival analysis of 214 ICB-treated bladder patients with WT, single, and compound mutations signatures. HR (compound vs. WT): 0.39 (95% CI-0.24-0.63). (FIG. 1E) Kaplan-Meier survival analysis of 110 ICB-treated colorectal cancer patients with WT, single, and compound mutations signatures. HR (compound vs. WT): 0.34 (95% CI-0.18-0.65).

(FIG. 4A) Kaplan-Meier analysis of progression free survival of 190 ICB-treated non small cell lung cancer (NSCLC) patients. HR (compound vs. WT): 0.51 (95% CI: 0.25-1.05). (FIG. 3B) Kaplan-Meier analysis of OS survival of 131 ICB-treated melanoma patients. HR (compound vs. WT): 0.28 (95% CI: 0.15-0.53).

(FIG. 5A) Kaplan-Meier survival analysis of anti-CTLA4 inhibitor-treated patients. HR (compound vs. WT): 0.26 (95% CI: 0.13-0.55). (FIG. 5B) Kaplan-Meier survival analysis of anti-PD1/PDL1 inhibitor-treated patients. HR (compound vs. WT): 0.49 (95% CI: 0.34-0.54). (FIG. 5C) Kaplan-Meier survival analysis of combined anti-CTLA4/anti-PD1/PDL1 inhibitor-treated patients. HR (compound vs. WT): 0.49 (95% CI: 0.27-0.89).

(FIG. 6A) Kaplan-Meier analysis of non-ICB treated NSCLC patients with wt, single, and compound mutation signatures. (FIG. 6B) Kaplan-Meier analysis of non-ICB treated melanoma patients with wt, single, and compound mutation signatures. (FIG. 6C) Kaplan-Meier analysis of non-ICB treated bladder cancer patients with wt, single, and compound mutation signatures. (FIG. 6D) Kaplan-Meier analysis of non-ICB treated colorectal cancer patients with wt, single, and compound mutation signatures.

(FIG. 7A) Median value of TMB in the compound mutation group was just at or above the top 20% TMB cut-off values in lung, bladder and colorectal cancer patients and slightly below in melanoma patients from the non-ICB treated cancer patients in the MSK-IMPACT cohort. (FIG. 7B) Similar to results shown in FIG. 7A, median value of TMB in compound group mutation group was just at or above the top 20% TMB cut-off values in lung, bladder and colorectal cancer patients, and slightly below in melanoma patients from the TCGA Pan-Cancer Atlas cohort. *p<0.05, p<0.01, *p<0.001, unpaired Students t-test. *p<0.05, p<0.01, *p<0.001, unpaired Students t-test.

FIGS. 9A-9B are graphs showing the TMB values among NSCLC and melanoma patients, respectively, with different mutation signatures in accordance with an embodiment of the present disclosure. Patients were independent of the MSK-TMB cohort and ICB-treated patients. *p<0.05, p<0.01, *p<0.001, two-tailed, unpaired Students t-test.

(FIG. 11A) OS of 350 ICB-treated MSK-TMB NSCLC patients with wt, single, and compound mutation signatures. Compound vs wt: Hazard ratio (HR)=0.43 (95% confidence interval [CI]: 0.31-0.59). (FIG. 11B) Progression-free survival (PFS) of 69 ICB-treated NSCLC patients with wt, single, and compound mutation signatures. These patients belong to a sub-cohort of the MSK-TMB NSCLC cohort in FIG. 11A for whom PFS data are available. Compound vs wt: HR=0.41 (95% [CI]: 0.22-0.79). Wt: patients with no mutations in the 52 gene panel; single: patients with only a single gene mutation in the 52-gene panel; compound: patients with two or more of genes mutated in the 52-gene panel. P-values calculated by use of logrank test.

(FIG. 14A) OS levels of the MSK-TMB patients with high (≥10) and low (<10) TMB values. HR=0.71 (95% [CI]:0.52-0.94). (FIG. 14B) OS levels in ICB treated MSK-TMB NSCLC patients with TMB-H (≥10) and TMB-L (<10) further stratified according to groups with no compound (NC) or with compound mutation signature (C). P-values calculated by use of logrank test.

(FIG. 15A) PD-L1 expression levels in NSCLC patients with different mutation signatures. (FIG. 15B) OS levels of patients stratified according to their PD-L1 expression levels and mutation signature status. PL-NC: PD-L1 level low (<1%), no compound signature; PH-NC, PD-L1 high (≥1%), no compound signature; PL-C, PD-L1 low (<1%), compound signature; PH-C, PD-L1 high (≥1%,) compound mutation signature. P-values calculated by use of unpaired t-test (FIG. 16A) or logrank test (FIG. 16B).

(FIG. 16A) Recruitment scores for CD8+ T cells; 95% confidence intervals [CI]: Wt 0.61 to 1.05, single 0.78 to 1.28, compound 1.04 to 1.37. (FIG. 16B) Recruitment scores for NK cells; 95% CI: Wt 0.72 to 1.21, single 0.98 to 1.56, compound 1.31 to 1.70. (FIG. 17C) Recruitment scores for eosinophils; 95% CI: Wt 0.92 to −0.63, single 0.76 to −0.46, compound −0.57 to −0.36. (FIG. 17D) Recruitment scores for Treg cells; 95% CI: Wt 1.00 to −0.68, single 1.00 to −0.68, compound 1.17 to −0.93. P-values calculated by use of t-test (unpaired, two-tailed). Wt: 139 patients with no mutations in the 52 gene panel; single: 119 patients with only a single gene mutation in the 52-gene panel; compound: 243 patients a compound mutation signature in the 52-gene panel. Median, lower and upper quartile, minimum and maximum values were shown in the box and whisker plots.

(FIG. 17A) OS of 260 ICB-treated MSK-TMB NSCLC patients with different smoking history. Prev/curr vs never: Hazard ratio (HR)=1.10 (95% confidence interval [CI]: 0.73-1.67). (FIG. 17B) PFS of 156 ICB-treated NSCLC with different smoking history. Prev/curr vs never: Hazard ratio (HR)=0.77 (95% confidence interval [CI]: 0.48-1.27). P-values calculated by use of logrank test.

DETAILED DESCRIPTION

Figure 1A:
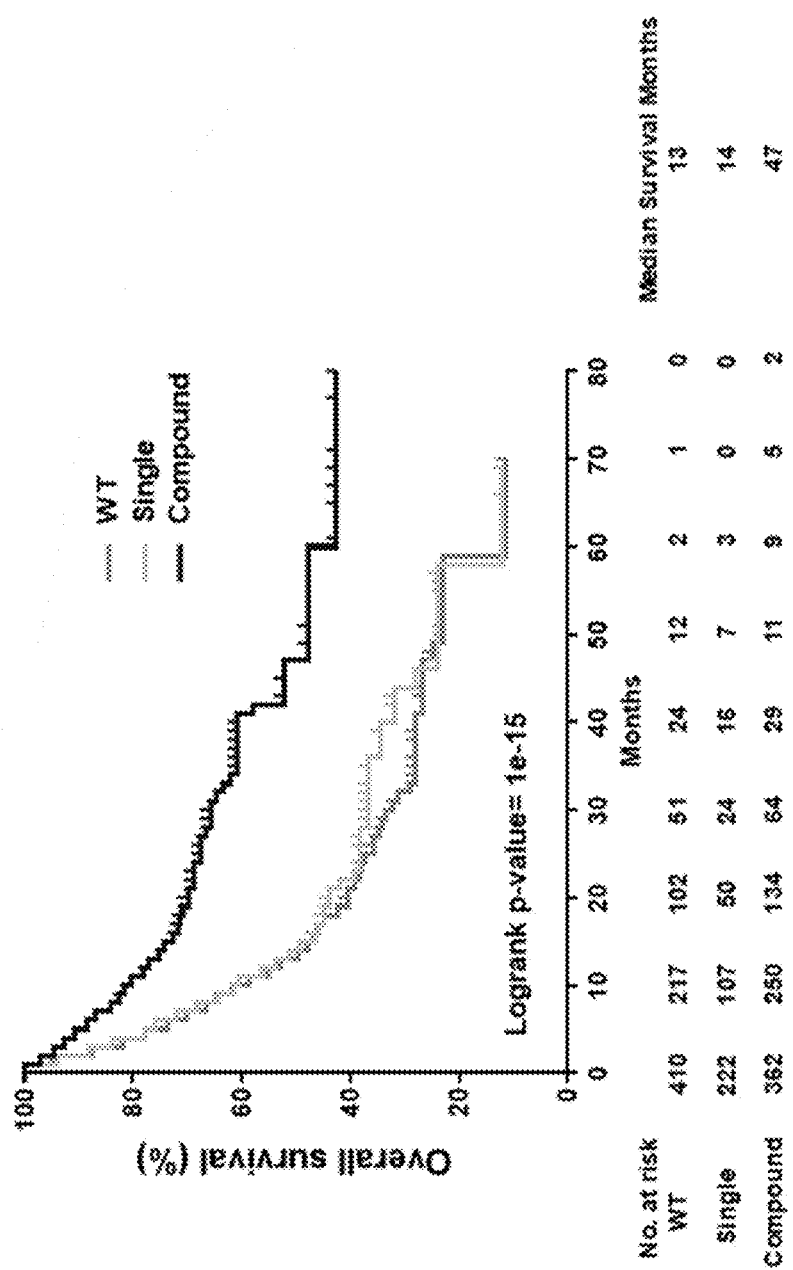
FIGS. 1A-1E are Kaplan-Meier survival curves of immune checkpoint inhibitor treated Memorial Sloan Kettering-Tumor mutational burden (MSK-TMB) cancer patients with different gene mutation patterns in a 42-gene panel in accordance with an embodiment of the present disclosure.

The following description recites various aspects and embodiments of the present compositions and methods. No particular embodiment is intended to define the scope of the compositions and methods. Rather, the embodiments merely provide non-limiting examples of various compositions and methods that are at least included within the scope of the disclosed compositions and methods. The description is to be read from the perspective of one of ordinary skill in the art; therefore, information well known to the skilled artisan is not necessarily included.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of and "consisting of those certain elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

While various immune checkpoint blockade (ICB) therapies are known and in use, there are few useful biomarkers for identifying patients responsive to such therapies. The most widely used biomarker for ICB therapy is PD-L1. Both first-line and second-line pembrolizumab treatment of NSCLC was approved by the U.S. Food and Drug Administration (FDA) based on PD-L1 expression in tumor cells. However, other ICB agents such as nivolumab, atezolizumab, and durvalumab showed significant clinical benefits in NSCLC treatment without requirement for specific PD-L1 levels. In the first line setting, nivolumab did not improve progression-free survival (PFS) in patients with high PD-L1. Thus, PD-L1 level has so far been inconsistent in predicting ICB efficacy.

Another established genetic predictor of tumor response to ICB treatment is MSI (microsatellite instability). Microsatellite instability occurs in a subset of malignancies because of deficiencies in mismatch repair genes. MSI+ tumors were associated with significantly better response to ICB therapy. As such, MSI+ status has been approved as a clinical biomarker for ICB therapy irrespective of tumor origin. The utility of MSI+ status as a biomarker for ICB therapy was consistent with the idea that neoantigens were responsible for positive responses to immunotherapy. MSI+ status as a biomarker is based on the premise that more mutations in the genome of a cancer cell were more likely to generate more tumor-specific neoantigens that could promote CD8+ T cell mediated tumor cell killing. Based on this concept, tumors without clear evidence of MSI but that nonetheless had high levels of tumor mutational burden (TMB) were examined for their responses to ICB therapy. Indeed, it was demonstrated that within many different types of cancer, high TMB predicted for better response to ICB therapy in multiple cancer types. However, compared to MSI status, TMB as a biomarker for ICB treatment has been difficult to implement because high or low TMB is relative for each tumor type and the cut-offs appeared to be different for various types of cancers. Despite these issues, the US FDA recently approved pembrolizumab treatment of adult and pediatric solid tumors with high TMB (TMB-H) (≥10). However, given ambiguities in previous studies, high TMB may not accurately predict responsiveness to ICB therapy.

As shown herein, the inventors discovered that gene mutations in immunotherapy genes could positively influence ICB treatment efficacy. In one example, genes were identified by investigating a population of NSCLC patients from a recently published cohort of ICB-treated patients. The genomic sequences from patients were sequenced with a targeted sequencing panel which contained around 400 genes known to be involved in cancer development. To compile the list of candidate genes 1) the gene had to be mutated in at least 3 or more cancer patients; 2) mutations in the gene had to be correlated with a survival benefit, e.g. its mutation frequency has to be significantly higher among the surviving patients (at the end of clinical observation period) than that among the deceased patients (with a p value≤0.10 instead of p<0.05 due to small number of patients for some genes). Applying these criteria to the targeted sequencing gene panel used in the study, a 52 gene panel (ABL1, ASXL1, ATM, BCOR, BRCA2, BRIP1, CARD11, CD79B, CDC73, CIC, EPHA3, EPHA5, EPHA, EPHB1, ERBB4, ERCC4, FGFR4, FLT3, FOXL2, HGF, INHBA, JAK3, MAX, MDC1, MED12, MET, MGA, MRE11, MSH2 NF2, NFKBIA, NOTCH1, NOTCH2, NTRK3, NUF, PARP1, PAX5, PGR, PIK3C2G, PIK3C3, PIK3CG, PIM1, POLE PPM1D, PPP2R1A, PTPRD, RET, STAT3, TENT, TET1, TSC2, and ZFHX3) was obtained.

Using this exemplary panel, identification of one or more mutations in two or more genes associated with responsiveness to ICB therapy could predict ICB efficacy better than TMB.

At present, the most commonly used biomarker to select for ICB patients is PD-L1 expression. However, it is subject to challenges in tissue sample acquisition, preservation, preparation, and ambiguities in its predictive value. In comparison, compound mutation identification is a straightforward process that can be achieved with different platform technologies, including archival FFPE tissues and liquid biopsies such as patients' blood, saliva, or urine samples. It is also amenable for analysis using DNA from CTCs (circulating tumor cells), ctDNAs (circulating tumor DNAs), or cfDNAs (circulating free DNAs). Therefore, the compound mutation signature is much easier to implement clinically as a biomarker.

Provided herein are methods for treating cancer in a subject. The methods comprise (a) identifying one or more mutations in two or more genes associated with responsiveness to immune checkpoint blockade (ICB) therapy, in a biological sample from a subject having cancer, wherein the presence of one or more mutations in the two or more genes associated with responsiveness to ICB indicates the subject is responsiveness to ICB therapy; and (b) administering an ICB therapy to the subject having cancer that is responsive to ICB therapy.

Also provided is a method for treating cancer in a subject comprising administering an ICB therapy to a subject having cancer, wherein the subject's cancer comprises one or more mutations in two or more genes two or more genes associated with responsiveness to ICB. In some embodiments, the subject's cancer comprises one or more mutations in two or more genes associated with responsiveness to ICB, wherein the two or more genes are selected from the group consisting of ABL1, ASXL1, ATM, BCOR, BRCA2, BRIP1, CARD11, CD79B, CDC73, CIC, EPHA3, EPHA5, EPHA, EPHB1, ERBB4, ERCC4, FGFR4, FLT3, FOXL2, HGF, INHBA, JAK3, MAX, MDC1, MED12, MET, MGA, MRE11, MSH2 NF2, NFKBIA, NOTCH1, NOTCH2, NTRK3, NUF, PARP1, PAX5, PGR, PIK3C2G, PIK3C3, PIK3CG, PIM1, POLE PPM1D, PPP2R1A, PTPRD, RET, STAT3, TENT, TET1, TSC2, and ZFHX3. In some embodiments, the subject's cancer comprises one or more mutations in two or more genes associated with responsiveness to ICB, wherein the two or more genes are selected from the group consisting of ABL1, ALK, ATM, BRCA1, BTK, CARM1, CREBBP, CTCF, CYLD, DNMT1, DNMT3A, DROSHA, EPHAS, EPHA7, EPHB1, ERBB3, FAT1, FBXW7, FGFR2, FGFR4, FLT3, KDR, LYN, MAX, MSI1, NCOA3, NCOR1, NF2, NOTCH3, NTRK3, NUF2, PALB2, PPM1D, PREX2, PTPRD, RNF43, ROS1, SHOC2, SMO, STAT5B, TET1, and ZFHX3.

In some embodiments, the cancer is selected from the group consisting of non-small cell lung cancer (NSCLC), bladder cancer, skin cancer (for example, melanoma), renal cell carcinoma, colorectal cancer, esophagastric cancer, head and neck cancer, glioma, and breast cancer.

In some embodiments, the cancer is NSCLC and the method comprises: (a) identifying one or more mutations in two or more genes selected from the group consisting of ABL1, ASXL1, ATM, BCOR, BRCA2, BRIP1, CARD11, CD79B, CDC73, CIC, EPHA3, EPHA5, EPHA, EPHB1, ERBB4, ERCC4, FGFR4, FLT3, FOXL2, HGF, INHBA, JAK3, MAX, MDC1, MED12, MET, MGA, MRE11, MSH2 NF2, NFKBIA, NOTCH1, NOTCH2, NTRK3, NUF, PARP1, PAX5, PGR, PIK3C2G, PIK3C3, PIK3CG, PIM1, POLE PPM1D, PPP2R1A, PTPRD, RET, STAT3, TENT, TET1, TSC2, and ZFHX3 in a biological sample from the subject having NSCLC, wherein the presence of one or more mutations in the two or more genes indicates the subject is responsive to ICB therapy; and (b) administering ICB therapy to the subject having NSCLC that is responsive to ICB therapy.

In some embodiments, the cancer is NSCLC and the method comprises the method comprises: (a) identifying one or more mutations in the ABL1, ASXL1, ATM, BCOR, BRCA2, BRIP1, CARD11, CD79B, CDC73, CIC, EPHA3, EPHA5, EPHA, EPHB1, ERBB4, ERCC4, FGFR4, FLT3, FOXL2, HGF, INHBA, JAK3, MAX, MDC1, MED12, MET, MGA, MRE11, MSH2 NF2, NFKBIA, NOTCH1, NOTCH2, NTRK3, NUF, PARP1, PAX5, PGR, PIK3C2G, PIK3C3, PIK3CG, PIM1, POLE, PPM1D, PPP2R1A, PTPRD, RET, STAT3, TENT, TET1, TSC2, and ZFHX3 genes in a biological sample from the subject, wherein the presence of one or more mutations in two or more genes indicates the subject is responsive to ICB therapy; and (b) administering ICB therapy to the subject that is responsive to ICB therapy. In some methods, the cancer is selected from the group consisting of NSCLC, bladder cancer, melanoma and colorectal cancer, wherein the subject one or more mutations in two or more genes selected from the group consisting of ABL1, ALK, ATM, BRCA1, BTK, CARM1, CREBBP, CTCF, CYLD, DNMT1, DNMT3A, DROSHA, EPHAS, EPHA7, EPHB1, ERBB3, FAT1, FBXW7, FGFR2, FGFR4, FLT3, KDR, LYN, MAX, MSI1, NCOA3, NCOR1, NF2, NOTCH3, NTRK3, NUF2, PALB2, PPM1D, PREX2, PTPRD, RNF43, ROS1, SHOC2, SMO, STAT5B, TET1, and ZFHX3 are identified in the subject. In some methods, the cancer is selected from the group consisting of NSCLC, bladder cancer, melanoma and colorectal cancer, and the method comprises identifying one or more mutations in the ABL1, ALK, ATM, BRCA1, BTK, CARM1, CREBBP, CTCF, CYLD, DNMT1, DNMT3A, DROSHA, EPHAS, EPHA7, EPHB1, ERBB3, FAT1, FBXW7, FGFR2, FGFR4, FLT3, KDR, LYN, MAX, MSI1, NCOA3, NCOR1, NF2, NOTCH3, NTRK3, NUF2, PALB2, PPM1D, PREX2, PTPRD, RNF43, ROS1, SHOC2, SMO, STAT5B, TET1, and ZFHX3 genes in a biological sample from the subject.

In some embodiments, the cancer is NSCLC and the method comprises: (a) identifying one or more mutations in two or more genes selected from the group consisting of ABL1, ALK, ASXL1, ASXL2, ATM, AXIN2, BCOR, BRCA2, BRIP1, CARD11, CARM1, CD79B, CDC73, CIC, DDR2, DNAJB1, EPHA3, EPHA5, EPHA7, EPHB1, ERBB4, ERCC4, FGFR4, FLT3, FOXL2, HGF, IL7R, INHA, INHBA, IRS2, JAK3, KMT2A, KMT2C, LATS1, MAX, MDC1, MED12, MET, MGA, MRE11, MSH2, NF2, NFKBIA, NKX2-1, NOTCH1, NOTCH2, NTRK3, NUF2, PARP1, PAX5, PGR, PIK3C2G, PIK3C3, PIK3CG, PIM1, POLE, PPM1D, PPP2R1A, PTPRD, RET, SF3B1, STAT3, STAT5B, TENT5C, TERT, TET1, TSC2, and ZFHX3 in a biological sample from the subject having NSCLC, wherein the presence of one or more mutations in the two or more genes indicates the subject is responsive to ICB therapy; and (b) administering ICB therapy to the subject having NSCLC that is responsive to ICB therapy.

In some embodiments, the cancer is NSCLC and the method comprises: (a) identifying one or more mutations in the ABL1, ALK, ASXL1, ASXL2, ATM, AXIN2, BCOR, BRCA2, BRIP1, CARD11, CARM1, CD79B, CDC73, CIC, DDR2, DNAJB1, EPHA3, EPHA5, EPHA7, EPHB1, ERBB4, ERCC4, FGFR4, FLT3, FOXL2, HGF, IL7R, INHA, INHBA, IRS2, JAK3, KMT2A, KMT2C, LATS1, MAX, MDC1, MED12, MET, MGA, MRE11, MSH2, NF2, NFKBIA, NKX2-1, NOTCH1, NOTCH2, NTRK3, NUF2, PARP1, PAX5, PGR, PIK3C2G, PIK3C3, PIK3CG, PIM1, POLE, PPM1D, PPP2R1A, PTPRD, RET, SF3B1, STAT3, STAT5B, TENT5C, TERT, TET1, TSC2, and ZFHX3 genes in a biological sample from the subject, wherein the presence of one or more mutations in two or more genes indicates the subject is responsive to ICB therapy; and (b) administering ICB therapy to the subject having NSCLC that is responsive to ICB therapy.

In some embodiments, the cancer is NSCLC and the method comprises: (a) identifying one or more mutations in two or more genes selected from the group consisting of ABL1, ACVR1, BBC3, BCL2L1, BCL6, CARM1, CCNE1, CD274, CD74, CD79B, CDC73, CDKN1A, CHEK1, CRLF2, CSF1R, CTLA4, CYSLTR2, DCUN1D1, DHFRP3, DNAH2, DNAJB1, E2F3, EED, EGFL7, ENSA, EPHA7, ERCC3, ERCC4, ERRFI1, ETV1, FBRSL1, FGFR4, FLCN, FLT3, FOXL2, GNAQ, HIST1H3E, HIST1H3H, HIST3H3, IKZF1, INHA, JUN, KNSTRN, MAPKAP1, MAX, MDM4, MRE11, MSH2, MSH3, MYCL, NF2, NFKBIA, NKX3-1, NRG1, NTRK3, NUF2, ONECUT1, PARP1, PAX5, PDPK1, PIK3CD, PIK3CD, PIM1, PPM1D, PPP2R1A, PRDM1, RAC2, RAD50, RAD51B, RAD51C, REL, RRAGC, RYBP, SDHAF2, SDHAP3, SLC34A2, STAT3, STAT5B, TAP2, TENT5C, TET1, and ZFHX3 in a biological sample from the subject having NSCLC, wherein the presence of one or more mutations in the two or more genes indicates the subject is responsive to ICB therapy; and (b) administering ICB therapy to the subject having NSCLC that is responsive to ICB therapy.

In some embodiments, the cancer is NSCLC and the method comprises: (a) identifying one or more mutations in the ABL1, ACVR1, BBC3, BCL2L1, BCL6, CARM1, CCNE1, CD274, CD74, CD79B, CDC73, CDKN1A, CHEK1, CRLF2, CSF1R, CTLA4, CYSLTR2, DCUN1D1, DHFRP3, DNAH2, DNAJB1, E2F3, EED, EGFL7, ENSA, EPHA7, ERCC3, ERCC4, ERRFI1, ETV1, FBRSL1, FGFR4, FLCN, FLT3, FOXL2, GNAQ, HIST1H3E, HIST1H3H, HIST3H3, IKZF1, INHA, JUN, KNSTRN, MAPKAP1, MAX, MDM4, MRE11, MSH2, MSH3, MYCL, NF2, NFKBIA, NKX3-1, NRG1, NTRK3, NUF2, ONECUT1, PARP1, PAX5, PDPK1, PIK3C3, PIK3CD, PIM1, PPM1D, PPP2R1A, PRDM1, RAC2, RAD50, RAD51B, RAD51C, REL, RRAGC, RYBP, SDHAF2, SDHAP3, SLC34A2, STAT3, STAT5B, TAP2, TENT5C, TET1, and ZFHX3 genes in a biological sample from the subject, wherein the presence of one or more mutations in two or more genes indicates the subject is responsive to ICB therapy; and (b) administering ICB therapy to the subject having NSCLC that is responsive to ICB therapy.

In some embodiments, the cancer is NSCLC and the method comprises: (a) identifying one or more mutations in ABL1, ALK, ATM, BRCA1, BTK, CARM1, CREBBP, CTCF, CYLD, DNMT1, DNMT3A, DROSHA, EPHAS, EPHA7, EPHB1, ERBB3, FAT1, FBXW7, FGFR2, FGFR4, FLT3, KDR, LYN, MAX, MSI1, NCOA3, NCOR1, NF2, NOTCH3, NTRK3, NUF2, PALB2, PPM1D, PREX2, PTPRD, RNF43, ROS1, SHOC2, SMO, STAT5B, TET1, and ZFHX3 genes in a biological sample from the subject having NSCLC, wherein the presence of one or more mutations in two or more genes indicates the subject is responsive to ICB therapy; and (b) administering ICB therapy to the subject having NSCLC that is responsive to ICB therapy.

In some embodiments, the cancer is NSCLC and the method comprises (a) identifying one or more mutations in two or more genes selected from the group consisting of ABL1, ALK, ATM, BRCA1, BTK, CARM1, CREBBP, CTCF, CYLD, DNMT1, DNMT3A, DROSHA, EPHAS, EPHA7, EPHB1, ERBB3, FAT1, FBXW7, FGFR2, FGFR4, FLT3, KDR, LYN, MAX, MSI1, NCOA3, NCOR1, NF2, NOTCH3, NTRK3, NUF2, PALB2, PPM1D, PREX2, PTPRD, RNF43, ROS1, SHOC2, SMO, STAT5B, TET1, and ZFHX3 in a biological sample from the subject having NSCLC, wherein the presence of one or more mutations in the two or more genes indicates the subject is responsive to ICB therapy; and (b) administering ICB therapy to the subject having NSCLC that is responsive to ICB therapy.

In some embodiments, the cancer is melanoma and the method comprises: (a) identifying one or more mutations in two or more genes selected from the group consisting of ACVR1, AKT1, AMER1, APC, ARID1A, ATR, ATRX, BCOR, BIRC3, BRAF, BTK, CARD11, CASP8, CIC, CSDE1, CUL3, CYLD, DNMT3A, DOT1L, DROSHA, EGFR, ELF3, EPHA7, ERBB4, ERG, ETV1, EZH2, FANCA, FANCC, FAT1, FLT3, FLT4, GPS2, GRIN2A, HGF, HIST1H3B, HOXB13, IDH1, IGF1R, IL7R, INHBA, INSR, IRF4, JAK2, KDM5A, KDR, KMT2A, KMT2C, KMT2D, KNSTRN, LYN, MALT1, MAPK3, MED12, MET, MPL, MSH2, MSH3, MSI1, MST1R, MTOR, MYCL, NCOA3, NF1, NF2, NOTCH3, NSD1, NTRK1, NTRK2, NTRK3, NUP93, PAK5, PARP1, PBRM1, PGR, PHOX2B, PIK3CA, PIM1, PLCG2, PMS2, PREX2, PRKCI, PRKD1, PTPRD, PTPRT, RAB35, RET, RICTOR, ROS1, RPTOR, SETD2, SHOC2, STAG2, STAT3, STAT5A, TAP2, TEK, TENT5C, TERT, TET1, TP53, TP53BP1, and ZFHX3 in a biological sample from the subject having melanoma, wherein the presence of one or more mutations in the two or more genes indicates the subject is responsive to ICB therapy; and (b) administering ICB therapy to the subject having melanoma that is responsive to ICB therapy.

In some embodiments, the cancer is melanoma and the method comprises: (a) identifying one or more mutations in the ACVR1, AKT1, AMER1, APC, ARID1A, ATR, ATRX, BCOR, BIRC3, BRAF, BTK, CARD11, CASP8, CIC, CSDE1, CUL3, CYLD, DNMT3A, DOT1L, DROSHA, EGFR, ELF3, EPHA7, ERBB4, ERG, ETV1, EZH2, FANCA, FANCC, FAT1, FLT3, FLT4, GPS2, GRIN2A, HGF, HIST1H3B, HOXB13, IDH1, IGF1R, IL7R, INHBA, INSR, IRF4, JAK2, KDM5A, KDR, KMT2A, KMT2C, KMT2D, KNSTRN, LYN, MALT1, MAPK3, MED12, MET, MPL, MSH2, MSH3, MSI1, MST1R, MTOR, MYCL, NCOA3, NF1, NF2, NOTCH3, NSD1, NTRK1, NTRK2, NTRK3, NUP93, PAK5, PARP1, PBRM1, PGR, PHOX2B, PIK3CA, PIM1, PLCG2, PMS2, PREX2, PRKCI, PRKD1, PTPRD, PTPRT, RAB35, RET, RICTOR, ROS1, RPTOR, SETD2, SHOC2, STAG2, STAT3, STAT5A, TAP2, TEK, TENT5C, TERT, TET1, TP53, TP53BP1, and ZFHX3 genes in a biological sample from the subject, wherein the presence of one or more mutations in two or more genes indicates the subject is responsive to ICB therapy; and (b) administering ICB therapy to the subject having melanoma that is responsive to ICB therapy.

In some embodiments, the cancer is melanoma and the method comprises: (a) identifying one or more mutations in two or more genes selected from the group consisting of ACVR1, AKT1, AKT3, API5, ATP10A, ATR, AURKB, BABAM1, BASP1-AS1, BBC3, BCL2, BCL2L1, BCL2L11, BCL2L14, BIRC3, BTK, CASP8, CBX4, CCND2, CCNE1, CCNQ, CD276, CDK5RAP2, CDKN2C, CENPA, CNTROB, CSDE1, CUL3, CYLD, CYSLTR2, DNAH1, DNMT3A, DROSHA, DUSP4, EGFL7, EIF4A2, EIF5A, ELF3, EPAS1, ETV1, EZH2, FANCA, FANCC, FGF4, FMN1, FOXA1, GATA2, GCDH, GPS2, GRIA1, H3F3A, HIST1H2BDHIST1H3B, HIST1H3F, HIST1H3G, HIST1H3I, HOXB13, IDH2, IGF2, ILVBL, INHBA, INSRR, IP6K1, IRF4, JAK2, KCND2, KEAP1, KIAA1549, KNSTRN, LINC00244, LMO1, LMO3, LYN, LZTS1, MALT1, MAPK1, MAPK3, MAX, METTL2B, MSH2, MSH3, MSI1, MSI2, MST1, MYC, MYCL, MYOD1, NAB2, NCOA3, NF2, NFKBIA, NKX3-1, NSD3, NUP93, PAK1, PIK3R3, PIM1, PLK2, PMS2, PNPLA6, PNRC1, PPFIA2, PPP2R1A, PREX2, PRKCA, PRKCI, PRKD1, PRR5-ARHGAP8, RAB35, RAD51, RAD51D, RAD54L, RASA1, RICTOR, RIT1, RRAS2, RXRA, SDHAF2, SDHB, SDHC, SDHD, SESN2, SESN3, SH3BGRL, SH3GL2, SHOC2, SLC41A3, SLX4, SMARCD1, SOS1, SPG7, SPRED1, SRP19, STAG2, STAT3, STAT5A, STK11, STRN, STX7, TAP2, TEK, TENT5C, TET1, TMEM127, TMTC2, TP53BP1, UPF1, VEGFC, XRCC2, ZNF664, and ZRSR2 in a biological sample from the subject having melanoma, wherein the presence of one or more mutations in the two or more genes indicates the subject is responsive to ICB therapy; and (b) administering ICB therapy to the subject having melanoma that is responsive to ICB therapy.

In some embodiments, the cancer is melanoma and the method comprises: (a) identifying one or more mutations in the ACVR1, AKT1, AKT3, API5, ATP10A, ATR, AURKB, BABAM1, BASP1-AS1, BBC3, BCL2, BCL2L1, BCL2L11, BCL2L14, BIRC3, BTK, CASP8, CBX4, CCND2, CCNE1, CCNQ, CD276, CDK5RAP2, CDKN2C, CENPA, CNTROB, CSDE1, CUL3, CYLD, CYSLTR2, DNAH1, DNMT3A, DROSHA, DUSP4, EGFL7, EIF4A2, EIF5A, ELF3, EPAS1, ETV1, EZH2, FANCA, FANCC, FGF4, FMN1, FOXA1, GATA2, GCDH, GPS2, GRIA1, H3F3A, HIST1H2BDHIST1H3B, HIST1H3F, HIST1H3G, HIST1H3I, HOXB13, IDH2, IGF2, ILVBL, INHBA, INSRR, IP6K1, IRF4, JAK2, KCND2, KEAP1, KIAA1549, KNSTRN, LINC00244, LMO1, LMO3, LYN, LZTS1, MALT1, MAPK1, MAPK3, MAX, METTL2B, MSH2, MSH3, MSI1, MSI2, MST1, MYC, MYCL, MYOD1, NAB2, NCOA3, NF2, NFKBIA, NKX3-1, NSD3, NUP93, PAK1, PIK3R3, PIM1, PLK2, PMS2, PNPLA6, PNRC1, PPFIA2, PPP2R1A, PREX2, PRKCA, PRKCI, PRKD1, PRR5-ARHGAP8, RAB35, RAD51, RAD51D, RAD54L, RASA1, RICTOR, RIT1, RRAS2, RXRA, SDHAF2, SDHB, SDHC, SDHD, SESN2, SESN3, SH3BGRL, SH3GL2, SHOC2, SLC41A3, SLX4, SMARCD1, SOS1, SPG7, SPRED1, SRP19, STAG2, STAT3, STAT5A, STK11, STRN, STX7, TAP2, TEK, TENT5C, TET1, TMEM127, TMTC2, TP53BP1, UPF1, VEGFC, XRCC2, ZNF664, and ZRSR2 genes in a biological sample from the subject, wherein the presence of one or more mutations in two or more genes indicates the subject is responsive to ICB; and (b) administering ICB therapy to the subject having melanoma that is responsive to ICB therapy.

In some embodiments, the cancer is bladder cancer and the method comprises: (a) identifying one or more mutations in two or more genes selected from the group consisting of AGO2, AKT2, ALK, ANKRD11, AR, ARAF, ARID1B, ATM, ATRX, AXL, BCL6, BLM, BRIP1, CDKN1A, CDKN2A, CIC, CREBBP, CTCF, CTNNB1, DNMT1, DNMT3A, EP300, EPHA5, EPHB1, ERBB3, ESR1, FAT1, FGFR1, FGFR2, FOXP1, IGF1, IKZF1, JAK1, JAK2, KDR, KMT2A, KRAS, LATS1, LATS2, MAP2K1, MAP3K1, MCL1, MED12, MITF, MSH2, MSH3, MSH6, MST1R, NCOA3, NCOR1, NOTCH2, NTRK3, PALB2, PAX5, PIK3CB, PIK3CG, PLK2, PPARG, PPM1D, PRDM1, PRKCI, PTCH1, PTPRD, RAF1, RET, RNF43, SESN2, SETD2, SLX4, SMARCA4, SOS1, SPOP, SRC, STAG2, STAT5B, TCF7L2, TEK, TOP1, TP53, TSC2, U2AF1, WWTR1, XPO1, YAP1, and ZFHX3 in a biological sample from the subject having NSCLC, wherein the presence of one or more mutations in the two or more genes indicates the subject is responsive to ICB therapy; and (b) administering ICB therapy to the subject having bladder cancer that is responsive to ICB therapy.

In some embodiments, the cancer is bladder cancer, wherein the method comprises: (a) identifying one or more mutations in the AGO2, AKT2, ALK, ANKRD11, AR, ARAF, ARID1B, ATM, ATRX, AXL, BCL6, BLM, BRIP1, CDKN1A, CDKN2A, CIC, CREBBP, CTCF, CTNNB1, DNMT1, DNMT3A, EP300, EPHA5, EPHB1, ERBB3, ESR1, FAT1, FGFR1, FGFR2, FOXP1, IGF1, IKZF1, JAK1, JAK2, KDR, KMT2A, KRAS, LATS1, LATS2, MAP2K1, MAP3K1, MCL1, MED12, MITF, MSH2, MSH3, MSH6, MST1R, NCOA3, NCOR1, NOTCH2, NTRK3, PALB2, PAX5, PIK3CB, PIK3CG, PLK2, PPARG, PPM1D, PRDM1, PRKCI, PTCH1, PTPRD, RAF1, RET, RNF43, SESN2, SETD2, SLX4, SMARCA4, SOS1, SPOP, SRC, STAG2, STAT5B, TCF7L2, TEK, TOP1, TP53, TSC2, U2AF1, WWTR1, XPO1, YAP1, and ZFHX3 genes in a biological sample from the subject, wherein the presence of one or more mutations in two or more genes indicates the subject is responsive to ICB therapy; and (b) administering ICB therapy to the subject having bladder cancer that is responsive to ICB therapy.

In some embodiments, the cancer is bladder cancer and the method comprises: (a) identifying one or more mutations in two or more genes selected from the group consisting of AGO2, AKT2, ALK, AR, ARAF, ATM, ATPSCKMT, AXL, BCL6, BLM, BRIP1, CASC15, CCND1, CCND3, CCNE1, CDC73, CDK4, CDK6, CDKN1B, CEBPA, CENPA, CHRNA6, CRLF2, CSDE1, CTCF, CTNNBL1, CXCR4, CYSLTR2, DCUN1D1, DNMT1, DNMT3A, EIF4E, EPHA5, ERCC4, ESR1, FGF3, FGFR1, FGFR2, FGFR4, FH, FIP1L1, FOXL2, FOXO1, FRAT2, GATA1, GREM1, GSK3B, HIST1H3A, HIST1H3E, HIST1H3H, HLA-A, HNF1A, IDH1, IDH2, IGF1, IGF2, IKBKE, IL10, IL7R, INHA, INPP4A, IQSEC1, JAK1, JAK2, KDR, KEAP1, KIF1B, KMT2B, KRAS, LATS1, LRP1B, LYN, MAP2K1, MAP3K1, MAPKBP1, MCL1, MDM4, MED12, MET, MITF, MPL, MSH2, MSH3, MSH6, MST1, MST1R, MYCN, NCOA3, NCOR1, NFKBIA, NOTCH2, NSD3, NTRK3, NUP93, PAFAH1B3, PALB2, PAX5, PDPK1, PELI2, PIM1, PNRC1, PPM1D, PPP2R1A, PPP6C, PRDM1, PRKAR1A, PRKCI, PTPN11, PTPRD, PVALEF, RAD51C, RARA, RASL12, RET, RIT1, RNF43, SDHA, SDHB, SESN2, SESN3, SHOC2, SLX4, SMAD4, SMARCD1, SOS1, SPOP, SRC, SRSF2, STAT5B, SUZ12, TAP2, TCF3, TCF7L2, TEK, TNFRSF14, TNFSF12, TRAF2, U2AF1, VEGFA, WWTR1, XPO1, YAP1, ZNF157, and ZRSR2 in a biological sample from the subject having bladder cancer, wherein the presence of one or more mutations in the two or more genes indicates the subject is responsive to ICB therapy; and (b) administering ICB therapy to the subject having bladder cancer that is responsive to ICB therapy.

In some embodiments, the cancer is bladder cancer, wherein the method comprises: (a) identifying one or more mutations in the AGO2, AKT2, ALK, AR, ARAF, ATM, ATPSCKMT, AXL, BCL6, BLM, BRIP1, CASC15, CCND1, CCND3, CCNE1, CDC73, CDK4, CDK6, CDKN1B, CEBPA, CENPA, CHRNA6, CRLF2, CSDE1, CTCF, CTNNBL1, CXCR4, CYSLTR2, DCUN1D1, DNMT1, DNMT3A, EIF4E, EPHA5, ERCC4, ESR1, FGF3, FGFR1, FGFR2, FGFR4, FH, FIP1L1, FOXL2, FOXO1, FRAT2, GATA1, GREM1, GSK3B, HIST1H3A, HIST1H3E, HIST1H3H, HLA-A, HNF1A, IDH1, IDH2, IGF1, IGF2, IKBKE, IL10, IL7R, INHA, INPP4A, IQSEC1, JAK1, JAK2, KDR, KEAP1, KIF1B, KMT2B, KRAS, LATS1, LRP1B, LYN, MAP2K1, MAP3K1, MAPKBP1, MCL1, MDM4, MED12, MET, MITF, MPL, MSH2, MSH3, MSH6, MST1, MST1R, MYCN, NCOA3, NCOR1, NFKBIA, NOTCH2, NSD3, NTRK3, NUP93, PAFAH1B3, PALB2, PAX5, PDPK1, PELI2, PIM1, PNRC1, PPM1D, PPP2R1A, PPP6C, PRDM1, PRKAR1A, PRKCI, PTPN11, PTPRD, PVALEF, RAD51C, RARA, RASL12, RET, RIT1, RNF43, SDHA, SDHB, SESN2, SESN3, SHOC2, SLX4, SMAD4, SMARCD1, SOS1, SPOP, SRC, SRSF2, STAT5B, SUZ12, TAP2, TCF3, TCF7L2, TEK, TNFRSF14, TNFSF12, TRAF2, U2AF1, VEGFA, WWTR1, XPO1, YAP1, ZNF157, and ZRSR2 genes in a biological sample from the subject, wherein the presence of one or more mutations in two or more genes indicates the subject is responsive to ICB therapy; and (b) administering ICB therapy to the subject having bladder cancer that is responsive to ICB therapy.

In some embodiments, the cancer is renal cell carcinoma and the method comprises: (a) identifying one or more mutations in two or more genes selected from the group consisting of ARID1B, BBC3, BRD4, CSF1R, DICER1, EGFR, EPHA5, ERBB2, ERCC5, KDM5C, KDR, KMT2C, KMT2D, LATS1, MAP2K1, MTOR, NBN, NOTCH1, NOTCH4, POLD1, PTPRS, RARA, ROS1, SETD2, STAG2, TET2, TP53, VEGFA, and VHL in a biological sample from the subject having NSCLC, wherein the presence of one or more mutations in the two or more genes indicates the subject is responsive to ICB therapy; and (b) administering ICB therapy to the subject having renal cell carcinoma that is responsive to ICB therapy.

In some embodiments, the cancer is renal cell carcinoma, wherein the method comprises: (a) identifying one or more mutations in the ARID1B, BBC3, BRD4, CSF1R, DICER1, EGFR, EPHA5, ERBB2, ERCC5, KDM5C, KDR, KMT2C, KMT2D, LATS1, MAP2K1, MTOR, NBN, NOTCH1, NOTCH4, POLD1, PTPRS, RARA, ROS1, SETD2, STAG2, TET2, TP53, VEGFA, and VHL genes in a biological sample from the subject, wherein the presence of one or more mutations in two or more genes indicates the subject is responsive to ICB therapy; and (b) administering ICB therapy to the subject having renal cell carcinoma that is responsive to ICB therapy.

In some embodiments, the cancer is renal cell carcinoma and the method comprises: (a) identifying one or more mutations in two or more genes selected from the group consisting of ACVR1, ALOX12B, ANKRD11, ARID5B, ATR, AURKA, AURKB, BBC3, BRD4, BTK, CALR, CARD11, CCNE1, CDH1, CDKN2B, CDKN2B-AS1, CSF1R, DICER1, DNMT1, DNMT3B, EGFR, EIF4A2, ELOC, EPHA5, ERBB2, ERCC5, ERRFI1, FGFR1, FGFR2, FLT4, FOXL2, FOXO1, GATA1, GATA3, GLI1, HIST1H3G, IKBKE, IL10, IL7R, KDM6A, KEAP1, KMT2C, KMT2D, KRAS, LATS1, MAP2K1, MAP3K13, MAPK3, MDM2, MLH1, MTOR, MYOD1, NBN, NCOA3, NCOR1, NKX3-1, NOTCH1, NOTCH4, PAK5, PDGFRB, PHOX2B, PIK3C2G, PIK3CB, PMS1, POLD1, PRDM1, PRKAR1A, PRKN, PTPRD, PTPRS, RAD50, RARA, RBM10, RET, RHOA, RNF43, ROS1, SMAD2, SRC, STAG2, TET2, U2AF1, VEGFA, XIAP, YAP1, and YES1 in a biological sample from the subject having renal cell carcinoma, wherein the presence of one or more mutations in the two or more genes indicates the subject is responsive to ICB therapy; and (b) administering ICB therapy to the subject having renal cell carcinoma that is responsive to ICB therapy.

In some embodiments, the cancer is renal cell carcinoma wherein the method comprises: (a) identifying one or more mutations in the ACVR1, ALOX12B, ANKRD11, ARID5B, ATR, AURKA, AURKB, BBC3, BRD4, BTK, CALR, CARD11, CCNE1, CDH1, CDKN2B, CDKN2B-AS1, CSF1R, DICER1, DNMT1, DNMT3B, EGFR, EIF4A2, ELOC, EPHA5, ERBB2, ERCC5, ERRFI1, FGFR1, FGFR2, FLT4, FOXL2, FOXO1, GATA1, GATA3, GLI1, HIST1H3G, IKBKE, IL10, IL7R, KDM6A, KEAP1, KMT2C, KMT2D, KRAS, LATS1, MAP2K1, MAP3K13, MAPK3, MDM2, MLH1, MTOR, MYOD1, NBN, NCOA3, NCOR1, NKX3-1, NOTCH1, NOTCH4, PAK5, PDGFRB, PHOX2B, PIK3C2G, PIK3CB, PMS1, POLD1, PRDM1, PRKAR1A, PRKN, PTPRD, PTPRS, RAD50, RARA, RBM10, RET, RHOA, RNF43, ROS1, SMAD2, SRC, STAG2, TET2, U2AF1, VEGFA, XIAP, YAP1, and YES1 genes in a biological sample from the subject, wherein the presence of one or more mutations in two or more genes indicates the subject is responsive to ICB therapy; and (b) administering ICB therapy to the subject having renal cell carcinoma that is responsive to ICB therapy.

In some embodiments, the cancer is colorectal cancer and the method comprises: (a) identifying one or more mutations in two or more genes selected from the group consisting of AGO2, AKT1, ALK, ALOX12B, ANKRD11, ATRX, AXIN1, BAP1, BARD1, BCOR, BMPR1A, BRAF, BRCA1, BRIP1, CASP8, CD79B, CDH1, CIC, CREBBP, CSF1R, CTCF, DICER1, DNMT1, EPHB1, ERRFI1, FANCA, FAT1, FBXW7, FGF3, FLT3, GNA11, GNAS, HNF1A, IDH1, IFNGR1, INHA, INPP4A, IRS1, JAK1, JAK3, KDM6A, KIT, KMT2B, KMT2C, LATS1, MAP2K1, MAP2K4, MAP3K13, MRE11, MSH2, MSH6, MTOR, NCOA3, NOTCH3, NOTCH4, NSD1, NSD3, NTRK1, PDCD1, PDGFRB, PPM1D, PRKAR1A, PRKD1, PTCH1, PTPRD, RAD54L, RHOA, RICTOR, RIT1, RNF43, RTEL1, SMAD4, SMO, SOX9, SPEN, SRC, SUFU, TBX3, TEK, TET1, TNFRSF14, TP63, and TSC2 in a biological sample from the subject having colorectal cancer, wherein the presence of one or more mutations in the two or more genes indicates the subject is responsive to ICB therapy; and (b) administering ICB therapy to the subject having colorectal cancer that is responsive to ICB therapy.

In some embodiments, the cancer is colorectal cancer, wherein the method comprises: (a) identifying one or more mutations in the AGO2, AKT1, ALK, ALOX12B, ANKRD11, ATRX, AXIN1, BAP1, BARD1, BCOR, BMPR1A, BRAF, BRCA1, BRIP1, CASP8, CD79B, CDH1, CIC, CREBBP, CSF1R, CTCF, DICER1, DNMT1, EPHB1, ERRFI1, FANCA, FAT1, FBXW7, FGF3, FLT3, GNA11, GNAS, HNF1A, IDH1, IFNGR1, INHA, INPP4A, IRS1, JAK1, JAK3, KDM6A, KIT, KMT2B, KMT2C, LATS1, MAP2K1, MAP2K4, MAP3K13, MRE11, MSH2, MSH6, MTOR, NCOA3, NOTCH3, NOTCH4, NSD1, NSD3, NTRK1, PDCD1, PDGFRB, PPM1D, PRKAR1A, PRKD1, PTCH1, PTPRD, RAD54L, RHOA, RICTOR, RIT1, RNF43, RTEL1, SMAD4, SMO, SOX9, SPEN, SRC, SUFU, TBX3, TEK, TET1, TNFRSF14, TP63, and TSC2 genes in a biological sample from the subject, wherein the presence of one or more mutations in two or more genes indicates the subject is responsive to ICB therapy; and (b) administering ICB therapy to the subject having colorectal cancer that is responsive to ICB therapy.

In some embodiments, the cancer is colorectal cancer and the method comprises: (a) identifying one or more mutations in two or more genes selected from the group consisting of ABRAXAS1, AGO2, AKT1, AKT3, ALOX12B, AURKA, BAP1, BARD1, BCL2, BCL2L1, BCL2L11, BCL6, BMPR1A, BRCA1, BRIP1, CARM1, CBFB, CCND1, CCNE1, CCNQ, CD274, CD276, CD79A, CD79B, CDH1, CDK4, CDK6, CDKN1A, CDKN2C, CEBPA, CHEK1, CIC, CRKL, CTCF, CUL3, CXCR4, DCUN1D1, DNMT1, EIF1AX, EPHB1, ERRFI1, FANCA, FANCC, FGF19, FGF3, FGFR1, FOXA1, GNA11, GNAS, GPS2, HIST1H1C, HIST1H3F, HIST1H3I, HNF1A, ICOSLG, ID3, IDH1, IFNGR1, IGF1, IL7R, INHA, INPP4A, IRF4, IRS1, JAK1, JAK3, KIT, KLF4, LATS1, LMNA, MAP2K1, MAP2K4, MAP3K13, MAPK1, MAPKAP1, MCL1, MRE11, MSI2, MST1, MUTYH, MYCL, MYD88, NCOA3, NEGR1, NFE2L2, NFKBIA, NKX3-1, NOTCH3, NSD3, NUF2, PIK3R2, PIM1, PLK2, PNRC1, PPM1D, PPP6C, PRKAR1A, PRKCI, PRKD1, PTPRD, RAD51C, RAD51D, RAD54L, RHEB, RHOA, RICTOR, RIT1, RNF43, RTEL1, RYBP, SDHC, SDHD, SESN1, SESN2, SH2D1A, SHQ1, SMO, SOS1, SPRED1, SRSF2, STAG2, STAT5A, STK40, SUFU, TEK, TET1, TMEM127, TMPRSS2, TP63, USP34, VEGFA, WT1, XIAP, YAP1, and ZRSR2 in a biological sample from the subject having colorectal cancer, wherein the presence of one or more mutations in the two or more genes indicates the subject is responsive to ICB therapy; and (b) administering ICB therapy to the subject having colorectal cancer that is responsive to ICB therapy.

In some embodiments, the cancer is colorectal cancer, wherein the method comprises: (a) identifying one or more mutations in the ABRAXAS1, AGO2, AKT1, AKT3, ALOX12B, AURKA, BAP1, BARD1, BCL2, BCL2L1, BCL2L11, BCL6, BMPR1A, BRCA1, BRIP1, CARM1, CBFB, CCND1, CCNE1, CCNQ, CD274, CD276, CD79A, CD79B, CDH1, CDK4, CDK6, CDKN1A, CDKN2C, CEBPA, CHEK1, CIC. CRKL, CTCF, CUL3, CXCR4, DCUN1D1, DNMT1, EIF1AX, EPHB1, ERRFI1, FANCA, FANCC, FGF19, FGF3, FGFR1, FOXA1, GNA11, GNAS, GPS2, HIST1H1C, HIST1H3F, HIST1H3I, HNF1A, ICOSLG, ID3, IDH1, IFNGR1, IGF1, IL7R, INHA, INPP4A, IRF4, IRS1, JAK1, JAK3, KIT, KLF4, LATS1, LMNA, MAP2K1, MAP2K4, MAP3K13, MAPK1, MAPKAP1, MCL1, MRE11, MSI2, MST1, MUTYH, MYCL, MYD88, NCOA3, NEGR1, NFE2L2, NFKBIA, NKX3-1, NOTCH3, NSD3, NUF2, PIK3R2, PIM1, PLK2, PNRC1, PPM1D, PPP6C, PRKAR1A, PRKCI, PRKD1, PTPRD, RAD51C, RAD51D, RAD54L, RHEB, RHOA, RICTOR, RIT1, RNF43, RTEL1, RYBP, SDHC, SDHD, SESN1, SESN2, SH2D1A, SHQ1, SMO, SOS1, SPRED1, SRSF2, STAG2, STAT5A, STK40, SUFU, TEK, TET1, TMEM127, TMPRSS2, TP63, USP34, VEGFA, WT1, XIAP, YAP1, and ZRSR2 genes in a biological sample from the subject, wherein the presence of one or more mutations in two or more genes indicates the subject is responsive to ICB therapy; and (b) administering ICB therapy to the subject having colorectal cancer that is responsive to ICB therapy.

In some embodiments, the cancer is esophagogastric cancer and the method comprises: (a) identifying one or more mutations in two or more genes selected from the group consisting of ABL1, AMER1, APC, AR, ARID1A, ATR, AXIN2, B2M, BABAM1, BCOR, BMPR1A, BRIP1, CASP8, CCNE1, CDK12, CREBBP, CTNNB1, DIS3, DNAJB1, EPAS1, EPHA3, EPHA7, ERBB3, ERCC2, ESR1, ETV6, FGF19, GNAS, HGF, HIST1H3G, HNF1A, IDH2, IL7R, INPP4B, IRS1, IRS2, JAK2, JAK3, KDM5C, KDR, KMT2B, KRAS, LATS1, MAP3K13, MTOR, NBN, NF1, NKX2-1, NOTCH2, NOTCH3, NOTCH4, NSD3, PDCD1, PDGFRB, PIK3C2G, PIK3CA, PIK3CB, PIK3CG, PMS1, PNRC1, POLD1, PPARG, PPM1D, PRDM1, PRKCI, PRKD1, PRKN, PTEN, PTPRD, RAB35, RAD50, RBM10, RET, RHOA, RNF43, RPTOR, RTEL1, RUNX1, SETD2, SMARCA4, SMARCD1, SOX2, SPEN, SUFU, TET1, TET2, TGFBR1, and TGFBR2 in a biological sample from the subject having esophagogastric cancer, wherein the presence of one or more mutations in the two or more genes indicates the subject is responsive to ICB therapy; and (b) administering ICB therapy to the subject having esophagogastric cancer that is responsive to ICB therapy.

In some embodiments, the cancer is esophagogastric cancer, wherein the method comprises: (a) identifying one or more mutations in the ABL1, AMER1, APC, AR, ARID1A, ATR, AXIN2, B2M, BABAM1, BCOR, BMPR1A, BRIP1, CASP8, CCNE1, CDK12, CREBBP, CTNNB1, DIS3, DNAJB1, EPAS1, EPHA3, EPHA7, ERBB3, ERCC2, ESR1, ETV6, FGF19, GNAS, HGF, HIST1H3G, HNF1A, IDH2, IL7R, INPP4B, IRS1, IRS2, JAK2, JAK3, KDM5C, KDR, KMT2B, KRAS, LATS1, MAP3K13, MTOR, NBN, NF1, NKX2-1, NOTCH2, NOTCH3, NOTCH4, NSD3, PDCD1, PDGFRB, PIK3C2G, PIK3CA, PIK3CB, PIK3CG, PMS1, PNRC1, POLD1, PPARG, PPM1D, PRDM1, PRKCI, PRKD1, PRKN, PTEN, PTPRD, RAB35, RAD50, RBM10, RET, RHOA, RNF43, RPTOR, RTEL1, RUNX1, SETD2, SMARCA4, SMARCD1, SOX2, SPEN, SUFU, TET1, TET2, TGFBR1, and TGFBR2 genes in a biological sample from the subject, wherein the presence of one or more mutations in two or more genes indicates the subject is responsive to ICB therapy; and (b) administering ICB therapy to the subject having esophagogastric cancer that is responsive to ICB therapy.

In some embodiments, the cancer is esophagogastric cancer and the method comprises: (a) identifying one or more mutations in two or more genes selected from the group consisting of ABHD17A, ABL1, AGO2, AKT1, AMER1, APC, ARHGDIG, ASXL1, ATR, B2M, BABAM1, BAP1, BCL2, BCOR, BMPR1A, BRAF, BRIP1, BRMS1L, CALR, CARM1, CASP8, CCNE1, CDK12, CDKN1B, CMIP, CRYBG3, CSF3R, CTCF, CTNNB1, DDX39A, DIS3, DNAJB1, E2F3, EED, EIF4A2, EPAS1, EPHA3, EPHA7, ERBB3, ERCC2, ESR1, ETV1, ETV6, EWSR1, EZH1, FANCA, FGF19, FGF3, FGFR1, FGFR3, FYN, GATA2, GATA3, GNA12, GOT1L1, GREM1, H3F3A, HGF, HIST1HIE, HIST1H3E, HIST1H3G, HIST1H3H, HNF1A, HRAS, ID3, IDH2, IFNGR1, IL7R, INPP4B, IRS1, IRS2, JAK2, JAK3, KDM5C, KMT2B, LOC440982, LRP12, LRRC49, MAGIX, MAP3K13, MAPK1, MLH1, MMUT, MPL, MTOR, MYC, MYCN, NBN, NCOA3, NF1, NKX2-1, NOL4L, NOTCH2, NOTCH3, NOTCH4, NSD2, NSD3, NTHL1, NTRK2, PAK1, PARP1, PBK, PDCD1, PDGFRB, PIK3CB, PIK3R3, PMS1, PNRC1, PPARG, PPM1D, PPP2R1A, PRDM1, PRKCI, PRKD1, PRKN, RAB35, RAC1, RAD50, RAD52, RBM10, RET, RIT1, RPTOR, RTEL1, RUNX1, SDHA, SDHB, SEC16A, SEC24B-AS1, SETD2, SKIL, SMARCD1, SNAR-E, SOX2, SRC, STAG2, STAT3, SUFU, TAP1, TAP2, TCF3, TGFBR1, TMPRSS2, TP53BP1, TRAF7, TRIOBP, XIAP, ZRSR2, and ZSCAN5A in a biological sample from the subject having esophagogastric cancer, wherein the presence of one or more mutations in the two or more genes indicates the subject is responsive to ICB therapy; and (b) administering ICB therapy to the subject having esophagogastric cancer that is responsive to ICB therapy.

In some embodiments, the cancer is esophagogastric cancer, wherein the method comprises: (a) identifying one or more mutations in the ABHD17A, ABL1, AGO2, AKT1, AMER1, APC, ARHGDIG, ASXL1, ATR, B2M, BABAM1, BAP1, BCL2, BCOR, BMPR1A, BRAF, BRIP1, BRMS1L, CALR, CARM1, CASP8, CCNE1, CDK12, CDKN1B, CMIP, CRYBG3, CSF3R, CTCF, CTNNB1, DDX39A, DIS3, DNAJB1, E2F3, EED, EIF4A2, EPAS1, EPHA3, EPHA7, ERBB3, ERCC2, ESR1, ETV1, ETV6, EWSR1, EZH1, FANCA, FGF19, FGF3, FGFR1, FGFR3, FYN, GATA2, GATA3, GNA12, GOT1L1, GREM1, H3F3A, HGF, HIST1HIE, HIST1H3E, HIST1H3G, HIST1H3H, HNF1A, HRAS, ID3, IDH2, IFNGR1, IL7R, INPP4B, IRS1, IRS2, JAK2, JAK3, KDM5C, KMT2B, LOC440982, LRP12, LRRC49, MAGIX, MAP3K13, MAPK1, MLH1, MMUT, MPL, MTOR, MYC, MYCN, NBN, NCOA3, NF1, NKX2-1, NOL4L, NOTCH2, NOTCH3, NOTCH4, NSD2, NSD3, NTHL1, NTRK2, PAK1, PARP1, PBK, PDCD1, PDGFRB, PIK3CB, PIK3R3, PMS1, PNRC1, PPARG, PPM1D, PPP2R1A, PRDM1, PRKCI, PRKD1, PRKN, RAB35, RAC1, RAD50, RAD52, RBM10, RET, RIT1, RPTOR, RTEL1, RUNX1, SDHA, SDHB, SEC16A, SEC24B-AS1, SETD2, SKIL, SMARCD1, SNAR-E, SOX2, SRC, STAG2, STAT3, SUFU, TAP1, TAP2, TCF3, TGFBR1, TMPRSS2, TP53BP1, TRAF7, TRIOBP, XIAP, ZRSR2, and ZSCAN5A genes in a biological sample from the subject, wherein the presence of one or more mutations in two or more genes indicates the subject is responsive to ICB therapy; and (b) administering ICB therapy to the subject having esophagogastric cancer that is responsive to ICB therapy.

In some embodiments, the cancer is head and neck cancer and the method comprises: (a) identifying one or more mutations in two or more genes selected from the group consisting of AMER1, AR, ARID1A, ARID1B, ASXL1, ATRX, AXL, BRAF, CTNNB1, CYLD, DDR2, EED, ELF3, EP300, EPAS1, EPHA3, EPHA5, EPHA7, EPHB1, ERCC4, ETV6, FLCN, FLT4, GATA2, GPS2, GRIN2A, HLA-B, HOXB13, HRAS, IFNGR1, JAK1, JAK2, KMT2D, LATS1, MAP2K2, MAP3K1, MST1R, NBN, NOTCH1, NOTCH3, NOTCH4, NTRK1, NUF2, NUP93, PAK5, PIK3CA, PIK3CD, PMS2, PRKAR1A, RAD51, RICTOR, RPS6KA4, SETD2, SH2B3, SLX4, SPEN, TET2, TGFBR2, TRAF2, and ZFHX3 in a biological sample from the subject having head and neck cancer, wherein the presence of one or more mutations in the two or more genes indicates the subject is responsive to ICB therapy; and (b) administering ICB therapy to the subject having head and neck cancer that is responsive to ICB therapy.

In some embodiments, the cancer is head and neck cancer and the method comprises: (a) identifying one or more mutations in the AMER1, AR, ARID1A, ARID1B, ASXL1, ATRX, AXL, BRAF, CTNNB1, CYLD, DDR2, EED, ELF3, EP300, EPAS1, EPHA3, EPHA5, EPHA7, EPHB1, ERCC4, ETV6, FLCN, FLT4, GATA2, GPS2, GRIN2A, HLA-B, HOXB13, HRAS, IFNGR1, JAK1, JAK2, KMT2D, LATS1, MAP2K2, MAP3K1, MST1R, NBN, NOTCH1, NOTCH3, NOTCH4, NTRK1, NUF2, NUP93, PAK5, PIK3CA, PIK3CD, PMS2, PRKAR1A, RAD51, RICTOR, RPS6KA4, SETD2, SH2B3, SLX4, SPEN, TET2, TGFBR2, TRAF2, and ZFHX3 genes in a biological sample from the subject, wherein the presence of one or more mutations in two or more genes indicates the subject is responsive to ICB therapy; and (b) administering ICB therapy to the subject having head and neck cancer that is responsive to ICB therapy.

In some embodiments, the cancer is head and neck cancer and the method comprises: (a) identifying one or more mutations in two or more genes selected from the group consisting of ABL1, ABRAXAS1, AMER1, AR, ARAF, ARID1A, ARID1B, ASXL1, ATF1, ATM, AXL, BCOR, BRAF, CALR, CDK6, CSF3R, CTCF, CTNNB1, CXCR4, CYLD, DDR2, DNMT3A, DROSHA, EED, EGFL7, EGFR, EIF4A2, ELF3, EMID1, EPAS1, EPHA3, EPHA5, EPHA7, EPHB1, ERCC2, ERCC4, ETV6, FAM169A, FGF19, FGFR1, FGFR2, FGFR3, FH, FLCN, FLT4, FOXO1, GATA1, GATA2, GATA3, GPS2, GRIN2A, HIST1H2BD, HIST1H3A, HIST1H3E, HLA-B, HNF1A, HOXB13, HRAS, IFNGR1, IGF1, IKZF1, INPP4A, INPPL1, INSRR, IRF4, JAK1, JAK2, KMT5A, KNSTRN, LATS1, MAP2K1, MAP2K2, MAP3K1, MCL1, MDM2, MEN1, MSH3, MST1, MST1R, MUTYH, MYOD1, NBN, NKX2-1, NOTCH3, NPM1, NSD2, NSD3, NTRK1, NTRK2, NUF2, NUP93, PAK5, PALLD, PIK3CD, PIK3CG, PIK3R3, PMS2, POLD1, PPM1D, PRKAR1A, PRKCI, PTCH1, RAD21, RAD50, RAD51, RICTOR, RPS6KA4, RPS6KB2, RTEL1, SETD2, SF3B1, SH2B3, SHQ1, SLX4, SMARCD1, SMO, SOX9, SPEN, SRC, STAG2, TCF7L2, TET2, TGFBR2, TOP1, TP53BP1, TRAF2, TSHR, U2AF1, and YAP1 in a biological sample from the subject having head and neck cancer, wherein the presence of one or more mutations in the two or more genes indicates the subject is responsive to ICB therapy; and (b) administering ICB therapy to the subject having head and neck cancer that is responsive to ICB therapy.

In some embodiments, the cancer is head and neck cancer, wherein the method comprises: (a) identifying one or more mutations in the ABL1, ABRAXAS1, AMER1, AR, ARAF, ARID1A, ARID1B, ASXL1, ATF1, ATM, AXL, BCOR, BRAF, CALR, CDK6, CSF3R, CTCF, CTNNB1, CXCR4, CYLD, DDR2, DNMT3A, DROSHA, EED, EGFL7, EGFR, EIF4A2, ELF3, EMID1, EPAS1, EPHA3, EPHA5, EPHA7, EPHB1, ERCC2, ERCC4, ETV6, FAM169A, FGF19, FGFR1, FGFR2, FGFR3, FH, FLCN, FLT4, FOXO1, GATA1, GATA2, GATA3, GPS2, GRIN2A, HIST1H2BD, HIST1H3A, HIST1H3E, HLA-B, HNF1A, HOXB13, HRAS, IFNGR1, IGF1, IKZF1, INPP4A, INPPL1, INSRR, IRF4, JAK1, JAK2, KMT5A, KNSTRN, LATS1, MAP2K1, MAP2K2, MAP3K1, MCL1, MDM2, MEN1, MSH3, MST1, MST1R, MUTYH, MYOD1, NBN, NKX2-1, NOTCH3, NPM1, NSD2, NSD3, NTRK1, NTRK2, NUF2, NUP93, PAK5, PALLD, PIK3CD, PIK3CG, PIK3R3, PMS2, POLD1, PPM1D, PRKAR1A, PRKCI, PTCH1, RAD21, RAD50, RAD51, RICTOR, RPS6KA4, RPS6KB2, RTEL1, SETD2, SF3B1, SH2B3, SHQ1, SLX4, SMARCD1, SMO, SOX9, SPEN, SRC, STAG2, TCF7L2, TET2, TGFBR2, TOP1, TP53BP1, TRAF2, TSHR, U2AF1, and YAP1 genes in a biological sample from the subject, wherein the presence of one or more mutations in two or more genes indicates the subject is responsive to ICB therapy; and (b) administering ICB therapy to the subject having head and neck cancer that is responsive to ICB therapy.

In some embodiments, the cancer is glioma and the method comprises: (a) identifying one or more mutations in two or more genes selected from the group consisting of APC, AR, AXIN1, BCL6, BRCA1, BRCA2, BRIP1, C1ORF127, CBL, CDH1, CDKN1B, CHEK2, CLYBL, CYLD, DAXX, DIS3, DNMT3A, DOT1L, EP300, EPAS1, EPHA5, EPHA7, ERCC3, ERG, ERRFI1, ETV1, FGF3, FGF4, FGFR1, FGFR3, FGFR4, FOXA1, FOXO1, FOXP1, GNAQ, HGF, HIST1H3D, HIST3H3, IFNGR1, IL10, INPP4A, INSR, IRF4, IRS1, JAK2, KEAP1, KMT2B, KMT2C, KMT2D, LATS2, MRE11, MST1R, MTOR, MUTYH, MYCL, MYD88, MYOD1, NFE2L2, PARP1, PBRM1, PIK3C2G, PIK3R2, PMAIP1, POLE, PTPRD, RAD51B, RAD51D, RECQL4, RIT1, RPTOR, RTEL1, SDHA, SLX4, SMAD2, SOX2, SPEN, STAT3, STAT5A, STK11, TACC3, TET1, TGFBR2, TLL1, TNFAIP3, TNFRSF14, TSC1, U2AF1, and VHL in a biological sample from the subject having glioma, wherein the presence of one or more mutations in the two or more genes indicates the subject is responsive to ICB therapy; and (b) administering ICB therapy to the subject having glioma that is responsive to ICB therapy.

In some embodiments, the cancer is glioma, wherein the method comprises: (a) identifying one or more mutations in the APC, AR, AXIN1, BCL6, BRCA1, BRCA2, BRIP1, C1ORF127, CBL, CDH1, CDKN1B, CHEK2, CLYBL, CYLD, DAXX, DIS3, DNMT3A, DOT1L, EP300, EPAS1, EPHA5, EPHA7, ERCC3, ERG, ERRFI1, ETV1, FGF3, FGF4, FGFR1, FGFR3, FGFR4, FOXA1, FOXO1, FOXP1, GNAQ, HGF, HIST1H3D, HIST3H3, IFNGR1, IL10, INPP4A, INSR, IRF4, IRS1, JAK2, KEAP1, KMT2B, KMT2C, KMT2D, LATS2, MRE11, MST1R, MTOR, MUTYH, MYCL, MYD88, MYOD1, NFE2L2, PARP1, PBRM1, PIK3C2G, PIK3R2, PMAIP1, POLE, PTPRD, RAD51B, RAD51D, RECQL4, RIT1, RPTOR, RTEL1, SDHA, SLX4, SMAD2, SOX2, SPEN, STAT3, STAT5A, STK11, TACC3, TET1, TGFBR2, TLL1, TNFAIP3, TNFRSF14, TSC1, U2AF1, and VHL genes in a biological sample from the subject, wherein the presence of one or more mutations in two or more genes indicates the subject is responsive to ICB therapy; and (b) administering ICB therapy to the subject having glioma that is responsive to ICB therapy.

In some methods, the cancer is glioma and the method comprises: (a) identifying one or more mutations in two or more genes selected from the group consisting of APC, AR, AXIN1, BCL6, BRCA1, BRCA2, BRIP1, C1ORF127, CBL, CDH1, CDKN1B, CHEK2, CLYBL, CYLD, DAXX, DIS3, DNMT3A, DOT1L, EP300, EPAS1, EPHA5, EPHA7, ERCC3, ERG, ERRFI1, ETV1, FGF3, FGF4, FGFR1, FGFR3, FGFR4, FOXA1, FOXO1, FOXP1, GNAQ, HGF, HIST1H3D, HIST3H3, IFNGR1, IL10, INPP4A, INSR, IRF4, IRS1, JAK2, KEAP1, KMT2B, KMT2C, KMT2D, LATS2, MRE11, MST1R, MTOR, MUTYH, MYCL, MYD88, MYOD1, NFE2L2, PARP1, PBRM1, PIK3C2G, PIK3R2, PMAIP1, POLE, PTPRD, RAD51B, RAD51D, RECQL4, RIT1, RPTOR, RTEL1, SDHA, SLX4, SMAD2, SOX2, SPEN, STAT3, STAT5A, STK11, TACC3, TET1, TGFBR2, TLL1, TNFAIP3, TNFRSF14, TSC1, U2AF1, and VHL in a biological sample from the subject having glioma, wherein the presence of one or more mutations in the two or more genes indicates the subject is responsive to ICB therapy; and (b) administering ICB therapy to the subject having glioma that is responsive to ICB therapy.

In some embodiments, the cancer is glioma, wherein the method comprises: (a) identifying one or more mutations in the APC, AR, AXIN1, BCL6, BRCA1, BRCA2, BRIP1, C1ORF127, CBL, CDH1, CDKN1B, CHEK2, CLYBL, CYLD, DAXX, DIS3, DNMT3A, DOT1L, EP300, EPAS1, EPHA5, EPHA7, ERCC3, ERG, ERRFI1, ETV1, FGF3, FGF4, FGFR1, FGFR3, FGFR4, FOXA1, FOXO1, FOXP1, GNAQ, HGF, HIST1H3D, HIST3H3, IFNGR1, IL10, INPP4A, INSR, IRF4, IRS1, JAK2, KEAP1, KMT2B, KMT2C, KMT2D, LATS2, MRE11, MST1R, MTOR, MUTYH, MYCL, MYD88, MYOD1, NFE2L2, PARP1, PBRM1, PIK3C2G, PIK3R2, PMAIP1, POLE, PTPRD, RAD51B, RAD51D, RECQL4, RIT1, RPTOR, RTEL1, SDHA, SLX4, SMAD2, SOX2, SPEN, STAT3, STAT5A, STK11, TACC3, TET1, TGFBR2, TLL1, TNFAIP3, TNFRSF14, TSC1, U2AF1, and VHL genes in a biological sample from the subject, wherein the presence of one or more mutations in two or more genes indicates the subject is responsive to ICB therapy; and (b) administering ICB therapy to the subject having glioma that is responsive to ICB therapy.

In some embodiments, the cancer is breast cancer and the method comprises: (a) identifying one or more mutations in two or more genes selected from the group consisting of APC, AR, ARID1A, ARID2, ASXL1, ATM, ATR, BRCA2, CARD11, CCNE1, CDK12, CDKN2A, CELF2, COL14A1, DDR2, DEPTOR, DNMT3B, E2F3, ERCC5, FGFR4, FH, FLT4, FOXP1, FYN, GATA3, HLA-A, IGF1R, INSR, KMT2A, KMT2C, MAP2K4, MAP3K1, MDM2, MGA, MSH6, MST1R, NF1, NOTCH4, NTRK3, NUP93, PARP1, PIK3R1, PIK3R2, POLE, PTPRS, RAD50, RB1, RICTOR, RPS6KB2, RUNX1, SH2D1A, SMARCA4, SOX17, SPEN, XIAP, and YES1 in a biological sample from the subject having breast cancer, wherein the presence of one or more mutations in the two or more genes indicates the subject is responsive to ICB therapy; and (b) administering ICB therapy to the subject having breast cancer that is responsive to ICB therapy.

In some embodiments, the cancer is breast cancer, wherein the method comprises: (a) identifying one or more mutations in the APC, AR, ARID1A, ARID2, ASXL1, ATM, ATR, BRCA2, CARD11, CCNE1, CDK12, CDKN2A, CELF2, COL14A1, DDR2, DEPTOR, DNMT3B, E2F3, ERCC5, FGFR4, FH, FLT4, FOXP1, FYN, GATA3, HLA-A, IGF1R, INSR, KMT2A, KMT2C, MAP2K4, MAP3K1, MDM2, MGA, MSH6, MST1R, NF1, NOTCH4, NTRK3, NUP93, PARP1, PIK3R1, PIK3R2, POLE, PTPRS, RAD50, RB1, RICTOR, RPS6KB2, RUNX1, SH2D1A, SMARCA4, SOX17, SPEN, XIAP, and YES1 genes in a biological sample from the subject, wherein the presence of one or more mutations in two or more genes indicates the subject is responsive to ICB therapy; and (b) administering ICB therapy to the subject having breast cancer that is responsive to ICB therapy.

In some embodiments, the cancer is breast cancer and the method comprises: (a) identifying one or more mutations in two or more genes selected from the group consisting of APC, AR, ARID2, ASXL1, ATR, BRCA2, CARD11, CCNE1, CDK12, CELF2, COL14A1, DDR2, DEPTOR, DNMT3B, E2F3, ERCC5, FGFR4, FH, FLT4, FOXP1, FYN, GATA3, HLA-A, IGF1R, INSR, KMT2A, MAP3K1, MDM2, MGA, MSH6, MST1R, NTRK3, NUP93, PARP1, PIK3R1, POLE, PTPRS, RAD50, RB1, RPS6KB2, RUNX1, SH2D1A, SMARCA4, SOX17, SPEN, XIAP, and YES1 in a biological sample from the subject having breast cancer, wherein the presence of one or more mutations in the two or more genes indicates the subject is responsive to ICB therapy; and (b) administering ICB therapy to the subject having breast cancer that is responsive to ICB therapy.

In some embodiments, the cancer is breast cancer, wherein the method comprises: (a) identifying one or more mutations in the APC, AR, ARID2, ASXL1, ATR, BRCA2, CARD11, CCNE1, CDK12, CELF2, COL14A1, DDR2, DEPTOR, DNMT3B, E2F3, ERCC5, FGFR4, FH, FLT4, FOXP1, FYN, GATA3, HLA-A, IGF1R, INSR, KMT2A, MAP3K1, MDM2, MGA, MSH6, MST1R, NTRK3, NUP93, PARP1, PIK3R1, POLE, PTPRS, RAD50, RB1, RPS6KB2, RUNX1, SH2D1A, SMARCA4, SOX17, SPEN, XIAP, and YES1 genes in a biological sample from the subject, wherein the presence of one or more mutations in two or more genes indicates the subject is responsive to ICB therapy; and (b) administering ICB therapy to the subject having breast cancer that is responsive to ICB therapy.

In any of the methods provided herein, one or more mutations can be identified in two or more genes associated with ICB responsiveness, wherein the two or more genes are part of a panel of genes that can comprise, consist of, or consist essentially of the genes listed in any of the methods provided herein. As an example, a panel of genes comprising, consisting of, or consisting essentially of ABL1, ASXL1, ATM, BCOR, BRCA2, BRIP1, CARD11, CD79B, CDC73, CIC, EPHA3, EPHA5, EPHA, EPHB1, ERBB4, ERCC4, FGFR4, FLT3, FOXL2, HGF, INHBA, JAK3, MAX, MDC1, MED12, MET, MGA, MRE11, MSH2 NF2, NFKBIA, NOTCH1, NOTCH2, NTRK3, NUF, PARP1, PAX5, PGR, PIK3C2G, PIK3C3, PIK3CG, PIM1, POLE PPM1D, PPP2R1A, PTPRD, RET, STAT3, TENT, TET1, TSC2, and ZFHX3 can be used to identify one or more mutations in two or more genes selected from the group consisting of ABL1, ASXL1, ATM, BCOR, BRCA2, BRIP1, CARD11, CD79B, CDC73, CIC, EPHA3, EPHA5, EPHA, EPHB1, ERBB4, ERCC4, FGFR4, FLT3, FOXL2, HGF, INHBA, JAK3, MAX, MDC1, MED12, MET, MGA, MRE11, MSH2 NF2, NFKBIA, NOTCH1, NOTCH2, NTRK3, NUF, PARP1, PAX5, PGR, PIK3C2G, PIK3C3, PIK3CG, PIM1, POLE PPM1D, PPP2R1A, PTPRD, RET, STAT3, TENT, TET1, TSC2, and ZFHX3. It is also understood that the gene panel can also comprise, consist of, or consist essentially of a subset of any of the lists of genes provided herein.

As used throughout, the term "gene" refers to a nucleic acid, DNA or RNA, involved in producing or encoding a polypeptide. It may include non-coding regions preceding and following the coding region (leader and trailer) as well as intervening sequences (introns) between individual coding segments (exons). As used throughout, the term "nucleic acid" or "nucleotide" refers to deoxyribonucleic acids (DNA) or ribonucleic acids (RNA) and polymers thereof in either single- or double-stranded form. It is understood that when a DNA sequence is described, its corresponding RNA is also described, wherein thymidine is represented as uridine. Unless otherwise indicated, a particular nucleic acid sequence also implicitly encompasses modified variants thereof, alleles, orthologs, SNPs, and complementary sequences as well as the sequence explicitly indicated.

In any of the methods provided herein, the one or more mutations in a gene, (e.g., one, two, three, four, five, six, seven, eight, nine, ten or more mutations) can occur in a non-coding and/or a coding region of the gene. In any of the methods set forth herein, two or more (e.g., two, three, four, five, six, seven, eight, nine, ten, or more) genes in a sample from the subject can comprise one or more mutations. As used throughout, "a mutation" can be, but is not limited to, a nucleic acid substitution, an insertion, a deletion, a translocation, an inversion, a frameshift mutation, a duplication or repeat expansion in one or more genes described herein, as compared to the wild-type gene. It is understood that the presence of one or more mutations in two or more genes set forth in any of the methods provided herein indicates the subject is sensitive or responsive to ICB therapy. If the presence of one or more mutations in two or more genes is detected, the ICB can be administered to the subject, or ICB therapy can be continued if ICB therapy has been administered to the subject.

It is also understood that the absence of one or more mutations in two or more genes set forth in any of the methods provided herein, indicates the subject is resistant to ICB therapy. If an absence of one or more mutations is detected, the subject is resistant to ICB therapy and one of skill in the art would know not to administer ICB therapy to the subject, or discontinue ICB therapy if ICB therapy has been administered to the subject.

In some embodiments, the one or more mutations in two or more genes associated with responsiveness to ICB therapy are identified by next generation sequencing, whole exome sequencing (i.e., sequencing, primarily, of protein-coding regions of a gene), polymerase chain reaction (See, for example, Lohmann et al. *Methods* 59(1): 10-9 (2013)), Sanger sequencing, or targeted sequencing techniques. In some embodiments, the targeted sequencing technique is selected from the group consisting of MSK-IMPACT™ (Cheng et al. "*J. Mol. Diagn.* 17(3): 251-264 (2015)), FoundationOne® CDx (Foundation Medicine, Inc., Cambridge, MA) (Woodhouse et al., *PLOS ONE* 15(9): e0237802), Oncomine™ (ThermoFisher, Waltham, MA) (Williams et al. *Virchows Archiv* 473: 489-503 (2018)), and any combination thereof.

In some embodiments, the one or more mutations in two or more genes associated with responsiveness to ICB therapy are identified via DNA or RNA microarray analysis. Gene microarray technology rests on the ability to deposit many, different DNA sequences on a small surface, usually a glass slide (often referred to as a "chip"). The different DNA fragments are arranged in rows and columns such that the identity of each fragment is known through its location on the array. See, for example, Govindarajan et al. "Microarray and its applications," *J. Pharm. Bioallied Sci.* August 4(Suppl 2): S310-S312 (2012); Virtanen and Woodgett, "Clinical Uses of Microarrays in Cancer *Research Methods Mol. Med.* 141: 87-113 (2008)); and Kim and Kang "Microarray Applications in Cancer Research," *Cancer Research and Treatment* 36(4): 207-13 (2004)).

As used herein, the term "biological sample" or "sample" refers to a sample that has been obtained from a patient or subject. In some instances, the biological sample can be a tissue, cell(s), a bodily fluid (e.g., blood, serum, sputum, lung fluid, mucus, tears, lymphatic fluid, synovial fluid, cerebrospinal fluid, saliva, amniotic fluid, amniotic cord blood, urine, vaginal fluid and semen). A biological sample can also be a homogenate, lysate or extract prepared from a whole organism or a subset of its tissues, cells or bodily fluids. In some instances, nucleic acids, for example, DNA or RNA is isolated from a tissue, cell or bodily fluid of the subject.

In some embodiments, the biological sample comprises blood for the subject. In yet another embodiment, the biological sample comprises plasma. In other embodiments, the biological sample may be obtained directly from a subject (e.g., by blood or tissue sampling) or from a third party (e.g., received from an intermediary, such as a healthcare provider or lab technician).

In some embodiments, the biological sample is a tumor biopsy from the subject. In some embodiments, the biological sample comprises circulating tumor cells. In some embodiments, the biological sample comprises circulating free DNA from the subject's blood. The methods and compositions disclosed herein can be used on a sample either in vitro (for example, on isolated cells or tissues) or in vivo in a subject (i.e. living organism, such as a patient).

As used herein, cancer is a disease characterized by the rapid and uncontrolled growth of aberrant cells. Cancer cells can spread locally or through the bloodstream and lymphatic system to other parts of the body. The cancer can be a solid tumor. Solid tumors include, by way of example, bone and connective tissue sarcomas (e.g., bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma), brain tumors (e.g., glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma), breast cancer (e.g., adenocarcinoma, lobular (small cell) carcinoma, intraductal carcinoma, medullary breast cancer, mucinous breast cancer, tubular breast cancer, papillary breast cancer, Paget's disease, and inflammatory breast cancer), adrenal cancer (e.g., pheochromocytoma and adrenocortical carcinoma), thyroid cancer (e.g., papillary or follicular thyroid cancer, medullary thyroid cancer and anaplastic thyroid cancer), pancreatic cancer (e.g., insulinoma, gastrinoma, glucagonoma, vipoma, somatostatin-secreting tumor, and carcinoid or islet cell tumor), pituitary cancers (e.g., Cushing's disease, prolactin-secreting tumor, acromegaly, and diabetes insipidus), eye cancers (e.g., ocular melanoma such as iris melanoma, choroidal melanoma, and ciliary body melanoma, and retinoblastoma), vaginal cancers (e.g., squamous cell carcinoma, adenocarcinoma, and melanoma), vulvar cancer (e.g., squamous cell carcinoma, melanoma, adenocarcinoma, basal cell carcinoma, sarcoma, and Paget's disease), cervical cancers (e.g., squamous cell carcinoma and adenocarcinoma), uterine cancers (e.g., endometrial carcinoma and uterine sarcoma), ovarian cancers (e.g., ovarian epithelial carcinoma, borderline tumor, germ cell tumor, and stromal tumor), esophageal cancers (e.g., squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma), stomach cancers (e.g., adenocarcinoma, fungating (polypoid), ulcerating, superficial spreading, diffusely spreading, malignant lymphoma, liposarcoma, fibrosarcoma, and carcinosarcoma), colon cancers, rectal cancers, liver cancers (e.g., hepatocellular carcinoma and hepatoblastoma), gallbladder cancers (e.g., adenocarcinoma), cholangiocarcinomas (papillary, nodular, and diffuse), lung cancers (e.g., non-small cell lung cancer, squamous cell carcinoma (epidermoid carcinoma), adenocarcinoma, large-cell carcinoma and small-cell lung cancer), testicular cancers (e.g., germinal tumor, seminoma, anaplastic, classic (typical), spermatocytic, nonseminoma, embryonal carcinoma, teratoma carcinoma, choriocarcinoma (yolk-sac tumor)), prostate cancers (e.g., adenocarcinoma, leiomyosarcoma, and rhabdomyosarcoma), penile cancers, oral cancers (e.g., squamous cell carcinoma), basal cancers, salivary gland cancers (e.g., adenocarcinoma, mucoepidermoid carcinoma, and adenoidcystic carcinoma), esopharyngeal cancers (e.g., squamous cell cancer and verrucous cancer), skin cancers (e.g., basal cell carcinoma, squamous cell carcinoma and melanoma, superficial spreading melanoma, nodular melanoma, lentigo malignant melanoma, acral lentiginous melanoma), kidney cancers (e.g., renal cell cancer, adenocarcinoma, hypernephroma, fibrosarcoma, transitional cell cancer (renal pelvis and/or ureter), Wilms' tumor), bladder cancers (e.g., transitional cell carcinoma, squamous cell cancer, adenocarcinoma, and carcinosarcoma). In addition, cancers include myxosarcoma, osteogenic sarcoma, endotheliosarcoma, lymphangioendothelioma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

In some embodiments, the cancer is a blood or hematological cancer, such as a leukemia (e.g., acute leukemia; acute lymphocytic leukemia; acute myelocytic leukemias, such as myeloblastic, promyelocytic, myelomonocytic, monocytic, erythroleukemia leukemias and myelodysplastic syndrome; chronic myelocytic (granulocytic) leukemia; chronic lymphocytic leukemia; hairy cell leukemia), polycythemia vera, or lymphomas (e.g., Hodgkin's disease or non-Hodgkin's disease lymphomas (e.g., diffuse anaplastic lymphoma kinase (ALK) negative, large B-cell lymphoma (DLBCL); diffuse anaplastic lymphoma kinase (ALK) positive, large B-cell lymphoma (DLBCL); anaplastic lymphoma kinase (ALK) positive, ALK+anaplastic large-cell lymphoma (ALCL), acute myeloid lymphoma (AML))), multiple myelomas (e.g., smoldering multiple myeloma, non-secretory myeloma, osteosclerotic myeloma, plasma cell leukemia, solitary plasmacytoma and extramedullary plasmacytoma), Waldenstrom's macroglobulinemia, monoclonal gammopathy of undetermined significance, benign monoclonal gammopathy and heavy chain disease.

In any of the methods provided herein, the ICB therapy can be selected from the group consisting of a PD-1 inhibitor, a PD-L1 inhibitor, a CTLA4 inhibitor, and combinations thereof. In some embodiments, the ICB therapy comprises an antibody selected from the group consisting of an anti-PD1 antibody, anti-PD-L1 antibody, an anti-CTLA4 antibody, and any combinations thereof. IN some embodiments, the antibody is selected from the group consisting of atezolizumab, avelumab, camrelizumab, cemiplimab, durvalumab, ipilimumab, nivolumab, pembrolizumab, sintilimab, Tislelizumab, Toripalimab, tremelimumab, and any combinations thereof.

As used throughout, by subject is meant an individual. The subject can be an adult subject or a pediatric subject. Pediatric subjects include subjects ranging in age from birth to eighteen years of age. Preferably, the subject is an animal, for example, a mammal such as a primate, and, more preferably, a human. Non-human primates are subjects as well. The term subject includes cats, dogs, reptiles, amphibians, livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

As used herein the terms "treatment", "treat", or "treating" refers to a method of reducing one or more of the effects of the disease or one or more symptoms of the disease, for example, cancer, in the subject. Thus, in the disclosed methods, treatment can refer to a 10%, 20%, 30%, 40%, 50%, 60%, 70%, 80%, 90%, or 100% reduction in the severity of cancer. In addition to alleviation or prevention of symptoms, treatment can also slow or stop the progression or worsening of a disease, disorder, or condition and/or the remission of the disease, disorder or condition. For example, a method for treating cancer is considered to be a treatment if there is a 10% reduction in one or more symptoms of cancer in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease or symptoms of the disease.

Any of the treatment methods described herein can further comprise administering an effective amount of a second therapeutic agent to the subject. In some embodiments, the second therapeutic agent is a chemotherapeutic agent. Exemplary chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof.

It is understood that combinations, for example, ICB therapy and a chemotherapeutic agent, can be administered either concomitantly (e.g., as an admixture), separately, but simultaneously (e.g., via separate intravenous lines into the same subject), or sequentially (e.g., one of the compounds or agents is given first followed by the second). Any of the methods provided herein can further comprise radiation therapy or surgery. In any of the methods provided herein, the subject is a subject diagnosed with cancer. In any of the methods provided herein, the method can further comprise diagnosing the subject with cancer.

As used throughout, "effective amount" or "therapeutically effective amount" refers to an amount sufficient to effect beneficial or desirable biological and/or clinical results. The effective amount of any of the therapeutic agents described herein, for example, ICB therapy can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Other factors that influence dosage can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject also depends upon the judgment of the treating medical practitioner. A therapeutically effective amount is also one in which any toxic or detrimental effects of the composition are outweighed by the therapeutically beneficial effects.

As used herein, administer or administration refers to the act of introducing, injecting or otherwise physically delivering a substance as it exists outside the body into a subject, such as by mucosal, intradermal, intravenous, intratumoral, intramuscular, intrathecal, intracranial, intrarectal, oral, subcutaneous delivery and/or any other method of physical delivery described herein or known in the art.

Any of the therapeutic agents described herein are administered in a number of ways depending on whether local or systemic treatment is desired, and on the area to be treated. The compositions are administered via any of several routes of administration, including orally, parenterally, intrathecally, intracranially, intramucosally, intravenously, intraperitoneally, intraventricularly, intramuscularly, subcutaneously, intracavity or transdermally. Administration can be achieved by, e.g., topical administration, local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223, U.S Patent Application Publication No. 20040180095A, and U.S. patent Ser. No. 10/286,197.

In some methods, the therapeutic agent can be delivered to the subject by way of an implantable device based on, e.g., diffusive, erodible, or convective systems, osmotic pumps, biodegradable implants, electrodiffusion systems, electroosmosis systems, vapor pressure pumps, electrolytic pumps, effervescent pumps, piezoelectric pumps, erosion-based systems, or electromechanical systems. Effective doses for any of the administration methods described herein can be extrapolated from dose-response curves derived from in vitro or animal model test systems.

Any of the therapeutic agents described herein can be formulated as a pharmaceutical composition. In some embodiments, the pharmaceutical composition can further comprise a carrier. The term carrier means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject. Such pharmaceutically acceptable carriers include sterile biocompatible pharmaceutical carriers, including, but not limited to, saline, buffered saline, artificial cerebral spinal fluid, dextrose, and water.

Depending on the intended mode of administration, a pharmaceutical composition comprising a therapeutic agent described herein, can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

Also provided herein is a kit for determining the sensitivity or responsiveness of a subject to one or more treatments for cancer (e.g., immune checkpoint blockade therapy) by assaying for the presence or absence of one or more mutations in two or more genes set forth in any of the methods provided herein. The kit can include probes for sequencing the genes as provided herein to determine the presence or absence of one or more mutations in two or more genes as compared to the wildtype genes. The kit can also include a device for identifying genetic mutations, for example, a gene chip, comprising a gene panel, wherein the gene panel comprises, consists of, or consists essentially of any of the lists of genes described herein. The kits can also include instructions for using the kit to predict the sensitivity or resistance of the subject to the treatment.

Example I

A Gene Mutation Signature Predicts Response to Immunotherapy in Melanoma, Non-Small Cell Lung, Bladder and Colorectal Cancer Patients Identification of patients who can benefit from immune checkpoint blockade (ICB) therapy is key for cost-effective treatment of cancer patients. It was hypothesized that mutations in select genes can predict tumor response to ICB therapy better than tumor mutational load (TMB).

Methods. A list of 42 genes that can predict for benefit from ICB treatment in melanoma, NSCLC, bladder, and colorectal cancer patients was compiled by analyzing data from a recently published cohort of 1,661 patients. The genes and their corresponding GenBank Accessions Nos. are set forth below in Table 1. The influences of different mutation signatures in the candidate genes was evaluated. Their associations with tumor mutational burden (TMB) were evaluated in the 1,661-patient cohort as well as The Cancer Atlas Genome (TCGA) Pan Cancer Atlas cohorts. The predictive powers of different mutation signatures were then examined in unrelated cohorts of ICB-treated non-small cell lung (SCLC) and melanoma cancer patients.

TABLE 1

42 genes that influence survival of ICB patients

| Gene Name | GenBank Accession No. |
|---|---|
| ABL1 | NG_012034.1 |
| ALK | NG_009445.1 |
| ATM | NG_009830.1 |
| BRCA1 | NG_005905.2 |
| BTK | NG_009616.1 |
| CARM1 | NM_001370088.1 |
| CREBBP | NG_009873.2 |
| CTCF | NG_033892.1 |
| CYLD | NG_012061.1 |
| DNMT1 | NG_028016.3 |
| DNMT3A | NG_029465.2 |
| DROSHA | NG_051574.1 |
| EPHA5 | NM_001281765.3 |
| EPHA7 | NG_033944.1 |
| EPHB1 | NM_004441.5 |
| ERBB3 | NG_011529.1 |
| FAT1 | NG_046994.1 |
| FBXW7 | NG_029466.2 |
| FGFR2 | NG_012449.2 |
| FGFR4 | NG_012067.1 |
| FLT3 | NG_007066.1 |
| KDR | NG_012004.1 |
| LYN | NG_029593.1 |
| MAX | NG_029830.1 |
| MSI1 | NM_002442.4 |
| NCOA3 | NG_016810.1 |
| NCOR1 | NG_047111.1 |

TABLE 1-continued 42 genes that influence survival of ICB patients

| Gene Name | GenBank Accession No. |
|---|---|
| NF2 | NG_009057.1 |
| NOTCH3 | NG_009819.1 |
| NTRK3 | NG_029619.1 |
| NUF2 | NM_031423.4 |
| PALB2 | NG_007406.1 |
| PPMID | NG_023265.1 |
| PREX2 | NG_047022.1 |
| PTPRD | NG_033963.1 |
| RNF43 | NG_042894.1 |
| ROS1 | NG_033929.1 |
| SHOC2 | NG_028922.1 |
| SMO | NG_023340.2 |
| STAT5B | NM_012448.4 |
| TET1 | NM_030625.3 |
| ZFHX3 | NG_013211.2 |

Patient treatment and mutation data. All patient data were published data from the cBioPortal database (https://www.cbioportal.org), which includes 158 studies from The Cancer Genome Atlas (TCGA), International Cancer Genome Consortium (ICGC), Memorial Sloan Kettering Cancer Center (MSKCC) and other sources within the timeframe of this study (Aug. 17, 2019-Nov. 15, 2019). Candidate genes that might influence ICB treatment outcome were identified using data from a recently published cohort of patients treated with ICB therapy at the Memorial Sloan Kettering Cancer Center (MSKCC). This cohort of patients was used to successfully establish the relationship between TMB and ICB treatment efficacy. It included 1661 patients who underwent ICB treatment and are hereinafter referred to as the MSK-TMB cohort. Mutation data in the MSK-TMB study were obtained by the use of the IMPACT targeted sequencing approach. In addition to patient clinical and genomic data from the MSK-TMB cohort, data from several other published studies in NSCLC, melanoma bladder, and colorectal cancer were used to validate the predictive power of the candidate genes. Additional patient mutation data were also obtained from the 10,425-patient TCGA Pan-Cancer Atlas cohort.

Mutation signatures and survival analysis. To analyze if mutations in 42 candidate genes could predict ICB treatment efficacy, patients were grouped into those with no mutations in the 42 genes (wild type, or wt group), those with mutations in one or more of the 42 genes (mut group), those with only a single mutation in any of the 42 genes (single mutation, or single mut group), and those with 2 or more mutations in the 42 genes (compound mutation, or compound mut group). Overall or progression-free survival of patients with different mutation signatures were then compared in the MSK-TMB cohort and additional cohorts.

Mutational signatures and TMB analysis. To explore the potential association between mutational status of the 42 genes and TMB, TMB was analyzed among wt, single mut, and compound mut groups in the MSK-TMB cohort. TMB was also determined among the 10,336-patient MSK-IMPACT Clinical Sequencing Cohort. Mutational load in both the MSK-TMB and MSK-IMPACT cohorts were derived by several different versions of the IMPACT targeted sequencing assay. To avoid bias based on sequencing methods, TMB was determined (based on mutational status in the 42 genes) by use of mutation count data in the 10,425-patient TCGA Pan-Cancer Atlas cohort, which was sequenced by the whole exome sequencing (WES) method. TMB was derived by normalizing the total mutation count for each sample against 30 MB, which is the approximate total exome length in the human genome.

Estimation of mutation signature prevalence. To determine the incidence of single and compound mutations among the 42 genes in cancer patients, mutation data from the MSK-TMB cohort, the MSK IMPACT cohort, and the TCGA Pan-Cancer Atlas cohort was used.

Statistical analysis. For survival analysis, Kaplan-Meier survival curves were generated by use of the statistical software GraphPad Prism (version 8.2). Nonparametric Mantel-Cox logrank test was used to determine the differences among different patient groups. Hazards ratio (HR) and the 95% confidence interval (CI) were calculated by use of the logrank (Mantel-Cox) test and assuming the Cox proportional-hazards model. For TMB analysis, statistical significance for difference between the mean values of any two groups was determined by use of the unpaired, two-tailed Student's t-test.

Results

Figure 4:
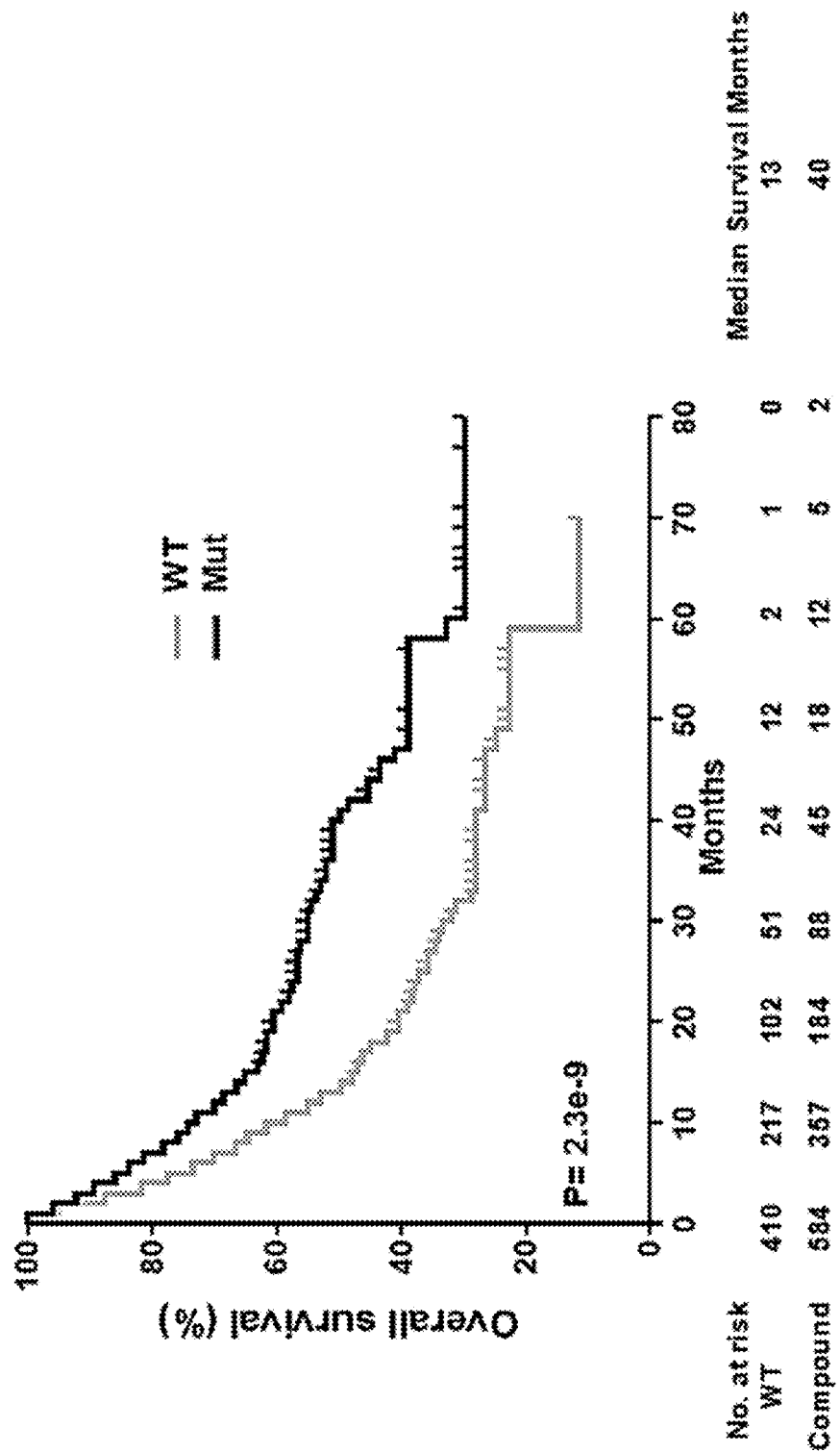
FIG. 4 is a graph showing Kaplan-Meier analysis of OS in patients with one or more mutations in two or more genes from the 42 gene panel in accordance with an embodiment of the present disclosure. HR (compound vs. WT): 0.59 (95% CI: 0.49-0.71).

Identification of a panel of genes whose mutations influenced efficacy of ICB treatment in melanoma, non-small cell lung, bladder, and colorectal cancer patients. To identify genes whose mutations influence ICB treatment efficacy individual cohorts of lung, melanoma, bladder, and colorectal cancer patients and identified a group of 11 genes in each cohort whose mutations were associated with significant clinical benefit. The analysis was focused on mutations and excluded gene fusions. These 4 different gene groups were then combined to obtain a 42-gene panel (Table 1). Among the 994 patients with melanoma, lung, bladder, and colorectal cancer, 584 had mutations in at least one of the 42 genes. Furthermore, these patients achieved significant benefits from ICB treatment, with a median OS at 40 months vs. 13 months, in patients without any mutations in the 42 genes (p=2.3e-9, logrank test; HR: 0.59, 95% CI: 0.49-0.71) (FIG. 4).

Figure 1B:
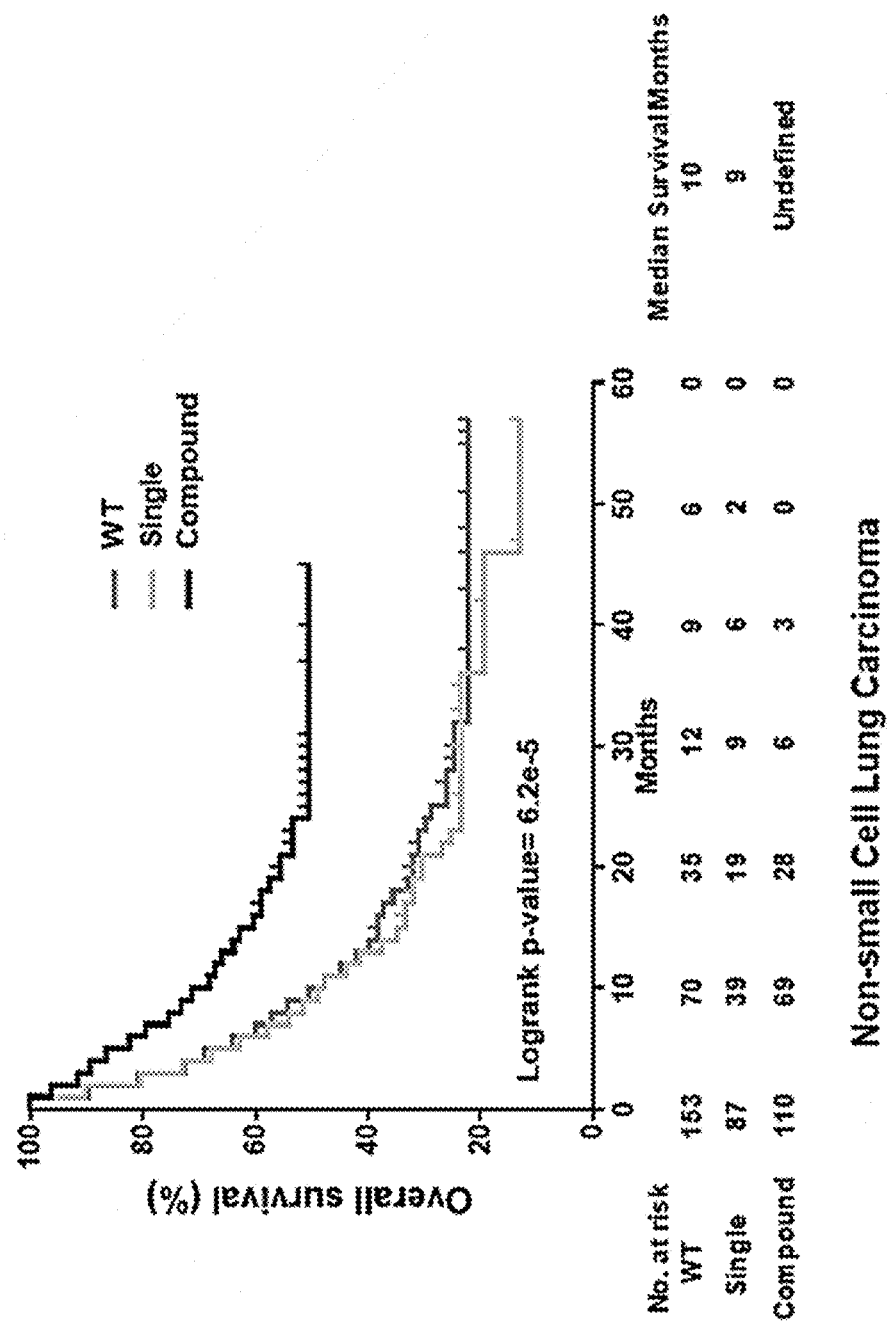
Figure 1C:
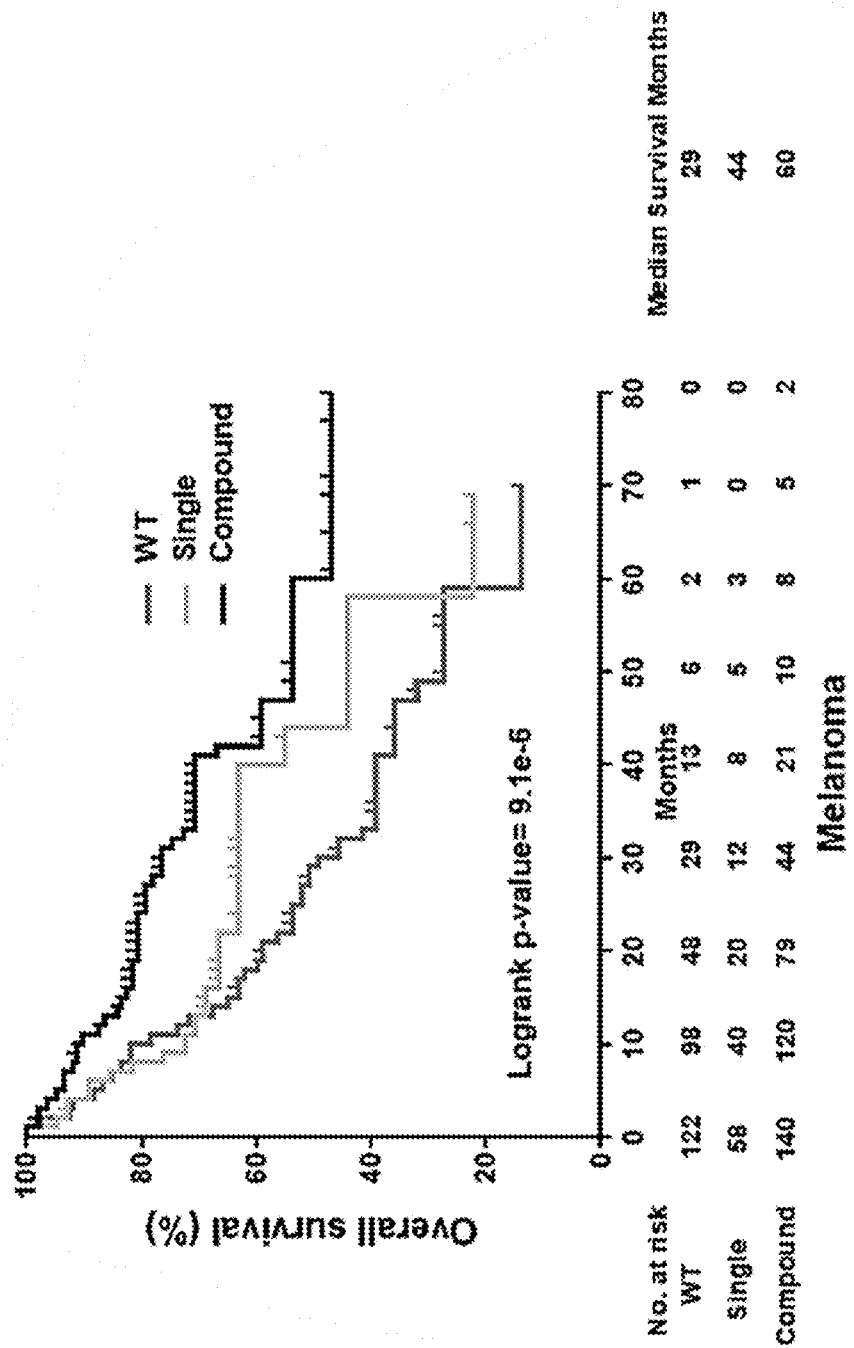
Figure 1D:
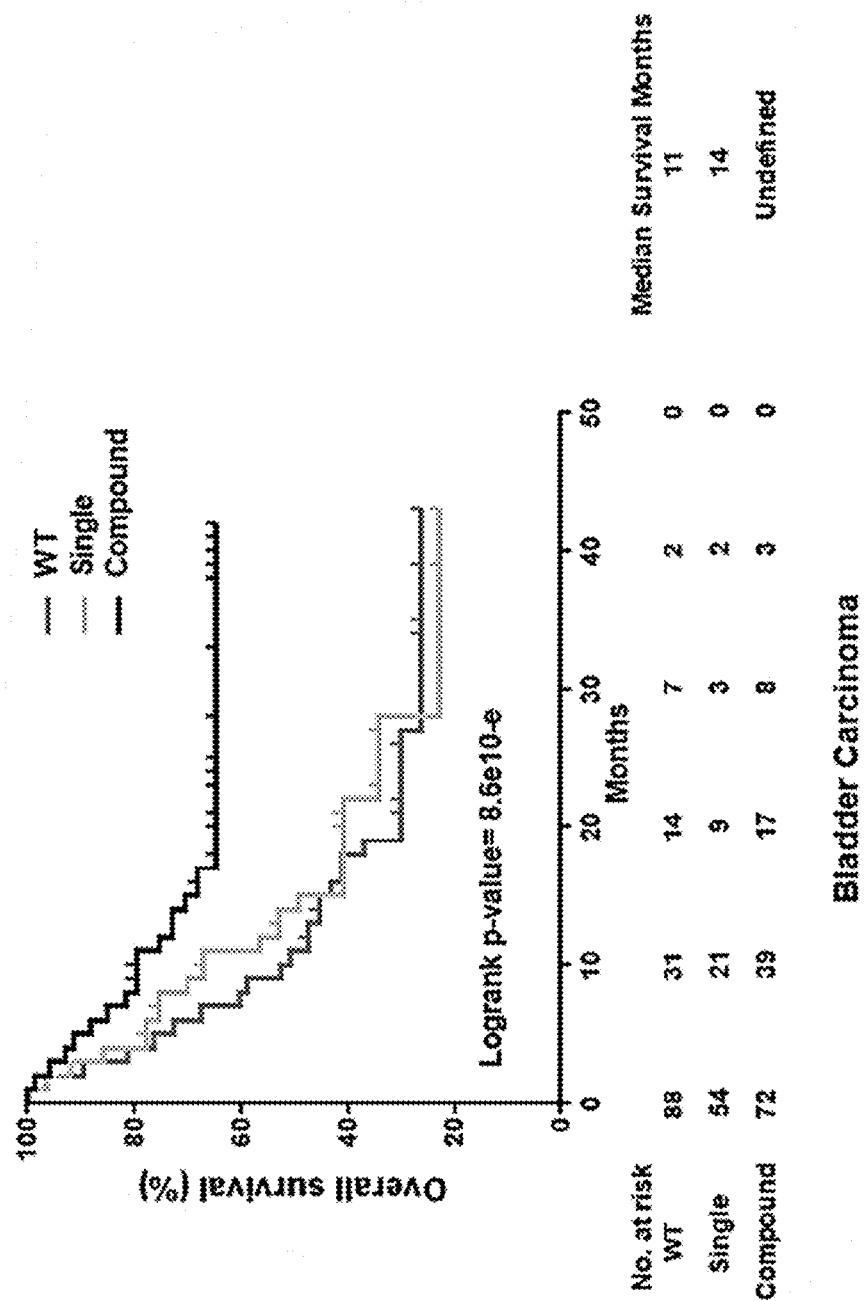
Figure 1E:
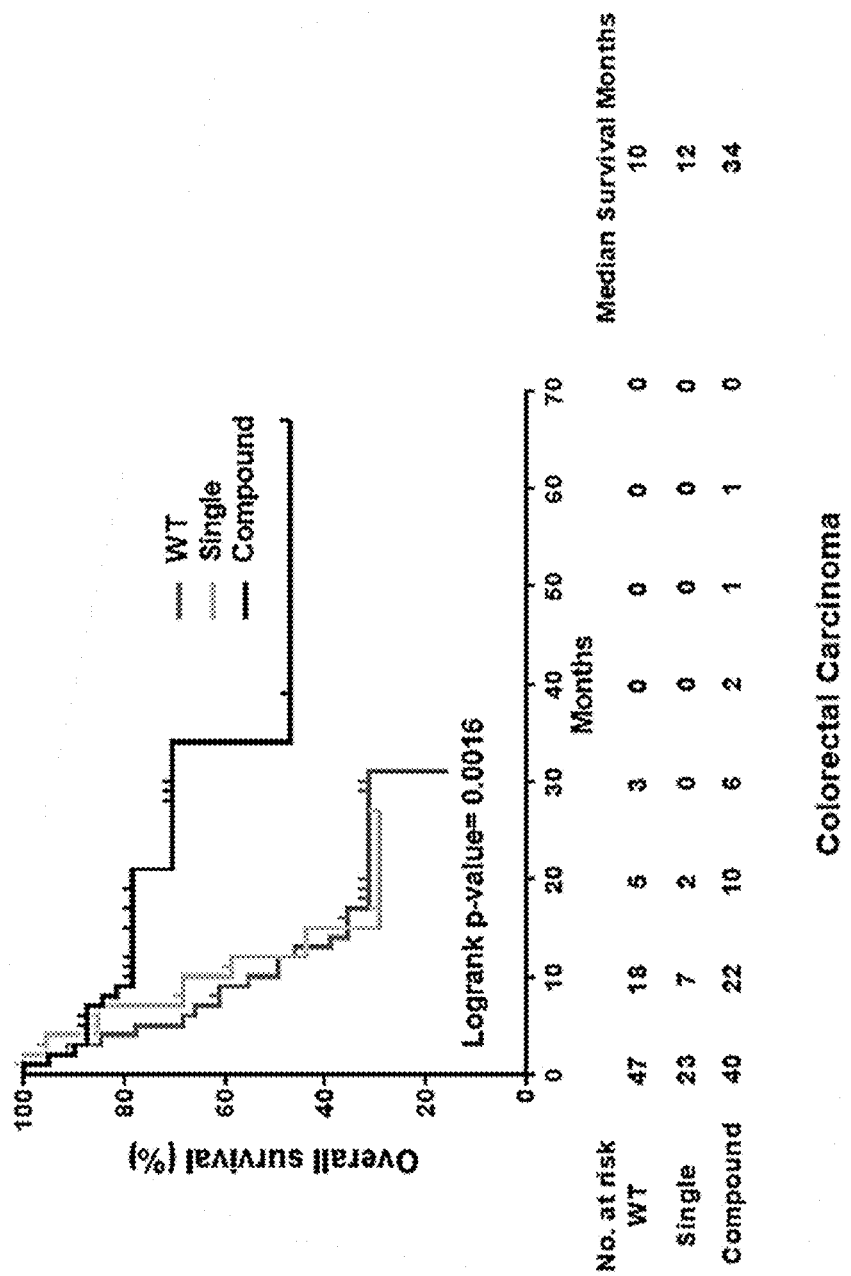
Figure 5A:
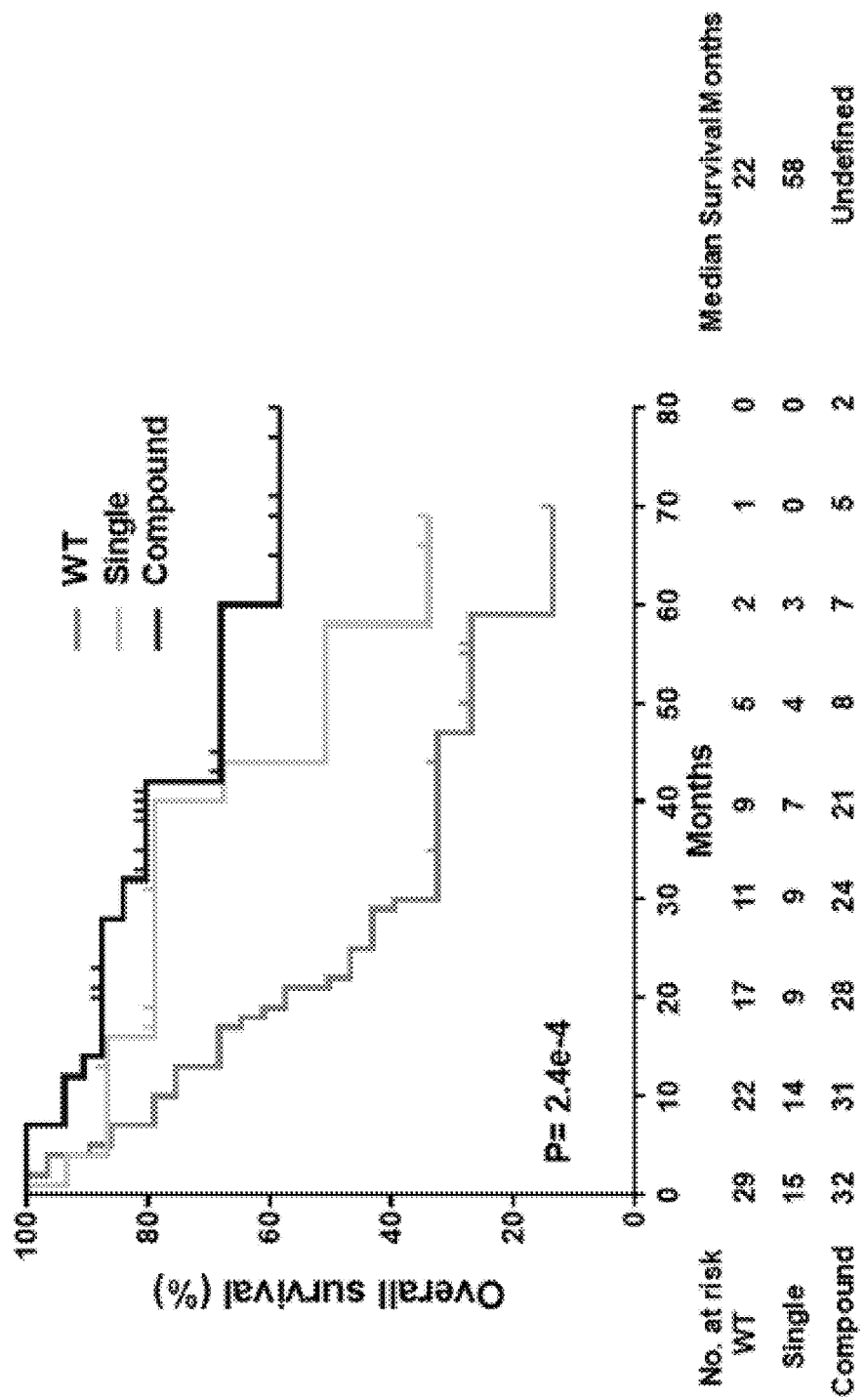
FIGS. 5A-5C are graphs showing the influence of different mutation signatures on OS in patients treated with different checkpoint inhibitors in accordance with an embodiment of the present disclosure.
Figure 5B:
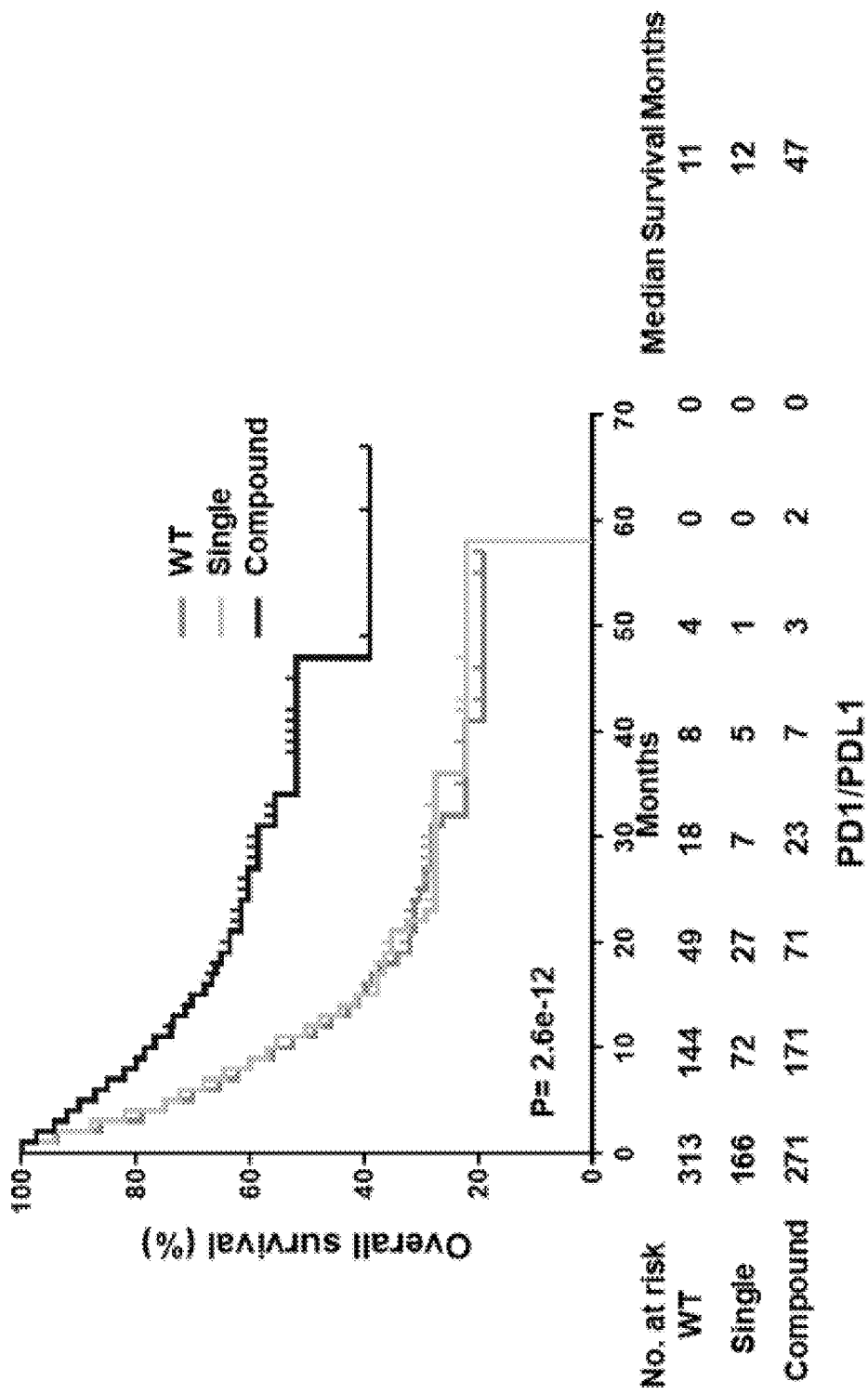
Figure 5C:
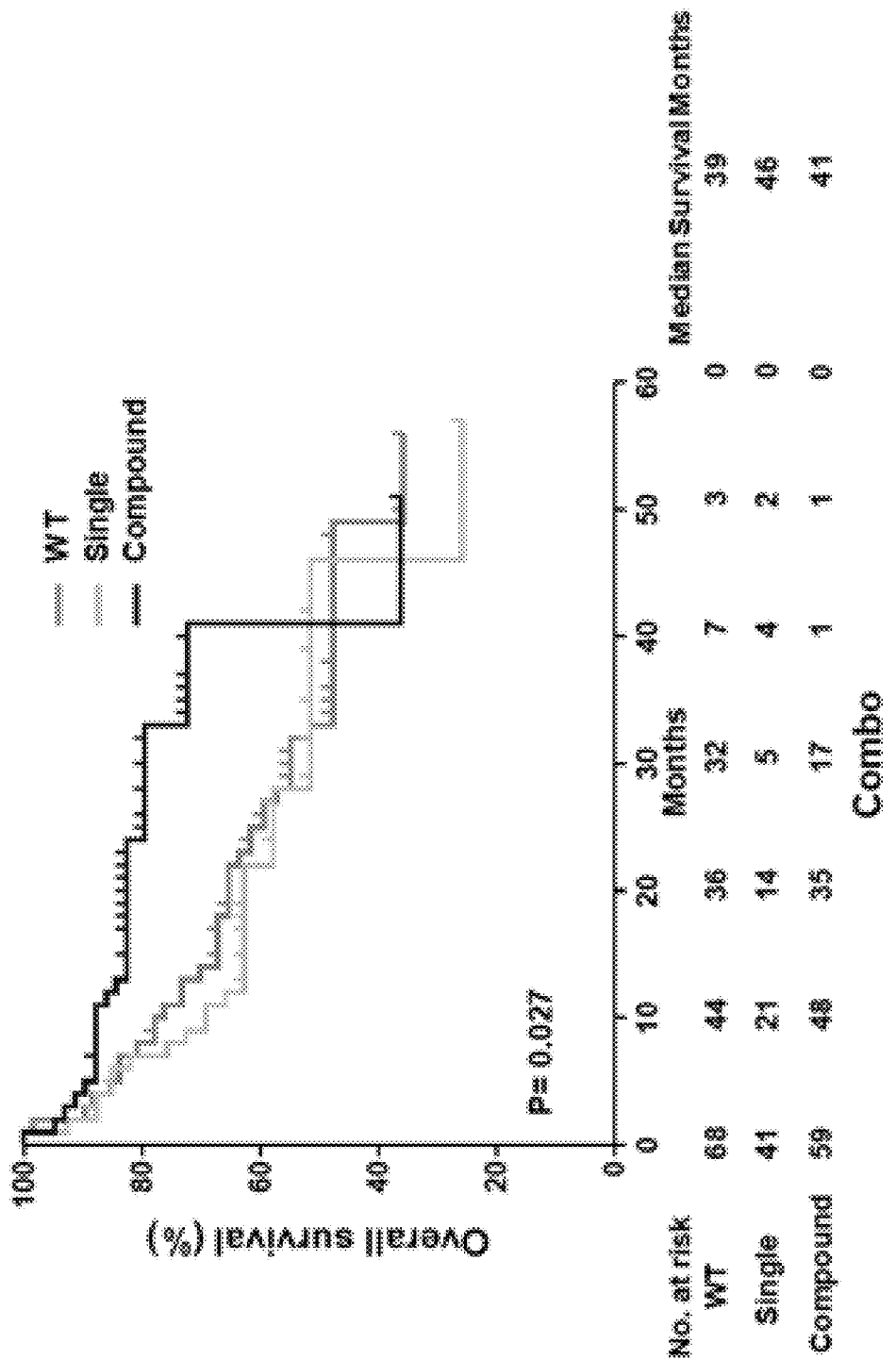

A Compound Mutation Signature in the 42-Gene Panel Predicts for Significantly Better Response to ICB Treatment Whether one can increase the predictive power of mutations in the 42 genes by dividing the melanoma, lung, bladder, and colorectal cancer patients in the MSK-TMB cohorts into the following three sub-cohorts with different mutation signature cohorts: those without mutations in the 42 genes (wt), those with only 1 of the 42 genes mutated (single), and those with 2 or more of the 42 genes mutated (compound), was determined. The OS was compared among the three cohorts (FIG. 1A). The data indicated that the median OS was 47 months among the 410 patients in the compound mutation group (vs. 13 months for wt group, p≤1e-15, logrank test). Importantly, the single mutation group was not significantly different from the wt group in terms of overall survival (p=0.61, log rank test). At the individual cancer level, the median OS times in lung cancer (FIG. 1B), melanoma (FIG. 1C), bladder cancer (FIG. 1D), and colorectal cancer (FIG. 1E) in the compound vs wt groups were unreached vs 10 months, 60 months vs 29 months, unreached vs 11 months, and 34 months vs 10 months, respectively. When patients were stratified according to different immunotherapy treatments, the compound mutation signature was also associated with significantly better OS in those treated with anti-CTLA4 (FIG. 5A), anti-D1/PDL1 (FIG. 5B), and combined anti-CTLA4/anti-PD1/PDL1 (FIG. 5C). These data therefore showed significant overall survival advantages of the compound mutation group when compared with the wt group.

Figure 2:
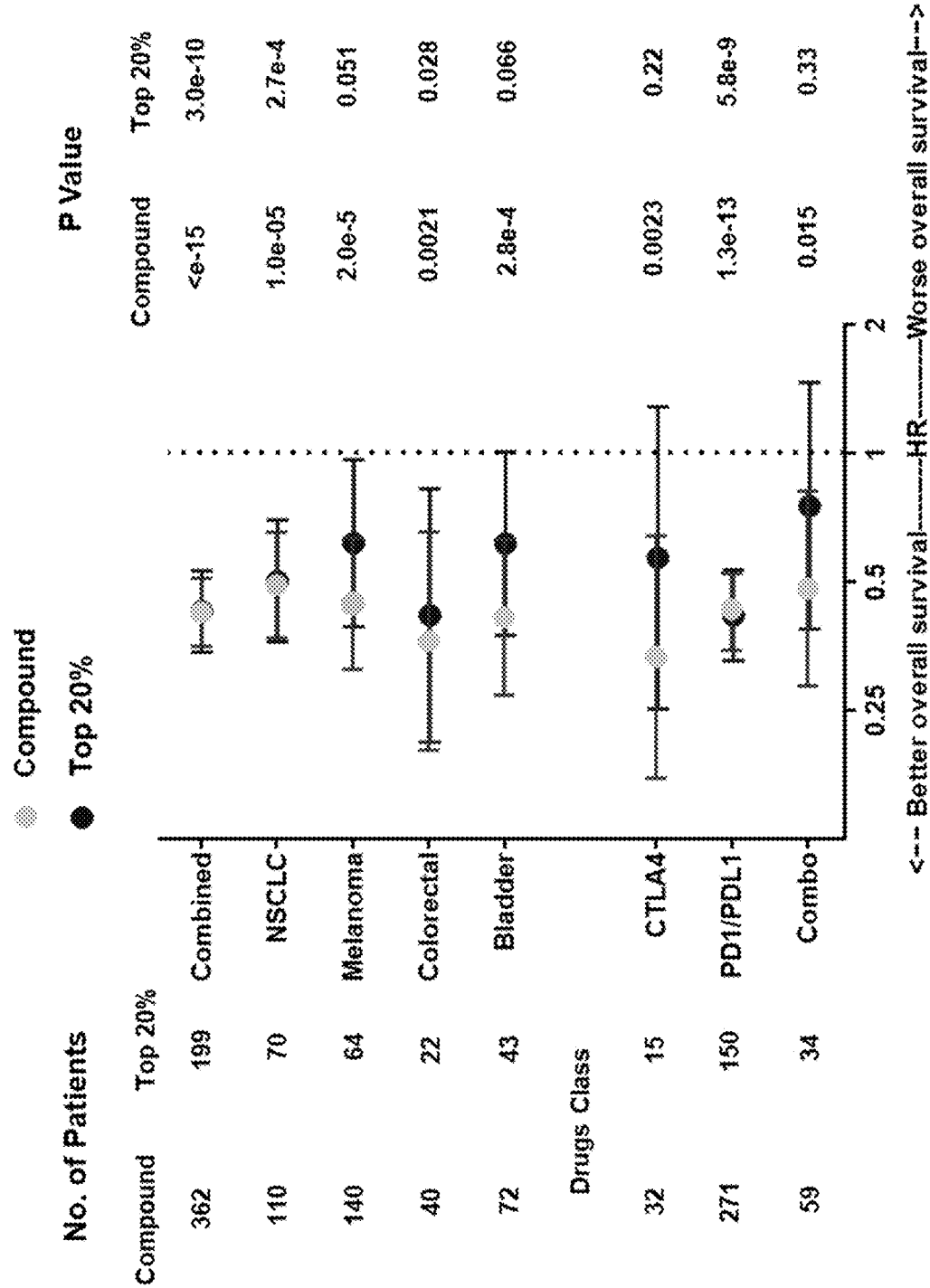
FIG. 2 shows the hazard ratios of overall survival (OS) in ICB-treated patients with the compound mutation signature vs. those with top 20% tumor mutational burden (TMB) in accordance with an embodiment of the present disclosure.

The hazards ratio (HR) values of the compound mutation cohort in the overall and individual cancer cohorts (FIG. 2) were also calculated. The data indicated that the compound mutation cohort had significant survival advantage compared with the rest of the patients in all four cancer types. More importantly, when compared with patients in the top 20% TMB, the compound mutation signature captured more patients and showed either equal or lower HR values (FIG. 2). This was true in both the overall patient cohort and the individual patient cohorts. Furthermore, the p values in each of the individual cancer cohorts were well below 0.05 and in general lower than those within the top 20% TMB groups16 even the latter had less patients.

A compound mutation signature, where two or more of the 42 genes were mutated, was associated with significant ICB treatment benefits in melanoma, NSCKC, bladder, and colorectal cancer patients. Specifically, the median duration of overall survival (OS) was unreached vs 10 months in NSCLC, 60 months vs 29 months in melanoma, unreached vs 11 months in bladder cancer, and 34 months vs 10 months in colorectal cancer, in those with two or more mutations vs no mutations in any of the 42 genes. The median TMBs associated with the two categories of patients were 14.76 vs 3.35 in NSCLC, 25.58 vs 2.95 in melanoma, 18.43 vs 6.88 in bladder cancer, and 54.10 vs 4.39 in colorectal cancer, in the 1,661 patient cohort (P<0.001 in all cases). Similar TMB differentials were also observed in relevant unrelated TCGA Pan-Cancer Atlas cohorts. Furthermore, in an independent group of 109-patient NSCLC cohort the median duration of progression free survival was 8.0 months vs 3.5 months in those with the compound mutation signature vs. none mutated in the 42 genes. In an unrelated cohort of 135 melanoma patients, the median duration of OS was unreached vs 10 months, in the two categories of patients. These results show that, a genetic signature, with mutations in at least 2 of 42 candidate genes, was associated with high TMB and clinical benefits from ICB therapy in NSCLC, melanoma, bladder, and colorectal cancer patients.

Predictive but not Prognostic Nature of the Compound Mutation Signature

Figure 6A:
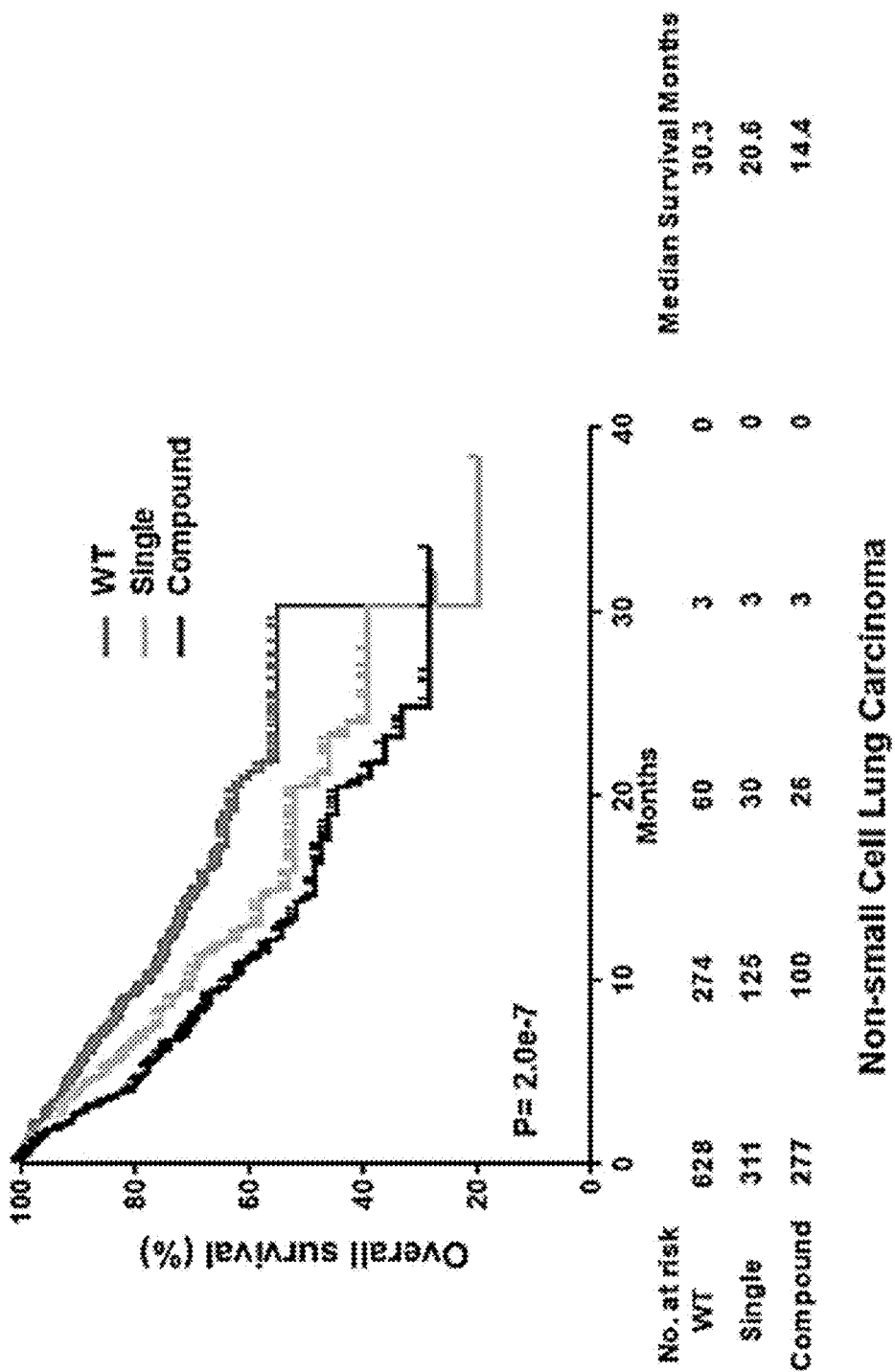
FIGS. 6A-6D are graphs showing the influence of different mutation signatures on OS of non-ICB treated cancer patients in the MSK-IMPACT cohort in accordance with an embodiment of the present disclosure.
Figure 6B:
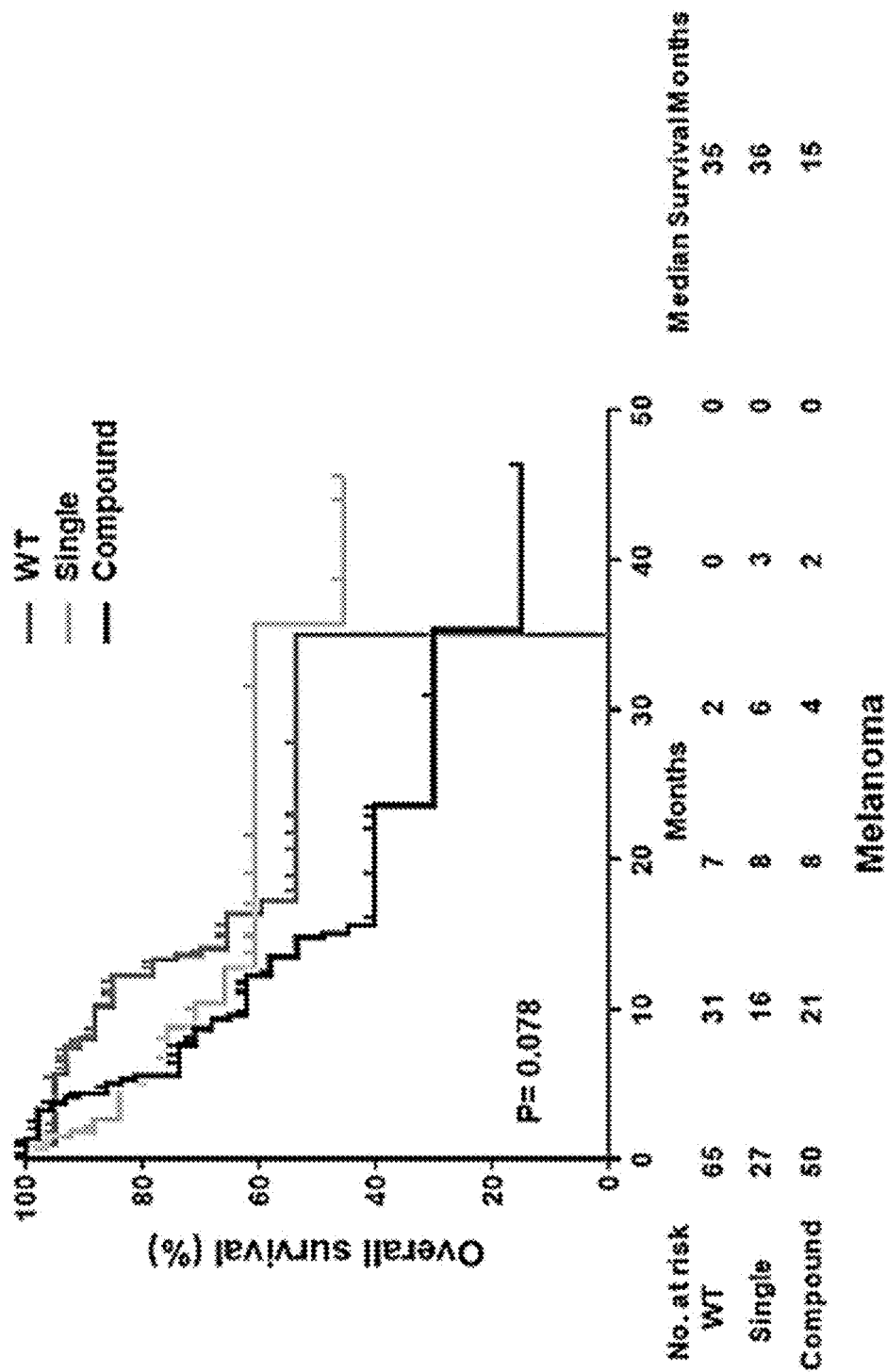
Figure 6C:
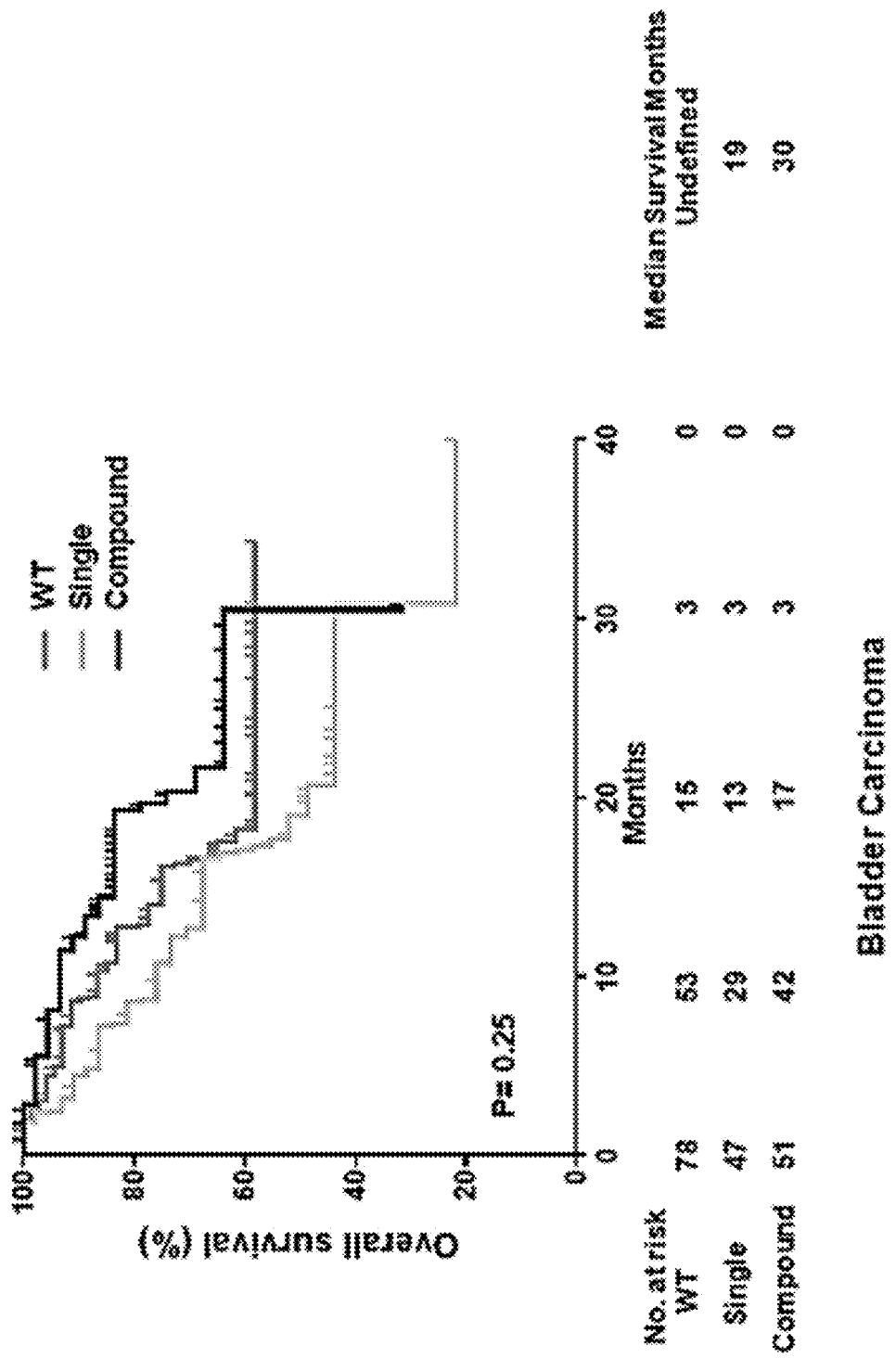
Figure 6D:
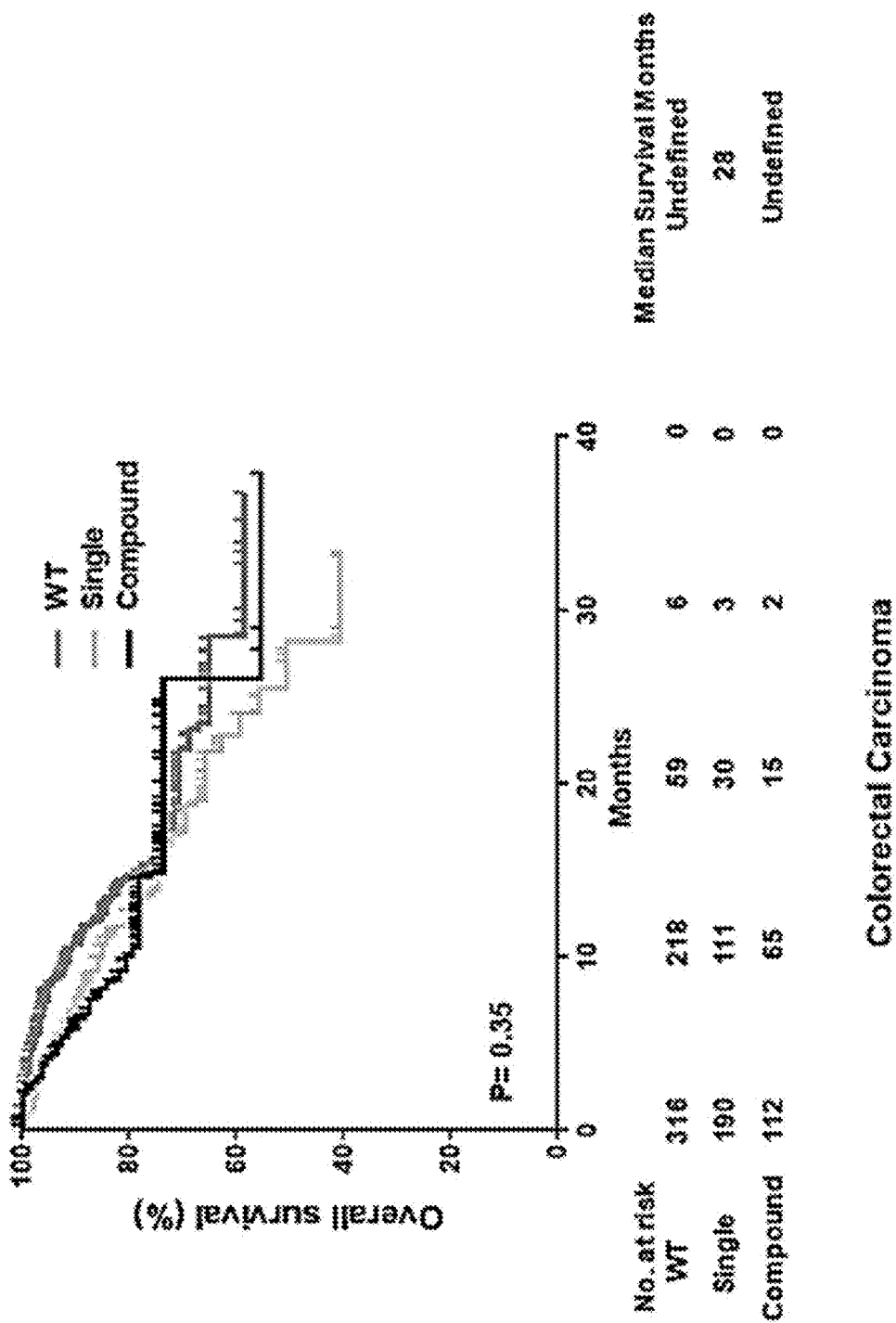

One important question is whether the observed clinical benefits in the compound mutations groups were genetically inherent for the patients and therefore prognostic instead of predictive for the patients. In order to answer this question, non-small cell lung (FIG. 6A), melanoma (FIG. 6B), bladder (FIG. 6C), and colorectal cancer (FIG. 6D) patients, with the compound signature in the MSK IMPACT26 cohort of patents who had not been treated with ICB therapy, were identified. Survival analysis indicated that, in the absence of ICB treatment, the survival benefits observed were reversed (NSCLC, FIG. 6A) or abrogated (melanoma, FIG. 6B; bladder cancer, FIG. 6C; and colorectal cancer, FIG. 6D). Therefore, the compound signature was predictive for ICB therapy instead of prognostic.

Association of the Compound Mutation Signature with High TMB

Figure 7A:
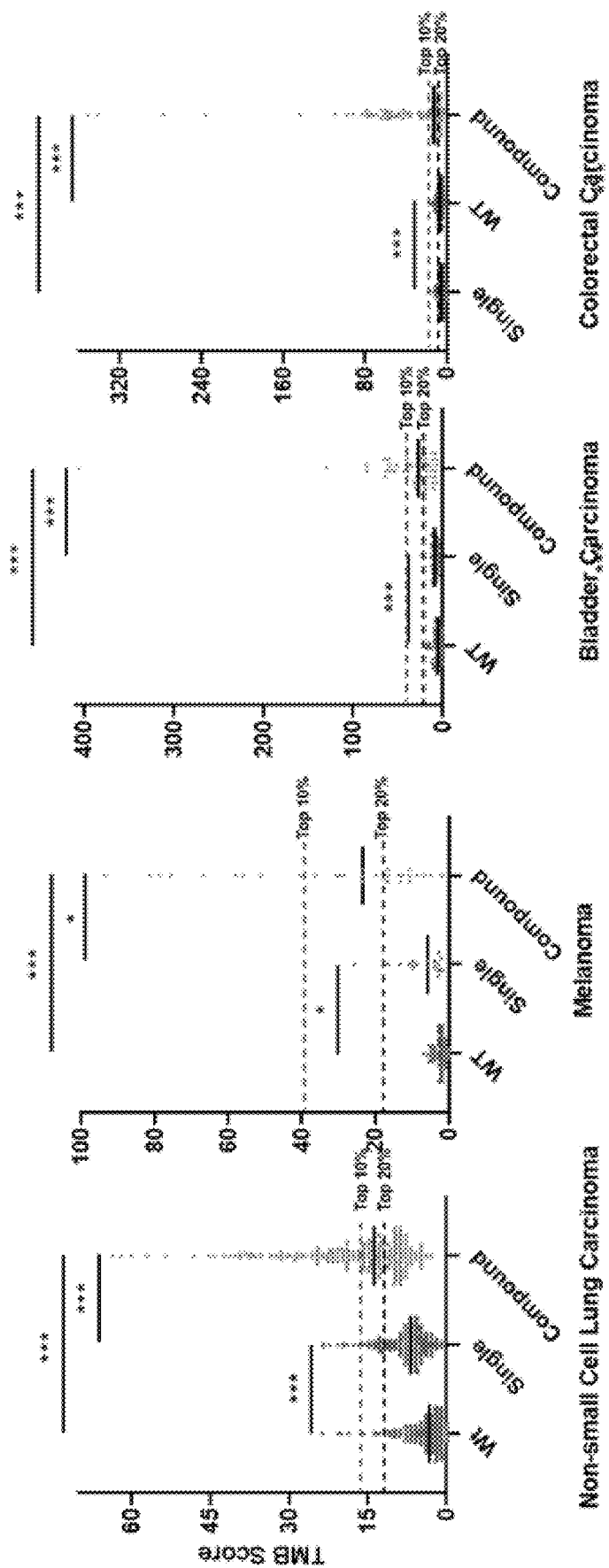
FIGS. 7A-7B are graphs showing TMBs among patients with different mutation signatures in additional melanoma, lung, bladder, and colorectal cancer patients in accordance with an embodiment of the present disclosure.
Figure 7B:
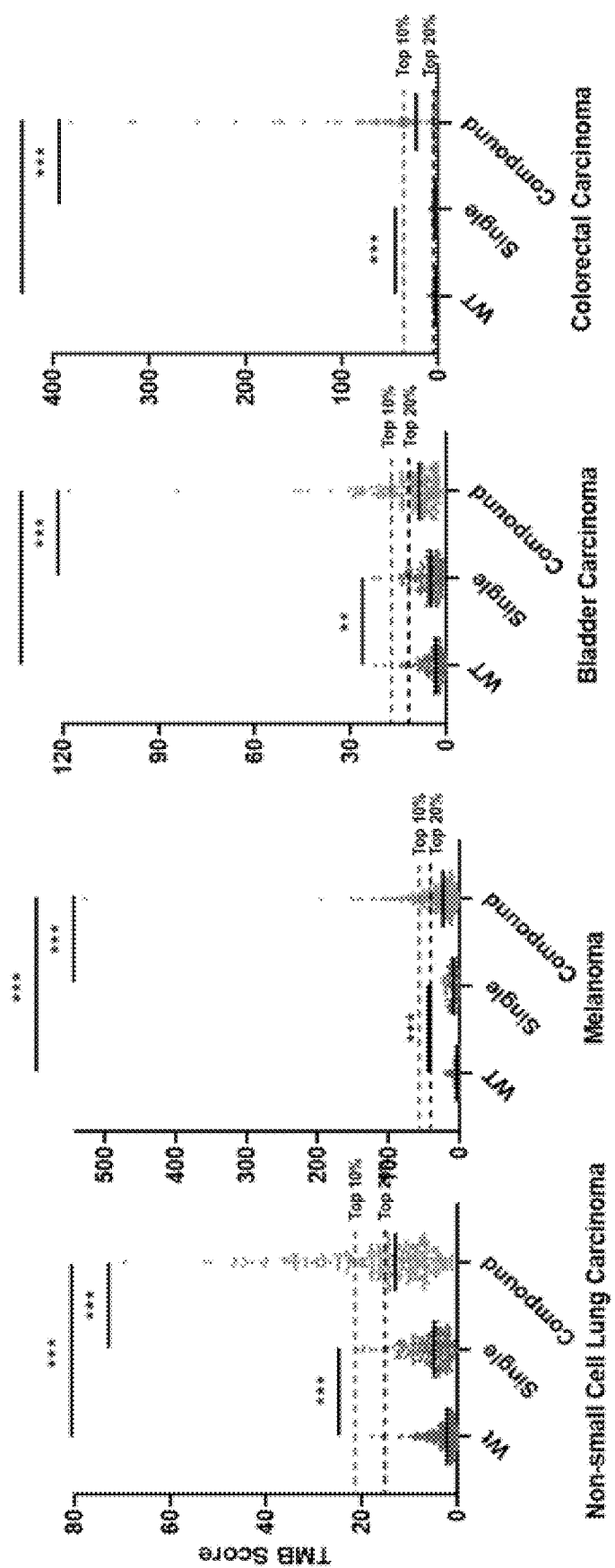

TMB was also calculated in NSCLC, melanoma, bladder, and colorectal cancer patients, with the compound mutation signature in the MSK-TMB cohort. In particular, the distribution of those patients with the compound mutation signature among the top five deciles of TMB was investigated. The analysis showed that the compound mutation signature selected the vast majority patients within the top 30% TMB cohort in all four cancer types. However, there were also patients who fell out the top 50% TMB cohort. Those results therefore suggested that the compound mutation signature preferentially selected patients with high TMB, but also picked those with TMB that were well outside of the top 30% TMB. The TMB distribution among patients with different mutation signatures was also studied. It is interesting to note that the compound mutation group had the highest TMB among the three mutation signatures. Moreover, the median value of TMB in the compound mutation group was just at or above the top 20% TMB cut-off values in lung, bladder and colorectal cancer patients and slightly below in melanoma patients. These observations also held true in non-ICB treated cancer patients in the MSK-IMPACT cohort (FIG. 7A). They also held true in the melanoma, lung, bladder, and colorectal cancer patients in the TCGA Pan-Cancer Atlas cohort, who were sequenced by use of the whole exome sequencing (WES) method (FIG. 7B). Importantly, patients with the highest TMBs in each of the three cohorts fell exclusively within the compound mutation group (FIG. 7A-B), which was surprising given the random nature of gene mutations. This analysis therefore provided compelling evidence that the compound mutation signature preferentially, but not exclusively, select patients with higher TMB.

Figure 8:
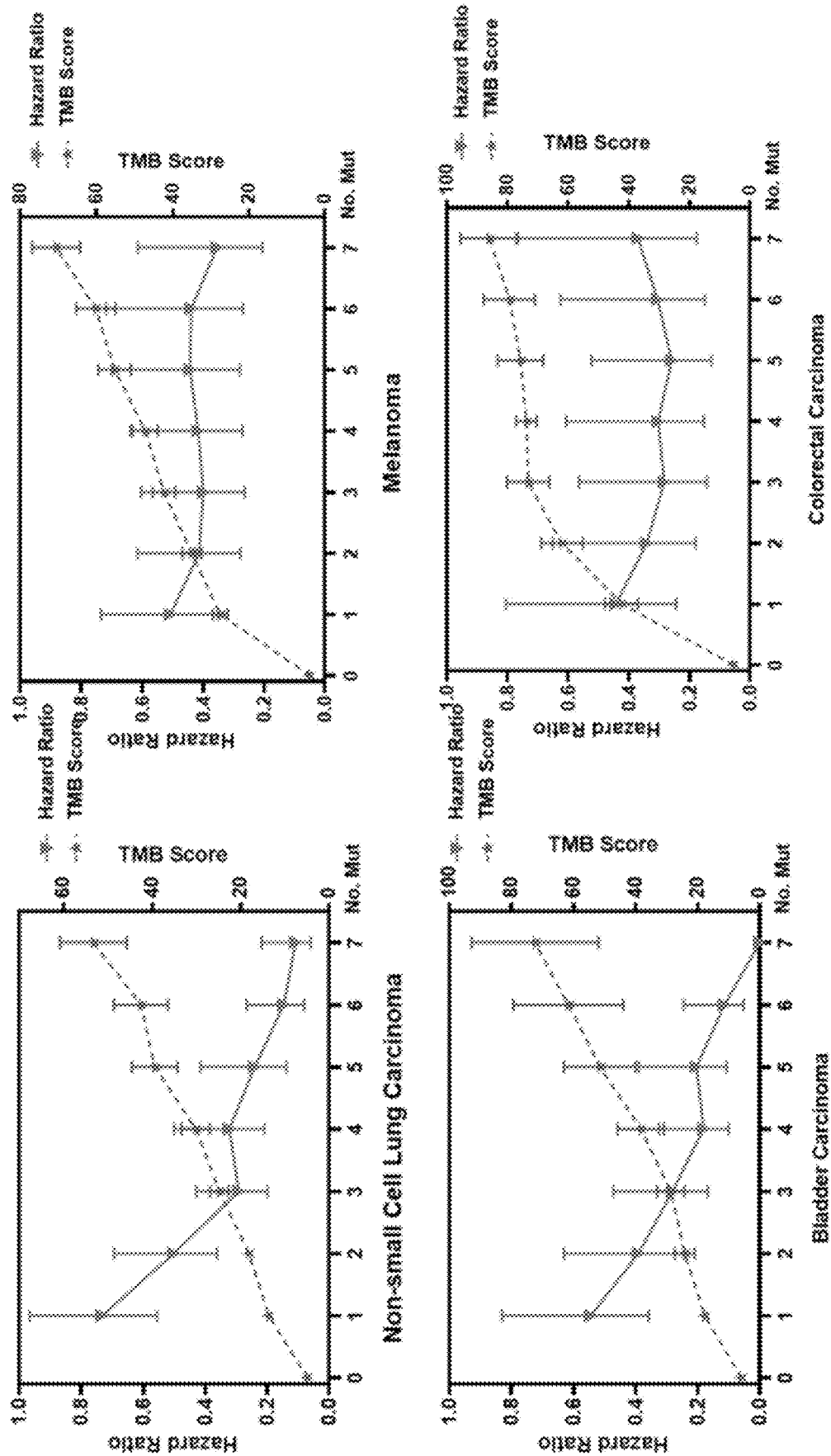
FIG. 8 provides graphs showing correlation of the numbers of mutations in the 42-gene panel with TMB and HR in patients of the MSK-TMB cohort in accordance with an embodiment of the present disclosure. HR ratios were calculated based on comparing the overall survival of those with one or more vs. those with no mutations in the 42-gene panel. TMB values were calculated based on only patients with a particular number of mutations in the 42-gene panel.
Figure 8:
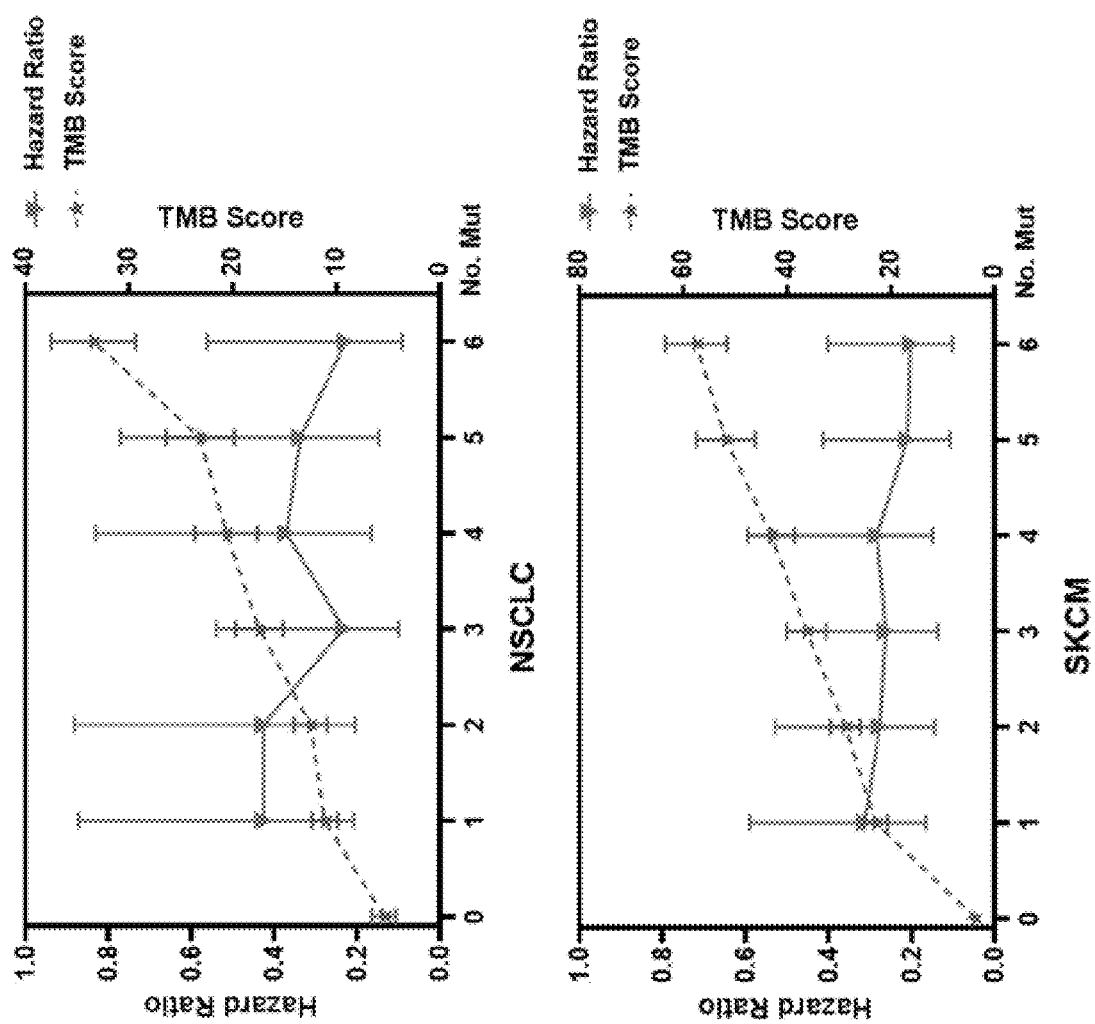

Relationships among the number of mutations in the 42 gene panel, TMB, and hazard ratios of overall survival among the four cancer types in the MSK-TMB cohort, were also examined. The data indicated that, with increasing number of mutations in the 42-gene panel, overall TMB increased almost linearly in all four cancer subtypes (FIG. 8). On the other hand, the HR values of overall survival in the compound mutation group decreased lineally in NSCLC and bladder cancer patients, and trended down in a non-linear fashion in melanoma and colorectal cancer patients (FIG. 8).

Validation of the Predictive Power of the Compound Mutation Signature in Unrelated Cohorts of ICB Treated Cancer Patients.

Figure 3A:
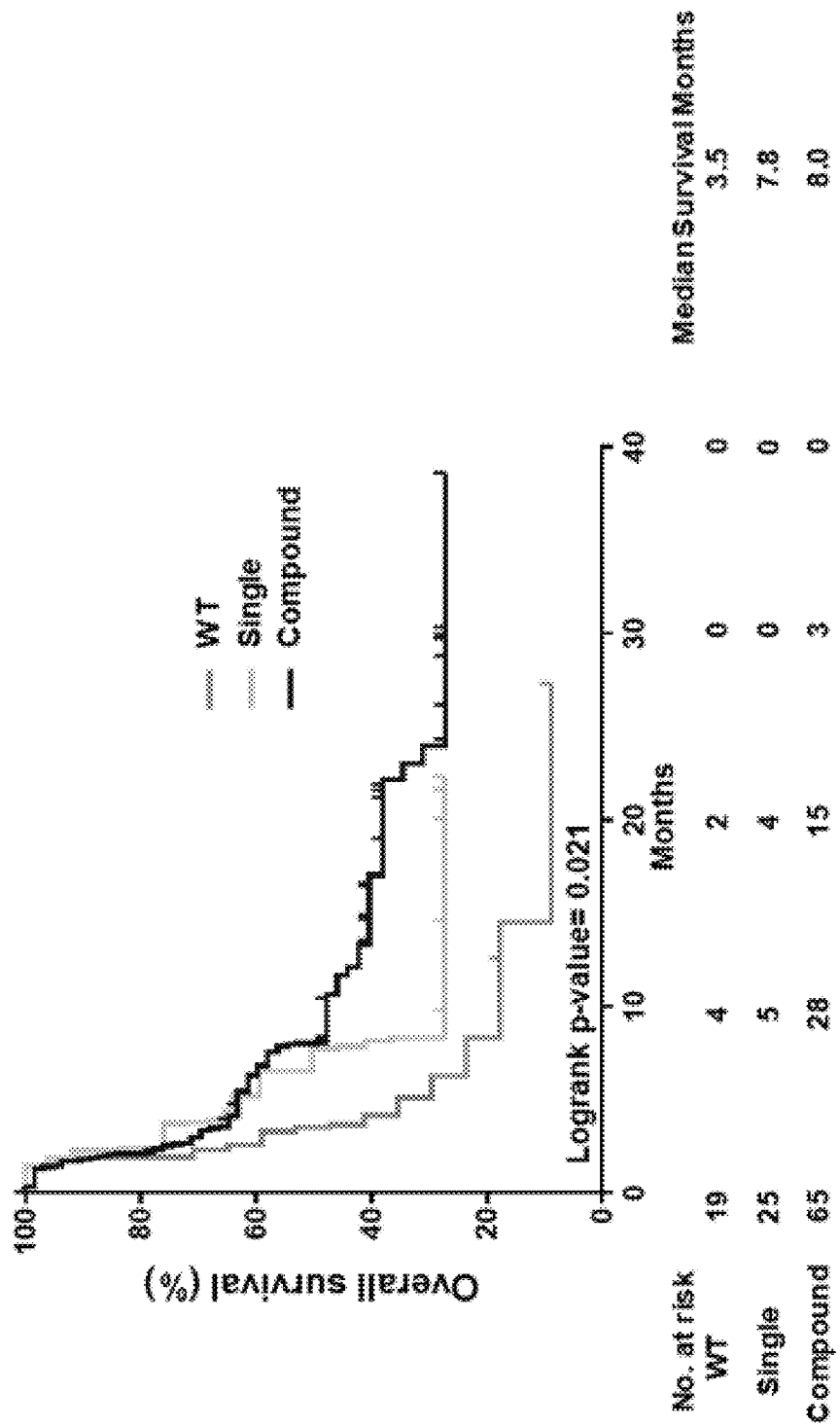
FIGS. 3A-3B are survival curves showing the survival analysis of independent cohorts of ICB-treated patients with different mutation signatures in accordance with an embodiment of the present disclosure.
Figure 3B:
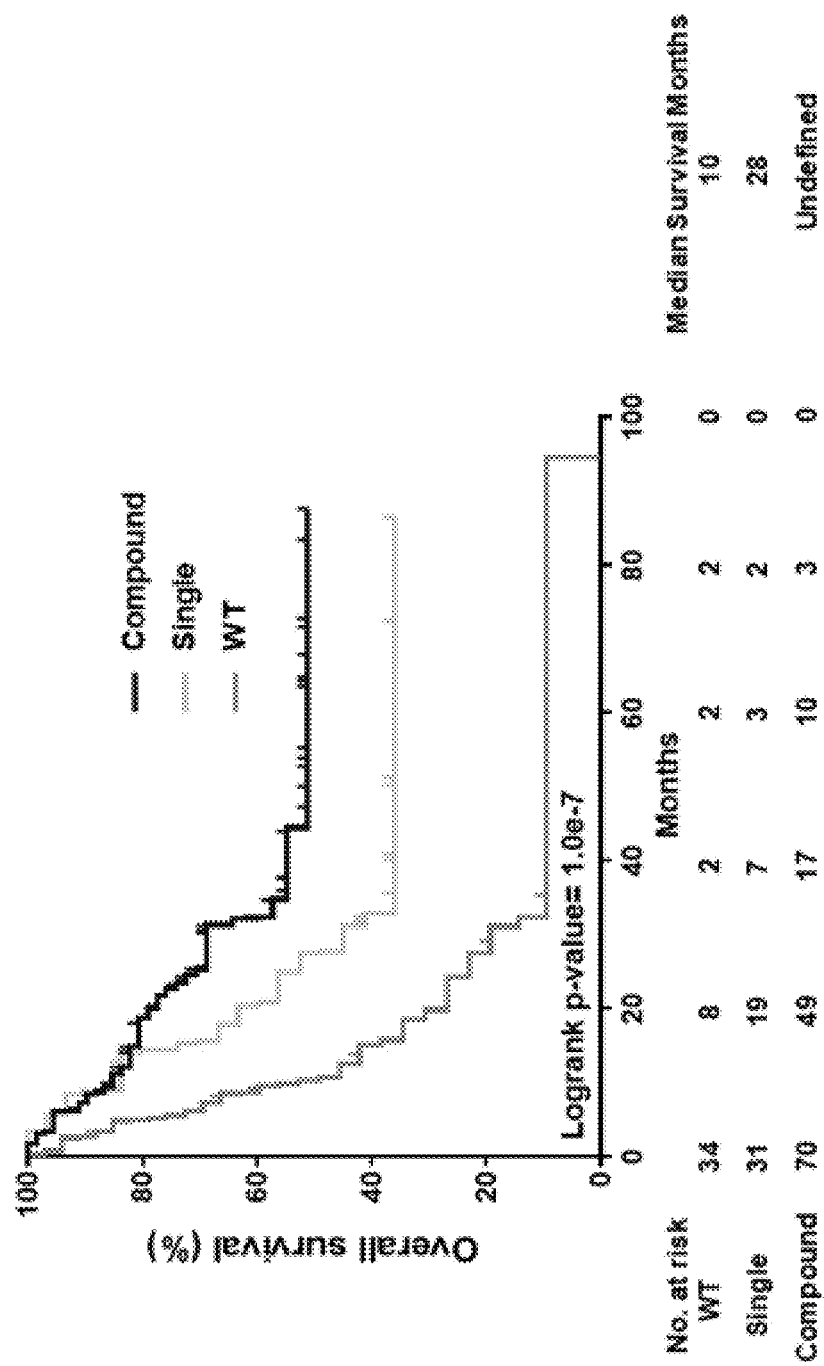

In order to further evaluate the predictive power of the compound mutation signature in predicting clinical benefits for ICB treatment, independent cohorts of NSCLC and melanoma patients, that had been treated with ICB and characterized with WES for gene mutations, were studied. When comparing OS in patients with different mutation signatures in the 42-gene panel, the compound mutation signature in both the NSCLC (FIG. 3A) and melanoma (FIG. 3B) cohorts of patients showed significant survival advantages. Furthermore, the compound mutation signature was also associated with significantly higher levels of TMB (FIG. 9A-B). These results therefore recapitulated the observations in the MSK TMB cohort (FIG. 1).

Figure 10:
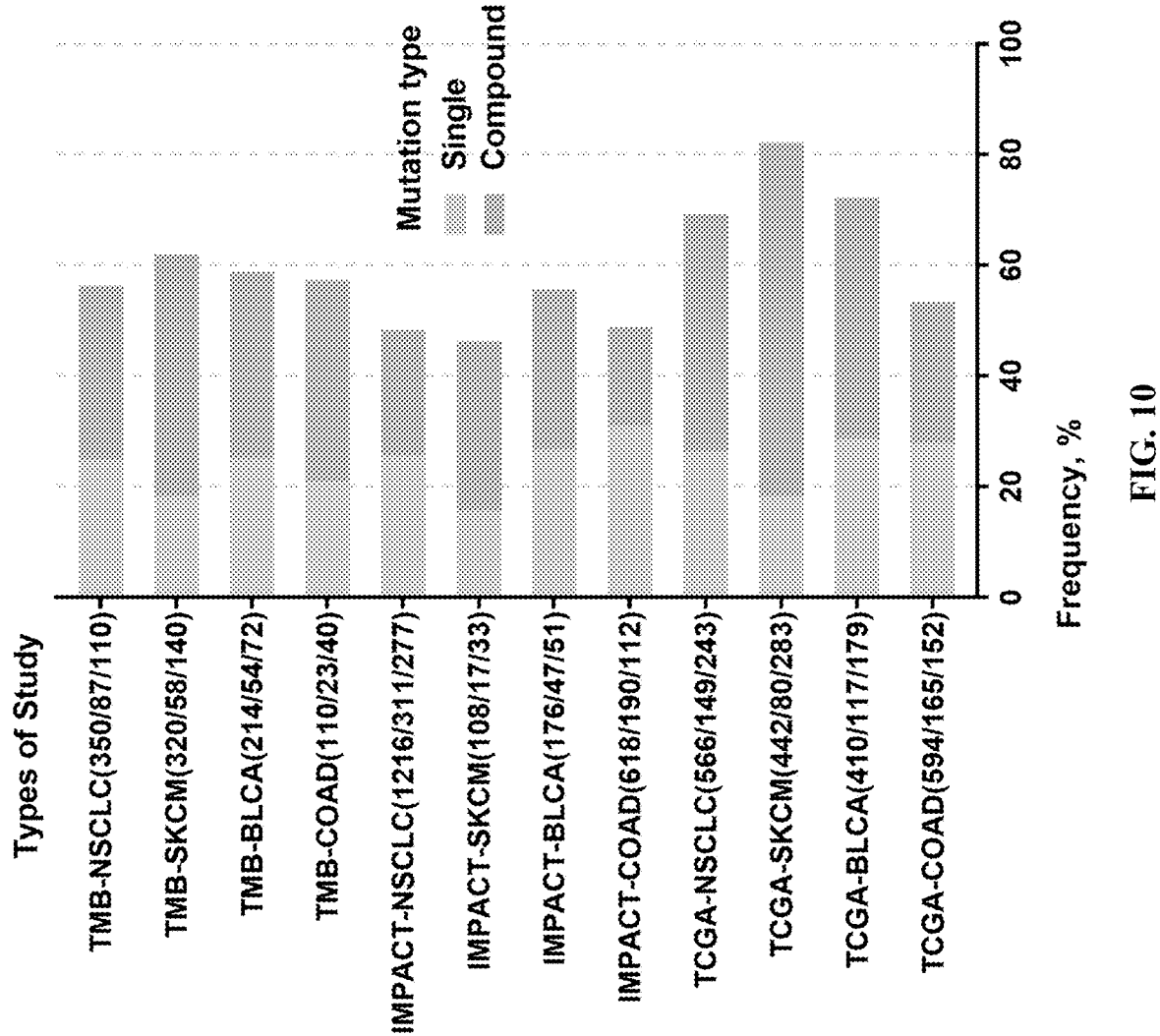
FIG. 10 is a graph showing the prevalence of single and compound mutation signatures in MSK-TMB, MSK-IMPACT, and TCGA cohorts of cancer patients in accordance with an embodiment of the present disclosure.

Incidence of the Compound Mutation Signature Among the General Cancer Patient Population To assess the prevalence of the compound mutation signature in the general cancer population, the incidence of the compound mutation signature in the 4 cancer types among the MSK-TMB cohort, the MSK-IMPACT cohort, and the TCGA Pan-cancer Atlas cohorts (FIG. 10) was surveyed. Results indicated that there were variations in incidences of compound mutations among different cancer types in the three large cohorts. When pooled together, the incidences of the compound mutation signature were 29.5% for NSCLC, 49.0% for melanoma, 37.8% for bladder cancer, and 23.0% for colorectal cancer. These data therefore indicate that the compound mutation signature can capture significant fractions of patients among the four cancer types.

Although there is an abundance of evidence to associate high TMB with response to ICB treatment, the use of TMB as a biomarker in the clinic has been hampered by the lack of clearly defined cut-offs because of the great variability in TMB among different cancer types. The findings provided herein, i.e., that the compound mutation signature in the 42 gene panel predicted ICB therapy response at a comparable or more favorably rate than top 20% TMB was therefore significant. Provided herein is strong evidence from a large patient database that the compound mutation signature could be used as a biomarker for selecting patients suitable for ICB therapy, much like the well-established MSI assay. The predictive power of the compound mutation signature is likely do to the fact that it encompasses both high TMB and gene mutations that are functionally relevant for ICB treatment. In addition, the compound mutation signature also captures those patients with relatively lower TMB, but nonetheless respond to ICB treatment. These attributes make the compound mutation signature a superior biomarker than TMB alone. At a practical level, the compound mutation signature as a predictive biomarker has significant advantages.

In conclusion, the studies described herein revealed that a compound mutational signature wherein two or more genes of a 42-gene panel are mutated predicted for high TMB and response to ICB therapy.

Example II

Gene Mutation Signature in Non-Small Cell Lung Cancer Patients

Identification of patients who can benefit from ICB therapy is key for improved clinical outcome. Recently, the US FDA approved tumor mutational load high (TMB-H, or TMB≥10) as a biomarker for pembrolizumab treatment of solid tumors. Whether mutations in select genes may be a better predictor of non-small cell lung cancer (NSCLC) response to ICB therapy than TMB-H was examined.

Source of Patient Treatment and Mutation Data

All patient data were previously published and obtained from the cBioPortal database (cbioportal.org), which includes more than 160 studies from The Cancer Genome Atlas (TCGA), International Cancer Genome Consortium (ICGC), Memorial Sloan-Kettering Cancer Center (MSKCC) and other sources within the timeframe of this study (Nov. 17, 2019-Jul. 15, 2020).

Candidate genes that might influence ICB treatment of NSCLC were identified by using data from a recently published cohort of patients treated with ICB therapy at the Memorial Sloan Kettering Cancer Center (MSKCC) (Samstein et al. Tumor mutational load predicts survival after immunotherapy across multiple cancer types. Nat Genet 2019; 51:202-206). It included 1661 patients who underwent ICB treatment and this cohort was referred to as the MSK-TMB cohort. Mutation and survival data from some of the lung cancer patients in the 10,336-patient MSK-IMPACT Clinical Sequencing Cohort was also studied. Mutations in both the MSK-TMB and MSK-IMPACT cohorts were derived by several different versions of the IMPACT targeted sequencing assay (Samstein et al.; Zehir et al. Mutational landscape of metastatic cancer revealed from prospective clinical sequencing of 10,000 patients. Nat Med 2017; 23:703-713; Cheng et al. Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology. J Mol Diagn 2015; 17:251-264).

In addition to patient clinical and genomic data from the MSK-TMB and MSK-IMPACT cohorts, data from several other published studies on ICB treatment of NSCLC was used (Rizvi et al. Cancer immunology. Mutational landscape determines sensitivity to PD-1 blockade in non-small cell lung cancer. Science 2015; 348:124-12828; Zehir et al.; Hellmann et al. Genomic Features of Response to Combination Immunotherapy in Patients with Advanced Non-Small-Cell Lung Cancer. Cancer Cell 2018; 33:843-852 e844 37; and Rizvi et al. Molecular Determinants of Response to Anti-Programmed Cell Death (PD)-1 and Anti-Programmed Death-Ligand 1 (PD-L1) Blockade in Patients With Non-Small-Cell Lung Cancer Profiled With Targeted Next-Generation Sequencing. J Clin Oncol 2018; 36:633-641), to validate the predictive power of the candidate genes. Additional tumor mutation and transcriptome profiling data were obtained from NSCLC patients in the TCGA Pan-Cancer Atlas cohort (Hoadley et al. Cell-of-Origin Patterns Dominate the Molecular Classification of 10,000 Tumors from 33 Types of Cancer. Cell 2018; 173:291-304 e296).

Mutation Signatures and Survival Analysis

To analyze if mutations in 52 candidate genes could predict ICB treatment efficacy, patients were grouped into those with no mutations in the 52 genes (wild type, or wt group), those with mutations in one or more of the 52 genes (mut group), those with only a single mutation in any of the 52 genes (single mutation, or single mut group), and those with 2 or more mutations in the 52 genes (compound mutation, or compound mut group). Overall or progression-free survival of patients with different mutation signatures were then compared in the MSK-TMB and additional cohorts.

The Relationship Between the Compound Mutation Signature and PD-L1 Expression

The potential interactions between PD-L1 expression and the compound mutation signature in influencing patient response to ICB therapy was analyzed, by examining a sub-cohort of the MSK-TMB NSCLC cohort that was published. Kaplan-Meier survival analysis was conducted of patients stratified by both their mutation signature and PD-L1 expression levels (Rizvi et al., (2018).

CIBERSORT Estimate of the Intratumoral Lymphocyte Infiltration

To determine if different mutation signatures correlate with specific characteristics of the tumor microenvironment, CIBERSORT analysis of NSCLC patients, based on their RNA expression data, was carried out (Newman et al. Robust enumeration of cell subsets from tissue expression profiles. Nat Methods 2015; 12:453-457). An published online tool, TIP (Xu et al. Cancer Research, 78(23): 6575-6580 (2018) based on CIBERSORT principles, was used for the immune cell subset analysis of the tumor samples.

Statistical Analysis

For survival analysis, Kaplan-Meier survival curves were generated by use of the statistical software GraphPad Prism (version 8.2). Nonparametric Mantel-Cox logrank test was used to determine the differences among different patient groups. Hazards ratio (HR) and the 95% confidence interval (CI) were calculated by use of the logrank (Mantel-Cox) test and adopting the Cox proportional-hazards model.

Results

It was hypothesized that gene mutations not only produced neoantigens, but also could functionally affect the outcome of immunotherapy. Based on this hypothesis, identification of genes whose mutations could positively influence ICB treatment efficacy were identified by investigating 350 NSCLC patients among a recently published cohort of ICB-treated patients (Samstein et al.) See Table 2 for patient information.

TABLE 2

Patient characteristics in the MSK-TMB cohort

| NSCLC patient characteristics | WT N = 120 | Single N = 85 | Compound N = 145 | P value (Compound VS WT) |
|---|---|---|---|---|
| Median age (range, SEM), years | 65 ± 1.1 | 69 ± 1.1 | 67 ± 0.8 | 0.051* |
| Sex, n (%) | | | | |
| Male | 56, (47%) | 47, (55%) | 67, (46%) | 0.94 |
| Female | 64, (53%) | 38, (45%) | 78, (54%) | |
| Smoking History | | | | |
| Prev/Curr, n (%) | 57, (48%) | 46, (53%) | 102, (70%) | 2.0e−5 |
| Never, n (%) | 25, (21%) | 13, (15%) | 7, (5%) | |
| Unknown, n (%) | 28, (31%) | 26, (32%) | 36, (25%) | |
| Cancer Type | | | | |
| Lung Adenocarcinoma, n (%) | 98, (82%) | 59, (69%) | 114, (78%) | 0.77 |
| Lung Squamous Cell Carcinoma, n (%) | 15, (13%) | 17, (20%) | 17, (12%) | |
| Poorly Differentiated Non-Small Cell Lung Cancer, n (%) | 3, (2%) | 3, (4%) | 7, (5%) | |
| other, n (%) | 4, (3%) | 6, (7%) | 7, (5%) | |
| Sample Type | | | | |
| Primary, n (%) | 65, (54%) | 37, (44%) | 69, (48%) | 0.28 |
| Metastasis, n (%) | 55, (46%) | 48, (56%) | 76, (52%) | |
| Overall Survival Status | | | | |
| Living, n (%) | 24, (20%) | 26, (31%) | 81, (56%) | 2.8e−9 |
| Deceased, n (%) | 96, (80%) | 59, (69%) | 64, (44%) | |

TABLE 2-continued

Patient characteristics in the MSK-TMB cohort

| NSCLC patient characteristics | WT N = 120 | Single N = 85 | Compound N = 145 | P value (Compound VS WT) |
|---|---|---|---|---|
| PD-L1 expression | | | | |
| 0%, n (%) | 13, (11%) | 6, (7%) | 13, (9%) | 0.19 |
| ≥1%, n (%) | 9, (8%) | 7, (8%) | 21, (15%) | |
| Unknown, n (%) | 98, (81%) | 72, (85%) | 111, (76%) | |
| Median TMB Score (range, SEM), | 3.94 ± 0.29 | 6.89 ± 0.50 | 12.79 ± 1.04 | <e-16* |
| Drug Type | | | | |
| PD-1/PDL-1, n (%) | 111, (93%) | 81, (95%) | 137, (95%) | 0.51 |
| PD-1/PDL-1&CTLA4, n (%) | 9, (7%) | 4, (5%) | 8, (5%) | |

*P values were calculated by use of unpaired t-test. Other P values were calculated by use of Chi-Squared Test.

These patients were sequenced with the MSK-IMPACT targeted sequencing panel (Zehir et al.; Cheng et al.), which contained around 400 genes known to be involved in cancer development. To compile the list of candidate genes, the following criteria were used: 1) the gene has to be mutated in at least 3 or more cancer patients (out of a total of 350); 2) mutations in the gene have to be correlated with a survival benefit, e.g. its mutation frequency has to be significantly higher among the surviving patients (at the end of clinical observation period) than that among the deceased patients (with a p value≤0.10 instead of p<0.05 due to small number of patients for some genes). The focus was on nonsysnomous mutations, as gene fusions and amplifications were excluded. Applying these criteria to the targeted sequencing gene panel used in the study, a 52 gene panel was obtained. The genes and their corresponding GenBank Accession Nos. are set forth below in Table 3. Among the 350 NSCLC patients, 230 had mutations in at least one of the 52 genes.

TABLE 3

52 genes whose mutations influence immuotherapy outcomes.
Gene name (% with mutations in MSK-TMB-NSCLC cohort)
and GenBank Accession Nos.

| Gene Name | GenBank Accession No. |
|---|---|
| ABL1(2.0%), | NG_012034.1 |
| ASXL1(3.4%), | NG_027868.1 |
| ATM(6.6%), | NG_009830.1 |
| BCOR(4.0%), | NG_008880.1 |
| BRCA2(4.3%), | NG_012772.3 |
| BRIP1(3.7%), | NG_007409.2 |
| CARD11(4.0%), | NG_027759.1 |
| CD79B(1.4%), | NG_007368.1 |
| CDC73(0.9%), | NG_012691.1 |
| CIC(3.7%), | NG_042060.1 |
| EPHA3(10.6%), | NC_000003.12 |
| EPHA5(8.3%), | NM_001281765.3 |
| EPHA7(5.1%), | NG_033944.1 |
| EPHB1(3.7%), | NM_004441.5 |
| ERBB4(6.0%), | NG_011805.2 |
| ERCC4(2.0%), | NG_011442.1 |
| FGFR4(2.6%), | NG_012067.1 |
| FLT3(2.6%), | NG_007066.1 |
| FOXL2(1.4%), | NG_012454.1 |
| HGF(6.3%), | NG_016274.2 |
| INHBA(2.9%), | NM_002192.4 |
| JAK3(3.1%), | NG_007273.1 |
| MAX(2.0%), | NG_029830.1 |
| MDC1(4.0%), | NM_014641.3 |
| MED12(3.4%), | NG_012808.1 |
| MET(4.0%), | NG_008996.1 |
| MGA(5.7%), | NM_001080541.3 |

TABLE 3-continued 52 genes whose mutations influence immuotherapy outcomes.
Gene name (% with mutations in MSK-TMB-NSCLC cohort)
and GenBank Accession Nos.

| Gene Name | GenBank Accession No. |
|---|---|
| MRE11(2.0%), | NG_007261.1 |
| MSH2(2.0%), | NG_007110.2 |
| NF2(3.4%), | NG_009057.1 |
| NFKBIA(0.9%), | NG_007571.1 |
| NOTCH1(4.0%), | NG_007458.1 |
| NOTCH2(3.1%), | NG_008163.1 |
| NTRK3(5.7%), | NG_029619.1 |
| NUF2(0.9%), | NM_031423.4 |
| PARP1(1.1%), | NM_001618.4 |
| PAX5(1.1%), | NG_033894.1 |
| PGR(4.3%), | NG_016475.1 |
| PIK3C2G(4.0%), | NG_050635.1 |
| PIK3C3(3.7%), | NM_002647.4 |
| PIK3CG(7.7%), | NG_050579.1 |
| PIM1(0.9%), | NG_029601.1 |
| POLE(4.6%), | NG_033840.1 |
| PPM1D(1.4%), | NG_023265.1 |
| PPP2R1A(2.0%), | NG_047068.1 |
| PTPRD(12.3%), | NG_033963.1 |
| RET(2.9%), | NG_007489.1 |
| STAT3(0.9%), | NG_007370.1 |
| TENT5C(0.9%), | NM_017709.4 |
| TET1(2.3%), | NM_030625.3 |
| TSC2(2.6%), | NG_005895.1 |
| ZFHX3(7.7%) | NG_013211.2 |

Figure 11A:
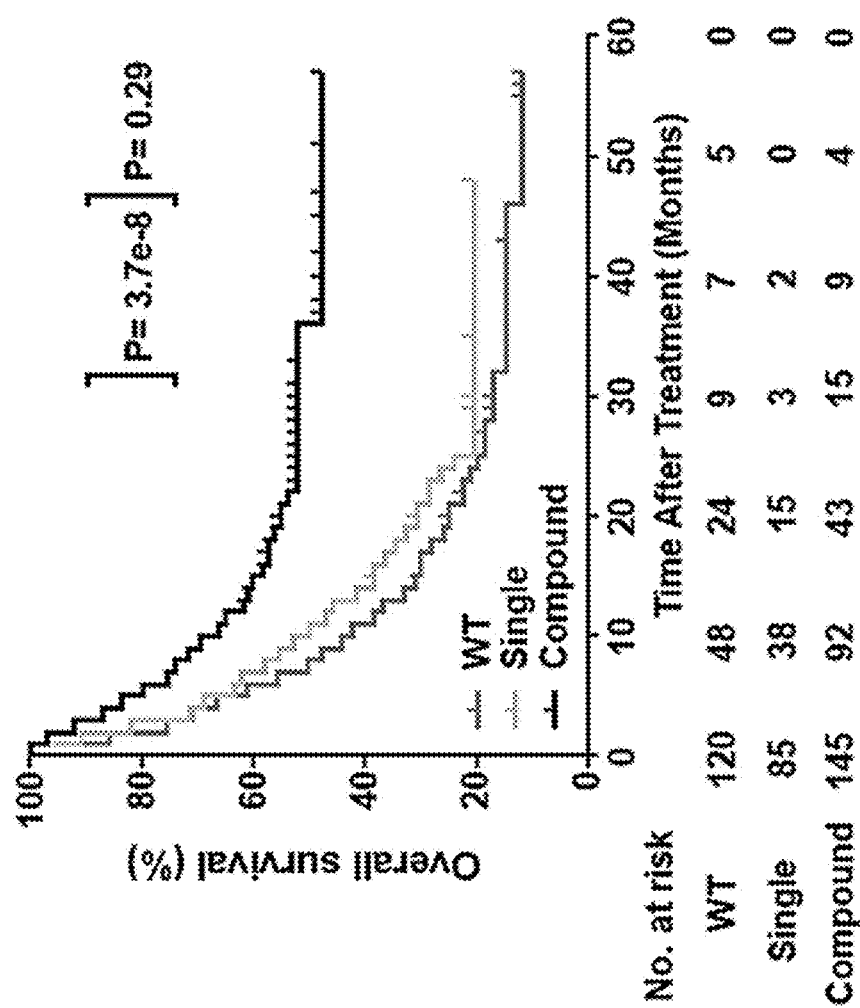
FIGS. 11A-11B are graphs showing the compound mutation signature in a 52-gene panel predicts for significantly better response to ICB treatment in NSCLC in accordance with an embodiment of the present disclosure.

The predictive power of different types of mutation signatures in the 52 genes was then determined by dividing the NSCLC patients in the MSK-TMB cohorts into the following three sub-cohorts with different mutation signature cohorts: those without mutations in the 52 genes (wt), those with only 1 of the 52 genes mutated (single), and those with 2 or more of the 52 genes mutated (compound). We compared the OS among the three cohorts (FIG. 11A). The data indicated that the median OS was 36 months among the 145 patients in the compound mutation group (vs 8 months for wt group, p=3.7e-8, logrank test). Importantly, the single mutation group was not significantly different from the wt group in terms of overall survival (p=0.29, log rank test). These data therefore showed significant overall survival advantages of the compound mutation group when compared with the wt or single mutation groups.

Figure 11B:
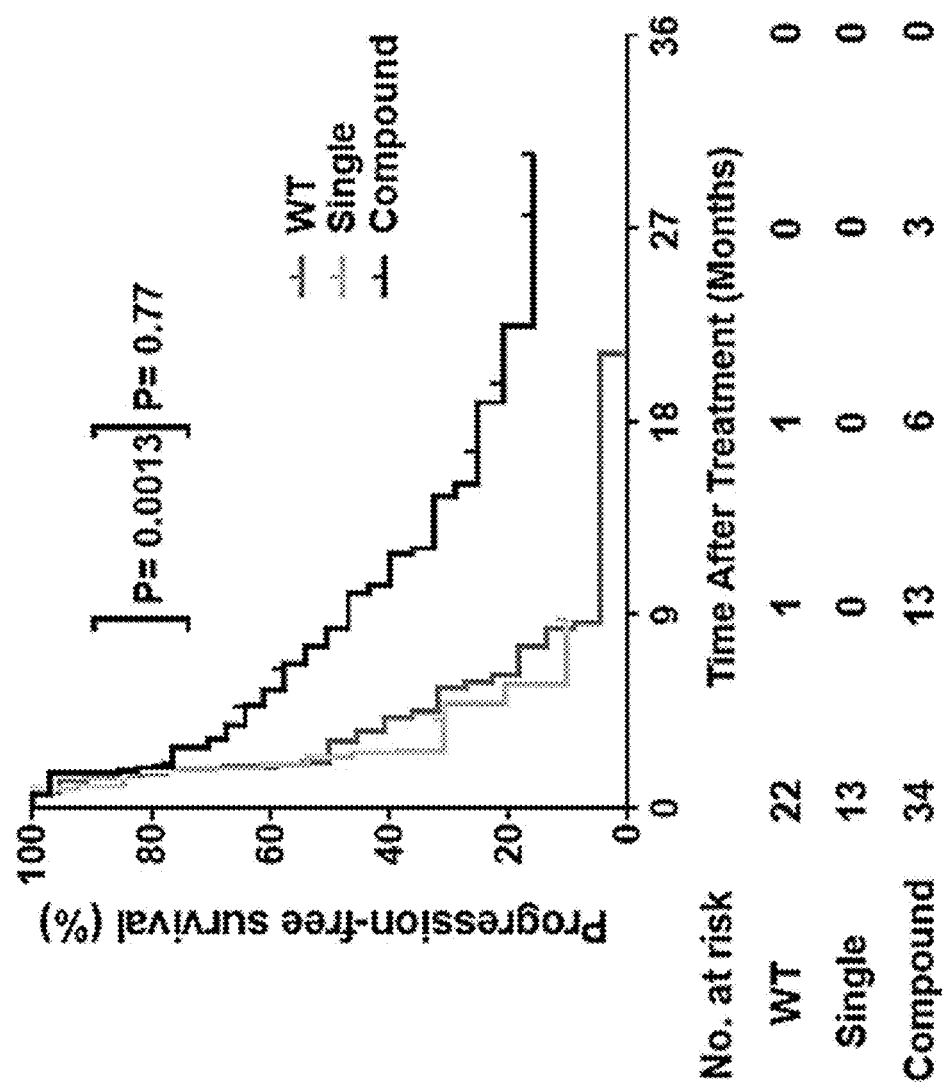

The influences of the mutation signatures on profession free survival (PFS) were compared in a sub-cohort 69 MSK-TMB NSCLC patients where PFS data were available (Rizvi et al., (2018). The indicated that 77 patients with the compound mutation signature had a median PFS of 8.33 months (vs 2.52 months for the wt group, p=0.0013, logrank test) (FIG. 11B). On the other hand, PFS for the single mutation group was 2.37 months (p=0.77 when compared with wt group). Therefore the association patterns between the mutation signatures and PFS was similar to that of the OS data.

The predictive power of the compound mutation signature in an independent cohort of 156 NSCLC patients from previously published studies (Rizvi et al. (2015); Hellmann et al., and Rizvi et al. (2018)) was validated. See, Table 4 for patient information.

Figure 12:
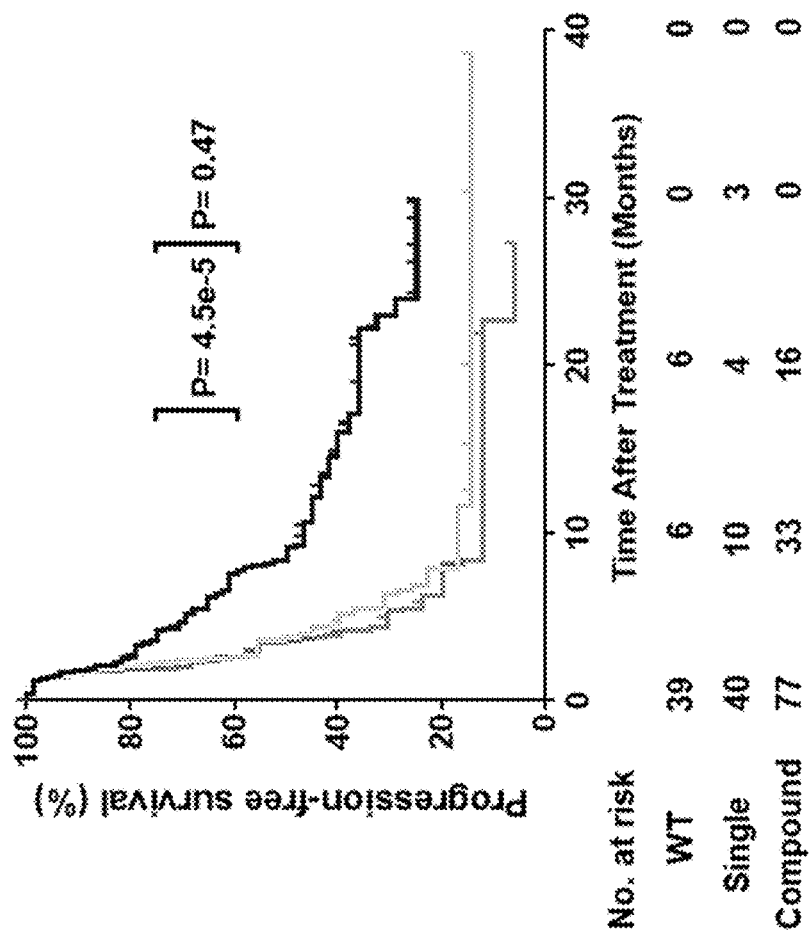
FIG. 12 is a graph showing validation of the predictive value of the compound mutation signature in an independent cohort of ICB-treated NSCLC patients. A Kaplan-Meier survival curve of 156 ICB-treated NSCLC patients with wt, single, or compound mutation signatures is shown. HR (Compound vs wt): 0.42 (95% [CI]: 0.24-0.71). P values calculated by use of logrank test.

(FIG. 12). These were remarkably similar to the PFS data obtained from the MSK-TMB cohort (FIG. 11B), thereby validating the predictive power of the compound mutation signature independently.

One important question is whether the observed clinical benefits in the compound mutation group were genetically inherent for the patients and therefore prognostic instead of predictive of clinical benefits from ICB treatment. In order to answer this important question, a sub-cohort of NSCLC patients in the MSK-IMPACT cohort who had not been treated with immunotherapy, but were otherwise very similar in patient characteristics to the MSK-TMB lung cancer

TABLE 4

Patient characteristics in the validation cohort

| NSCLC patient characteristics | WT N = 39 | Single N = 40 | Compound N = 77 | P value (Compound VS WT) |
|---|---|---|---|---|
| Median age (range, SEM), years | 64 ± 2.0 | 64 ± 1.5 | 65 ± 1.1 | 0.26* |
| Sex, n (%) | | | | |
| Male | 23, (59%) | 11, (28%) | 39, (51%) | 0.40 |
| Female | 16, (41%) | 39, (72%) | 38, (49%) | |
| Smoking History | | | | |
| Prev/Curr, n (%) | 25, (64%) | 31, (78%) | 68, (88%) | 0.0020 |
| Never, n (%) | 14, (36%) | 9, (22%) | 9, (12%) | |
| Cancer Type | | | | |
| Lung Adenocarcinoma, n (%) | 27, (69%) | 36, (90%) | 61, (80%) | 0.17 |
| Lung Squamous Cell Carcinoma, n (%) | 9, (23%) | 4, (10%) | 15, (19%) | |
| Other, n (%) | 3, (8%) | 0, (0%) | 1, (1%) | |
| Event Type | | | | |
| Progression-free Survival, n (%) | 7, (18%) | 8, (20%) | 29, (38%) | 0.027 |
| Censored, n (%) | 32, (82%) | 32, (80%) | 48, (62%) | |
| PD-L1 expression | | | | |
| 0%, n (%) | 5, (13%) | 16, (40%) | 20, (26%) | 0.49 |
| ≥1%, n (%) | 16, (41%) | 17, (43%) | 43, (56%) | |
| Unknow, n (%) | 18, (46%) | 7, (17%) | 14, (18%) | |
| Median TMB Score (range, SEM), | 4.08 ± 0.79 | 4.78 ± 0.88 | 11.23 ± 1.45 | 2.9e−5* |

*P values were calculated by use of unpaired t-test. The other P values were calculated by use of Chi-Squared Test.

Figure 13:
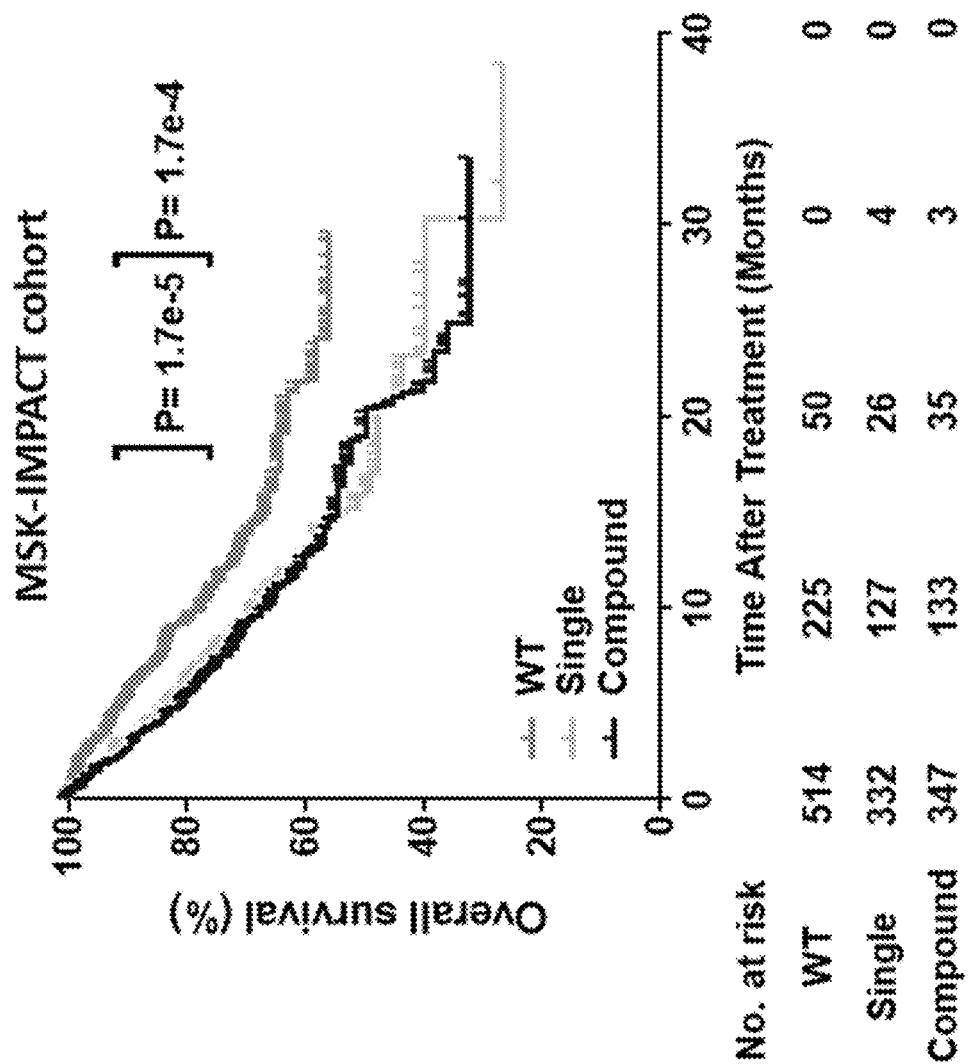
FIG. 13 is a graph showing the non-prognostic nature of the compound mutation signature in non-ICB treated NSCLC patients from the MSK-IMPACT cohort. Kaplan-Meier analysis of the OS levels in a sub-cohort of 1193 non-ICB treated NSCLC patients from the MSK-IMACT cohort with different mutation signatures is shown. HR (compound vs wt): 1.7 (95% [CI]: 1.32-2.20). P values calculated by use of logrank test.

Different from the MSK-TMB cohort, these ICB-treated patients were sequenced by WES (whole exome sequencing) for gene mutations. Survival analysis of patients with different mutation signatures in the 52-gene panel was conducted. Results showed patients with the compound mutation signature showed significant survival advantages (FIG. 12). The median progression free survival (PFS) was 3.5 months, 3.7 months, and 8.3 months in the wt, single, and compound mutation groups in NSCLC patients, respectively cohort was studied. See Table 5 for patient information. The analysis indicated that in the absence of ICB treatment, the survival benefits observed in the compound mutation group were not observed (FIG. 13). In fact, the compound and single mutation group had worse survival than the wild type group. Therefore, the compound signature is predictive for NSCLC ICB therapy instead of prognostic for NSCLC in general.

TABLE 5

Patient characteristics in the MSK-IMPACT cohort

| NSCLC patient characteristics | WT N = 514 | Single N = 332 | Compound N = 347 | P value (Compound VS WT) |
|---|---|---|---|---|
| Sex, n (%) | | | | |
| Male | 214, (42%) | 135, (41%) | 155, (45%) | 0.38 |
| Female | 300, (58%) | 197, (59%) | 192, (55%) | |
| Smoking History | | | | |
| Prev/Curr, n (%) | 248, (48%) | 207, (62%) | 254, (73%) | <e−16 |
| Never, n (%) | 173, (34%) | 65, (20%) | 31, (9%) | |
| Unknown, n (%) | 93, (18%) | 60, (18%) | 62, (18%) | |

TABLE 5-continued

Patient characteristics in the MSK-IMPACT cohort

| NSCLC patient characteristics | WT<br>N = 514 | Single<br>N = 332 | Compound<br>N = 347 | P value<br>(Compound<br>VS WT) |
|---|---|---|---|---|
| Cancer Type | | | | |
| Lung Adenocarcinoma, n (%) | 416, (81%) | 279, (84%) | 276, (80%) | 0.85 |
| Lung Squamous Cell Carcinoma, n (%) | 47, (9%) | 31, (9%) | 38, (11%) | |
| Poorly Differentiated Non-Small Cell Lung Cancer, n (%) | 7, (1%) | 5, (2%) | 5, (1%) | |
| other, n (%) | 44, (9%) | 17, (5%) | 28, (8%) | |
| Sample Type | | | | |
| Primary, n (%) | 314, (61%) | 230, (69%) | 189, (54%) | 0.053 |
| Metastasis, n (%) | 200, (39%) | 102, (31%) | 158, (46%) | |
| Overall Survival Status | | | | |
| Living, n (%) | 389, (76%) | 214, (64%) | 228, (63%) | 0.0016 |
| Deceased, n (%) | 125, (24%) | 118, (36%) | 129, (37%) | |
| Median TMB Score (range, SEM), | 2.95 ± 0.12 | 5.90 ± 0.21 | 12.79 ± 0.55 | <e−16* |

*P values were calculated by use of unpaired t-test. Other P values were calculated by use of Chi-Squared Test.

The relationships between different gene mutation signatures and genes whose mutations previously associated with negative outcome from ICB therapy: EGFR, ALK, KRAS, and LKB, were also compared. The analysis indicated that mutations in these genes were not mutually exclusive with the compound mutation signature. In fact, they are quite evenly distributed across the three mutation group.

Figure 17A:
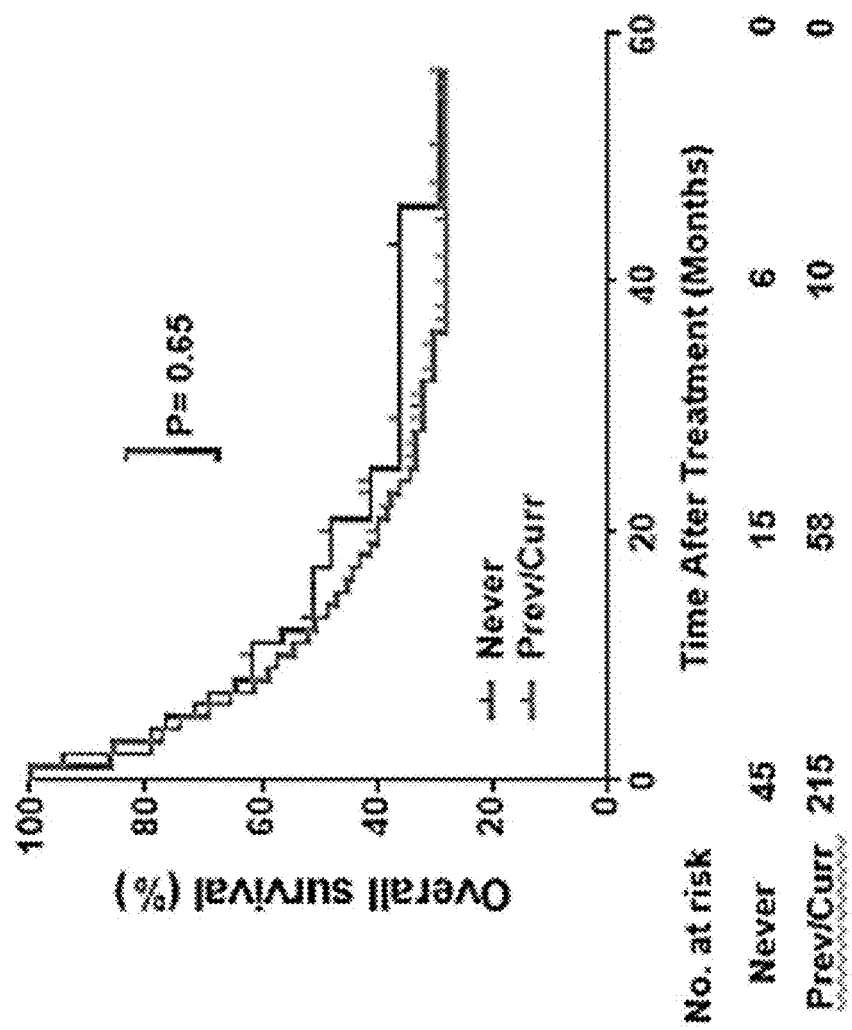
FIGS. 17A-17B show the lack of influence of smoking status on response to ICB treatment in NSCLC patients in two different patient cohorts.
Figure 17B:
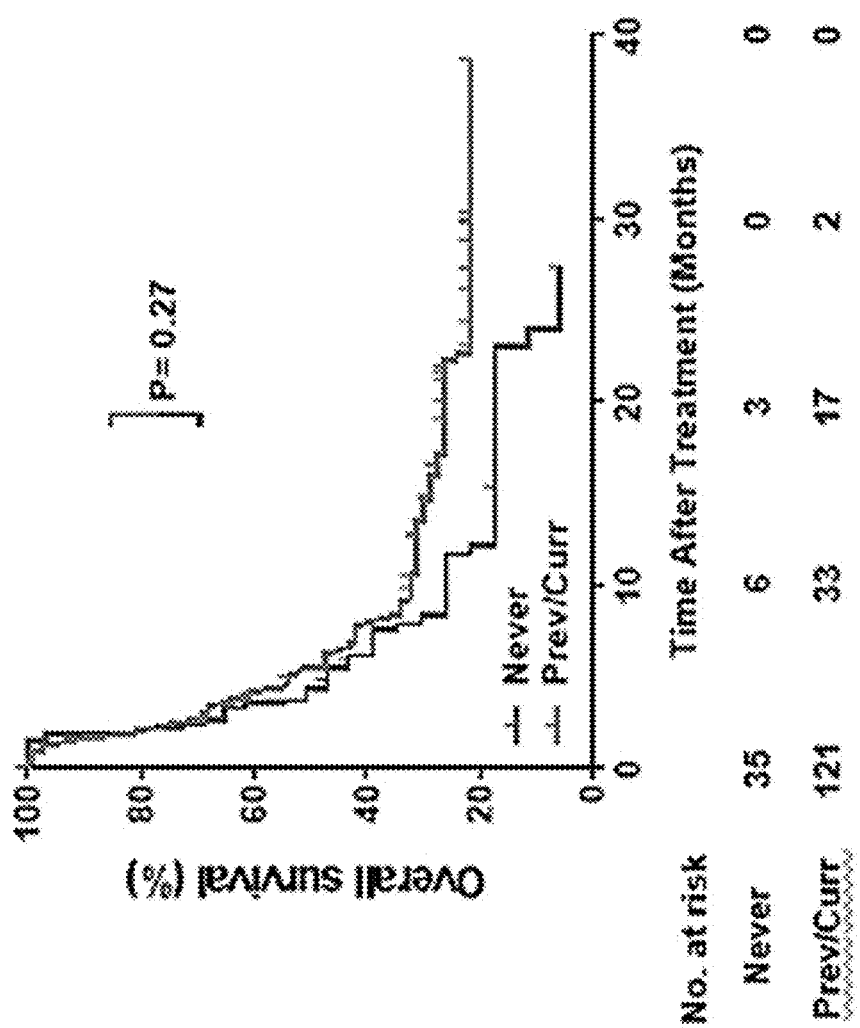

Whether the mutation signature was preferentially associated with two clinical features: tumor tissue histology or patient smoking history, was analyzed. The analysis indicated that the compound mutation signature did not preferentially enrich in either lung cancer with adenocarcinoma histology or squamous cell carcinoma histology. However, it was found that patients who are previous or current smokers did have a significantly higher chance of possessing the compound mutation signature. However, smoking status alone was not predictive of response to ICB therapy (FIG. 17A-B). Therefore, higher fractions of smokers tend to have the compound mutation signature but smoking status alone did not predict for superior response to ICB.

Figure 14A:
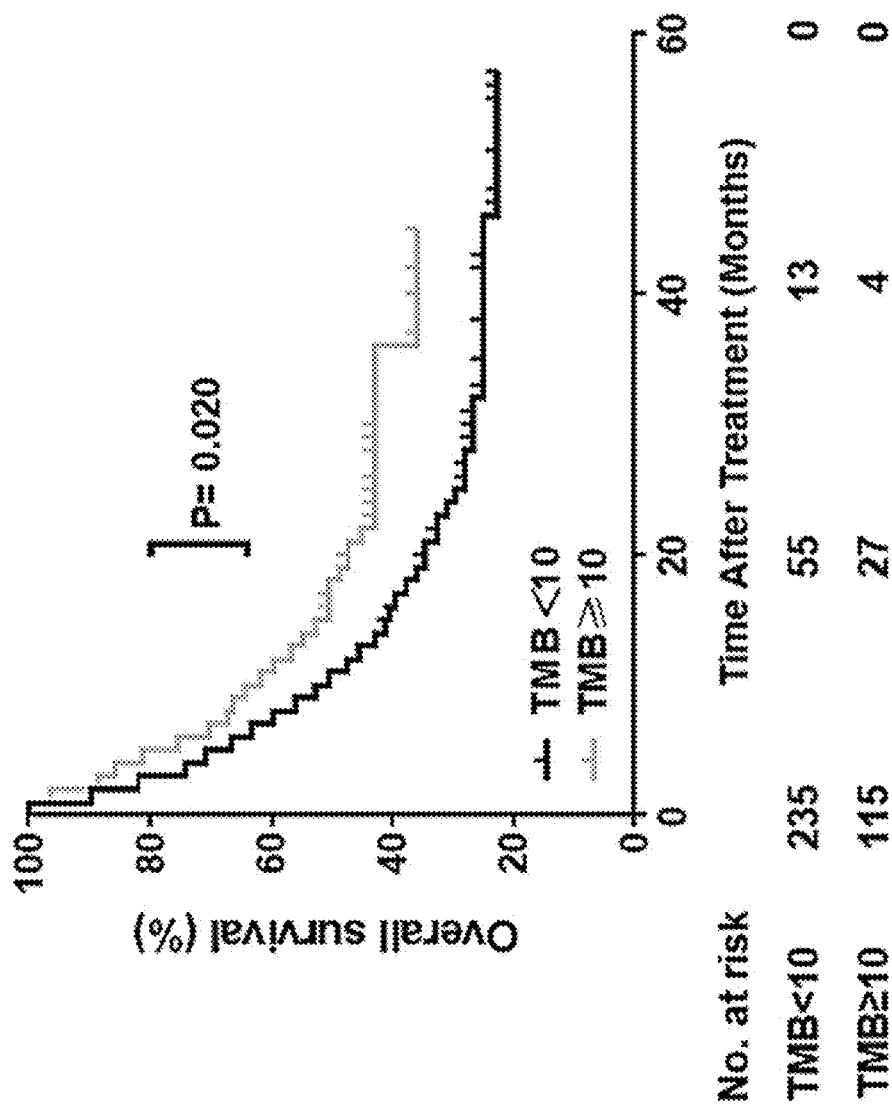
FIGS. 14A-14B provide a comparison of the predictive powers of TMB-H vs the compound signature in ICB-treated NSCLC patients.
Figure 14B:
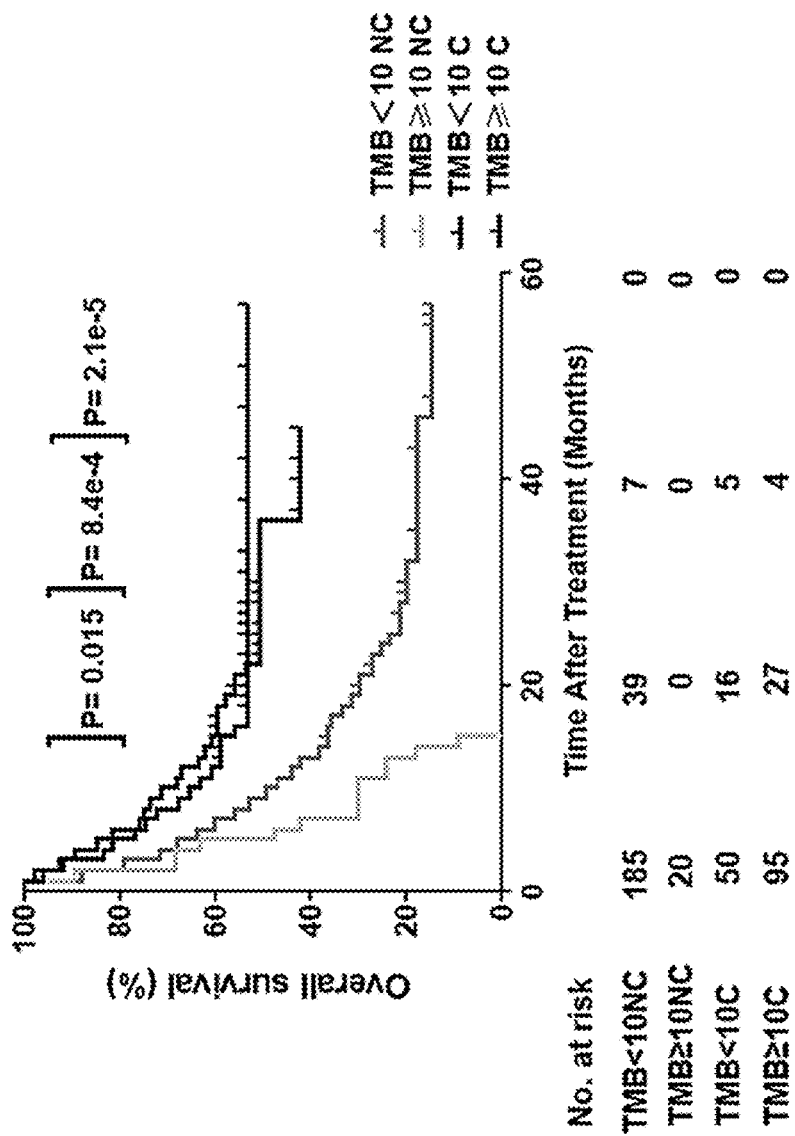
Figures 15A, 15B:
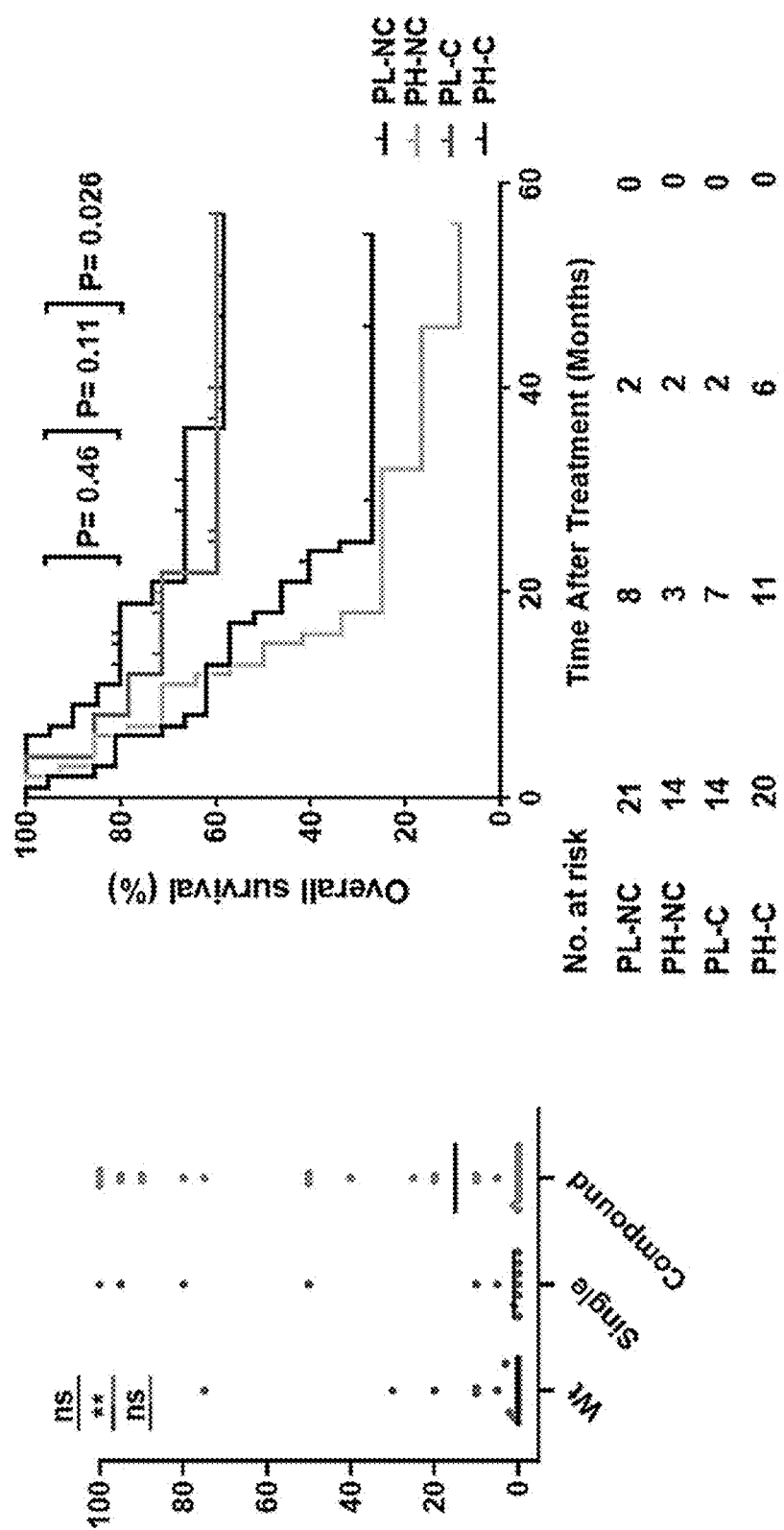
FIGS. 15A-15B show the independence of the compound mutation signature from PD-L1 in predicting ICB treatment response.

We next compared the relative predictive powers of the compound mutation signature vs TMB. The FDA recently approved pembrolizumab treatment for pediatric and adult solid tumors that are TMB-H (≥10). The predictive power of TMB in the MSK-TMB cohort of NSCLC patients was evaluated. Data indicated that, among 350 NSCLC patients, 115 are TMB-H. When compared with those with TMB<10, TMB-H patients had a clear survival benefits (FIG. 14A), with median OS at 18 months (vs 11 months in the TMB-L group). To compare the predictive power of TMB-H vs the compound mutation signature, patients with high or low TMB were stratified by the compound mutation signature and their OS levels were compared (FIG. 14B). These results indicated those patients low TMB (<10), but possessing the compound mutation signature had a significant survival advantage (median OS unreached) when compared with those with no compound mutation signatures with either high (median OS 5.0 months) or low (median OS 9.0 month) TMB. Furthermore, the compound mutation signature captured 145 patients vs 115 patients captured by TMB-H. Therefore, this analysis clearly demonstrated the superiority of the compound mutation signature in predicting ICB benefits compared with TMB (≥10) in NSCLC patients.

The relationship between the compound mutation signature and PD-L1 levels in predicting NSCLC response to ICB treatment was also evaluated, because the latter is currently the most widely used biomarker to select NSCLC patients for immunotherapy. To carry out the analysis, a sub-cohort of the MSK-TMB cohort of NSCLC patients for whom the PD-L1 expression data was published (Rizvi et al. (2018), was used. Patients with all three mutation signatures had a range of PD-L1 expression levels with the compound mutation group possessing the highest average level (but not statistically different when compared with the other two groups) (FIG. 14A). Importantly, survival analysis indicated that those patients with the compound mutation signature had a significantly better OS level irrespective of whether they have high or low PD-L1 expression levels (FIG. 14B). Therefore, the compound mutation signature predicts for ICB benefits independent of the PD-L1 expression levels.

Figure 16B:
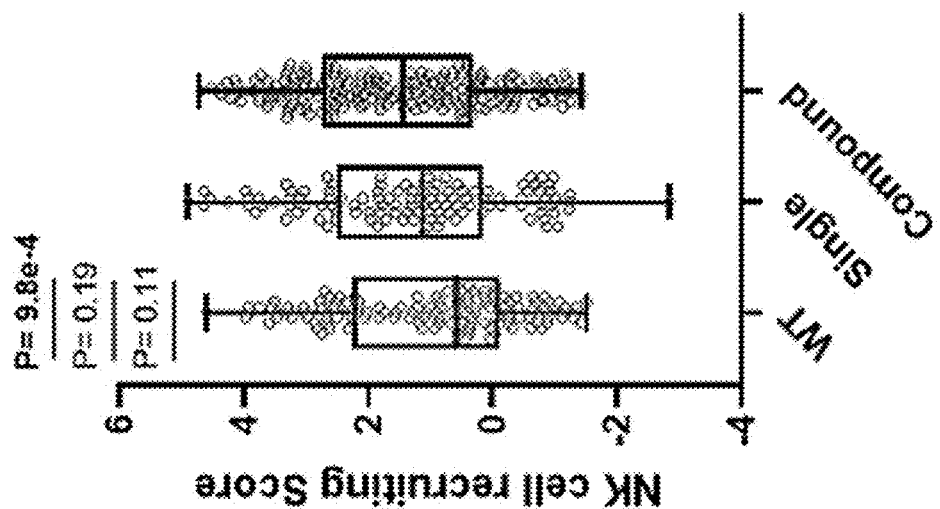
FIGS. 16A-16D show the association of the compound mutation signature with a pro-inflammatory tumor microenvironment. A cohort of NSCLC patients from the TCGA Pan-Cancer Atlas were analyzed for their CIBERSORT immune effector scores based on their mutation signatures.
Figure 16A:
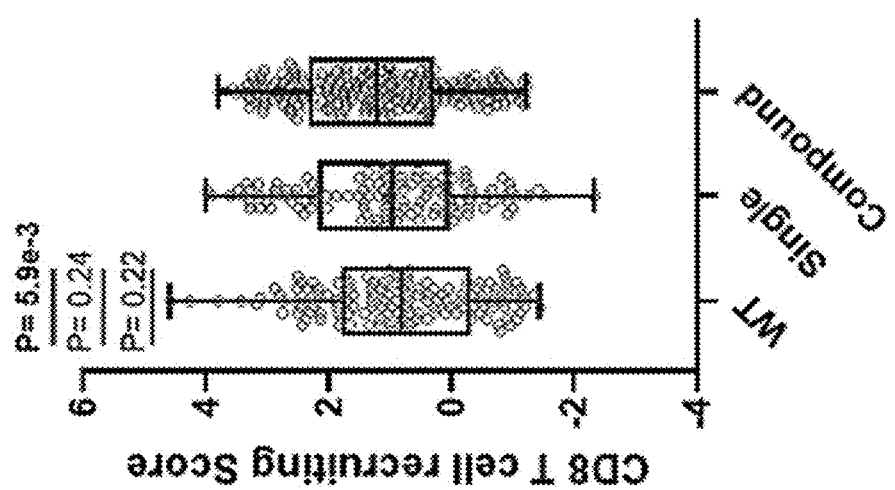
Figure 16D:
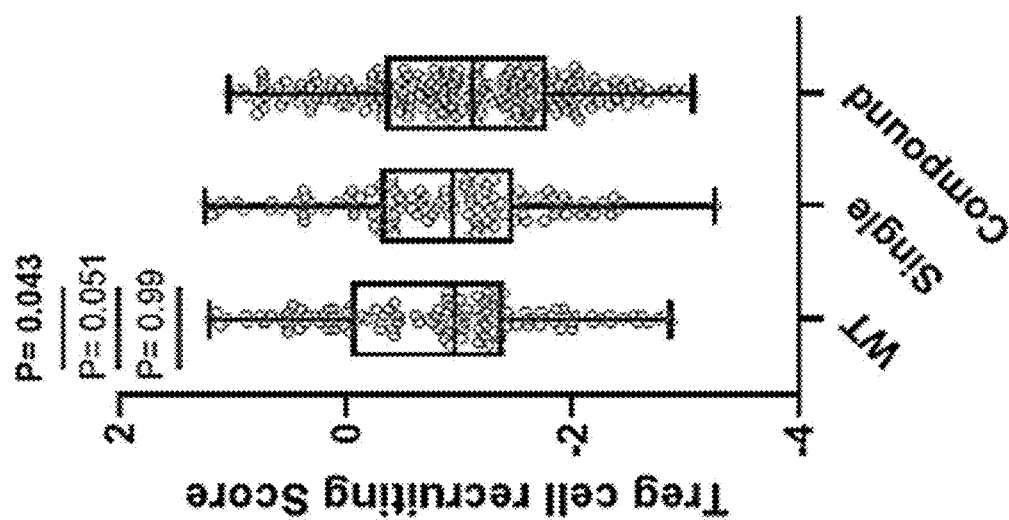
Figure 16C:
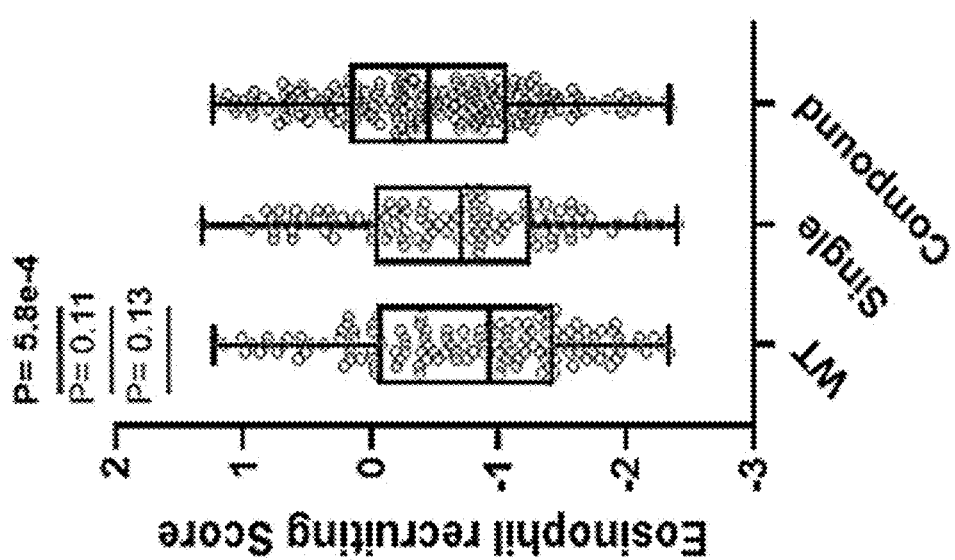

Based on the hypothesis that gene mutations not only provide neoantigens that might be recognized by the immune system but may also influence the biology of the tumors, it was postulated that the compound mutation signature may be associated with altered tumor immune microenvironment. In order to test this hypothesis, gene expression data from 501 NSCLC patients, from the TCGA Pan Cancer Atlas cohort, based on their mutation signatures using the CIBERSORT method, and TIP, was analyzed. The CIBERSORT methods can accurately enumerate different immunoeffector cellular subsets in tumor tissues based on RNA expression data. The analysis indicated that in the TCGA NSCLC patient cohort, tumors with the compound mutation signature had significantly more intratumoral infiltration of CD8+ T cells (FIG. 16A), NK cells (FIG. 16B), and eosinophils (FIG. 16C). On the other hand, the numbers of intratumoral Tregs were significantly reduced (FIG. 16D). These data thus suggest that the compound mutation signature in the 52-gene panel predicts for a pro-inflammatory tumor immune microenvironment in NSCLC that is conducive to ICB treatment.

Although there is an abundance of evidence to associate high TMB with NSCLC response to ICB treatment, the use of TMB as a biomarker in the clinic has been hampered by the lack of clearly defined cut-offs because of the great variability in TMB among different cancer patient cohorts2.

Thus the recent FDA approval of TMB≥10 for pembrolizumab treatment was a significant step in the use of TMB for selecting patients for treatment. On the other hand, the finding that the compound mutation signature in the 52-gene panel predicted NSCLC ICB therapy response more favorably than those with high TMB (≥10) showed that there is significant space for improvement in using TMB to select patients, at least in NSCLC. The results shown herein provide a rationale for analyzing additional cohorts of ICB-treated patients or conducting new prospective clinical trials to validate if the compound mutation signature may serve as a biomarker for selecting patients suitable for ICB therapy.

The 52-gene panel was selected using criteria that are agnostic of their biological functions. The standard that, the difference of mutation frequencies in the surviving vs deceased patients have to be significant, was used. $p \leq 0.1$ was chosen as a compromise standard to include more genes on the list.

At a practical level, the compound mutation signature as a predictive biomarker has some potential advantages. As set forth above, compound mutation identification can be achieved with different platform technologies, including archival FFPE tissues and liquid biopsies such as patients' blood, saliva, or urine samples. In conclusion, the studies described herein revealed that a compound mutational signature with 2 or more of the 52-gene panel mutated predicted for response to ICB therapy.

What is claimed is:

1. A method for treating cancer in a subject comprising:
   (a) detecting the presence or absence of a mutation in each of a plurality of genes associated with responsiveness to immune checkpoint blockade (ICB) therapy, in a biological sample from a subject having non-small cell lung cancer (NSCLC),
   wherein the plurality of genes associated with responsiveness to ICB therapy consists of the genes: ABLI, ASXLI, ATM, BCOR, BRCA2, BRIP1, CARD11, CD79B, CDC73, CIC, EPHA3, EPHAS, EPHA, EPHB1, ERBB4, ERCC4, FGFR4, FLT3, FOXL2, HGF, INHBA, JAK3, MAX, MDC1, MED12, MET, MGA, MRE11, MSH2 NF2, NFKBIA, NOTCH1, NOTCH2, NTRK3, NUF, PARP], PAX5, PGR, PIK3C2G, PIK3C3, PIK3CG, PIM1, POLE, PPMID, PPP2RIA, PTPRD, RET, STAT3, TENT, TET1, TSC2, and ZFHX3; and
   (b) administering an ICB therapy to the subject having cancer when the subject has mutations in two or more of the plurality of genes associated with responsiveness to ICB therapy.

2. The method of claim 1 wherein the ICB therapy is selected from the group consisting of a PD-1 inhibitor, a PD-L1 inhibitor, a CTLA4 inhibitor, and combinations thereof.

3. The method of claim 1, wherein the ICB therapy comprises an antibody selected from the group consisting of an anti-PD1 antibody, anti-PD-L1 antibody, an anti-CTLA4 antibody, and any combinations thereof.

4. The method of claim 3, wherein the antibody is selected from the group consisting of atezolizumab, avelumab, camrelizumab, cemiplimab, durvalumab, ipilimumab, nivolumab, pembrolizumab, sintilimab, tislelizumab, toripalimab, tremelimumab, and any combinations thereof.

5. The method of claim 1, wherein the one or more mutations are identified by next generation sequencing, whole exome sequencing, polymerase chain reaction, Sanger sequencing, or targeted sequencing techniques.

6. The method of claim 1, wherein the one or more mutations are identified via DNA or RNA microarray analysis.

7. The method of claim 1, wherein the biological sample is a tumor biopsy from the subject.

8. The method of claim 7, where in the biological sample is a formalin-fixed paraffin-embedded (FFPE) tumor biopsy or liquid biopsy.

9. The method of claim 8, wherein the liquid biopsy is a blood, saliva, or urine sample.

10. The method of claim 1, wherein the biological sample comprises circulating tumor cells.

11. The method of claim 1, wherein the biological sample comprises circulating free DNA from the subject's blood.

12. The method of claim 1, further comprising collecting a biological sample from a subject having NSCLC prior to step (a) for analysis of the genes associated with responsiveness to immune checkpoint blockade (ICB) therapy.

13. The method of claim 1, wherein the ICB therapy is delivered in an effective amount to reduce one or more symptoms of NSCLC.

* * * * *